United States Patent
Mashiach

(10) Patent No.: US 11,253,712 B2
(45) Date of Patent: *Feb. 22, 2022

(54) SLEEP DISORDERED BREATHING TREATMENT APPARATUS

(71) Applicant: Nyxoah SA, Mont-St-Guibert (BE)

(72) Inventor: Adi Mashiach, Tel Aviv (IL)

(73) Assignee: Nyxoah SA, Mont-Saint-Guibert (BE)

( * ) Notice: Subject to any disclaimer, the term of this patent is extended or adjusted under 35 U.S.C. 154(b) by 0 days.

This patent is subject to a terminal disclaimer.

(21) Appl. No.: 14/623,190

(22) Filed: Feb. 16, 2015

(65) Prior Publication Data

US 2015/0290465 A1    Oct. 15, 2015

Related U.S. Application Data

(60) Continuation-in-part of application No. 14/322,877, filed on Jul. 2, 2014, now Pat. No. 9,327,132, which
(Continued)

(51) Int. Cl.
*A61N 1/378* (2006.01)
*A61N 1/36* (2006.01)
(Continued)

(52) U.S. Cl.
CPC .......... *A61N 1/3787* (2013.01); *A61N 1/3611* (2013.01); *A61N 1/36125* (2013.01);
(Continued)

(58) Field of Classification Search
CPC ............... A61N 1/3787; A61N 1/3611; A61N 1/36125; A61N 1/36189; A61N 1/37229;
(Continued)

(56) References Cited

U.S. PATENT DOCUMENTS 4,905,011 A    2/1990  Shea
5,463,285 A *  10/1995 El-Hamamsy ..... H05B 41/2806
                                              315/209 R
(Continued)

FOREIGN PATENT DOCUMENTS

DE    10003338 A1    11/2000
DE    69526767 T2    1/2003
(Continued)

OTHER PUBLICATIONS

European Search Report in related European Patent Application No. 13823270.7-166/2877090, dated Mar. 2, 2016, 7 pages.

*Primary Examiner* — Jennifer Pitrak McDonald
*Assistant Examiner* — Pamela M. Bays
(74) *Attorney, Agent, or Firm* — Finnegan, Henderson, Farabow, Garrett & Dunner, LLP

(57) ABSTRACT

Some embodiments of the disclosure may include a device for wirelessly powering an implant unit in a body of a subject from a location outside of the body of the subject, wherein the implant unit includes a secondary antenna for wirelessly receiving energy. The device may include a primary antenna configured to be located external to the body of the subject, a circuit electrically connected to the primary antenna, and at least one processor electrically connected to the primary antenna and the circuit. The at least one processor may determine a resonant frequency mismatch between a first resonant frequency associated with the primary antenna and a second resonant frequency associated with the secondary antenna associated with the implant unit; and apply an adjustment to at least one component of the circuit to cause a change in the first resonant frequency associated with the primary antenna and a reduction in the resonant frequency mismatch.

7 Claims, 28 Drawing Sheets

Related U.S. Application Data is a division of application No. 13/951,606, filed on Jul. 26, 2013, now Pat. No. 8,812,135, application No. 14/623,190, which is a continuation-in-part of application No. 14/159,663, filed on Jan. 21, 2014, now Pat. No. 9,521,483, which is a division of application No. 13/952,031, filed on Jul. 26, 2013, now Pat. No. 8,897,880, application No. 14/623,190, which is a continuation-in-part of application No. 14/059,632, filed on Oct. 22, 2013, now Pat. No. 9,855,032, which is a continuation of application No. 13/951,753, filed on Jul. 26, 2013, now Pat. No. 9,115,231, application No. 14/623,190, which is a continuation-in-part of application No. 13/951,590, filed on Jul. 26, 2013, now Pat. No. 9,031,653, and a continuation-in-part of application No. 14/496,212, filed on Sep. 25, 2014, now Pat. No. 9,220,908, which is a division of application No. 13/951,856, filed on Jul. 26, 2013, now Pat. No. 8,903,515, application No. 14/623,190, which is a continuation-in-part of application No. 13/952,015, filed on Jul. 26, 2013, now Pat. No. 9,555,257, and a continuation-in-part of application No. 13/952,063, filed on Jul. 26, 2013, now Pat. No. 9,526,906, and a continuation-in-part of application No. 14/059,651, filed on Oct. 22, 2013, now Pat. No. 9,504,828, which is a continuation of application No. 13/952,027, filed on Jul. 26, 2013, now Pat. No. 8,948,871, application No. 14/623,190, which is a continuation-in-part of application No. 13/952,152, filed on Jul. 26, 2013, now Pat. No. 9,095,725, and a continuation-in-part of application No. 13/952,150, filed on Jul. 26, 2013, now Pat. No. 10,918,376, and a continuation-in-part of application No. 14/476,715, filed on Sep. 3, 2014, now Pat. No. 9,220,907, which is a division of application No. 13/952,106, filed on Jul. 26, 2013, now Pat. No. 8,838,256, application No. 14/623,190, which is a continuation-in-part of application No. 13/952,143, filed on Jul. 26, 2013, now Pat. No. 8,958,893, and a continuation-in-part of application No. 13/952,082, filed on Jul. 26, 2013, now Pat. No. 9,511,238.

(60) Provisional application No. 61/676,327, filed on Jul. 26, 2012.

(51) Int. Cl.
| | |
|---|---|
| *A61N 1/372* | (2006.01) |
| *H02J 50/12* | (2016.01) |
| *H02J 50/90* | (2016.01) |
| *H02J 50/80* | (2016.01) |
| *H04B 5/00* | (2006.01) |
| *A61N 1/05* | (2006.01) |
| *A61F 2/30* | (2006.01) |
| *A61B 5/00* | (2006.01) |

(52) U.S. Cl.
CPC ..... *A61N 1/36189* (2013.01); *A61N 1/37229* (2013.01); *H02J 50/12* (2016.02); *H02J 50/90* (2016.02); *A61B 5/0031* (2013.01); *A61F 2002/30668* (2013.01); *A61F 2250/0001* (2013.01); *A61N 1/0526* (2013.01); *A61N 1/3601* (2013.01); *H02J 50/80* (2016.02); *H04B 5/0031* (2013.01); *H04B 5/0037* (2013.01); *H04B 5/0081* (2013.01); *H04B 5/0093* (2013.01); *Y10T 29/49018* (2015.01)

(58) Field of Classification Search
CPC ......... A61B 5/0031; A61F 2002/30668; A61F 2250/0001; H02J 7/025; H02J 50/12; H02J 50/90
USPC .......................................................... 607/61
See application file for complete search history.

(56) References Cited

U.S. PATENT DOCUMENTS

| | | |
|---|---|---|
| 5,540,732 A | 7/1996 | Testerman |
| 5,540,733 A | 7/1996 | Testerman et al. |
| 5,546,952 A | 8/1996 | Erickson |
| 5,549,655 A | 8/1996 | Erickson |
| 5,591,216 A | 1/1997 | Testerman et al. |
| 5,690,693 A | 11/1997 | Wang et al. |
| 5,702,431 A | 12/1997 | Wang et al. |
| 5,725,564 A | 3/1998 | Freed et al. |
| 5,741,316 A | 4/1998 | Chen et al. |
| 5,871,512 A | 2/1999 | Hemming et al. |
| 5,873,898 A | 2/1999 | Hemming et al. |
| 5,891,185 A | 4/1999 | Freed et al. |
| 5,945,762 A | 8/1999 | Chen et al. |
| 5,948,006 A | 9/1999 | Mann |
| 5,987,359 A | 11/1999 | Freed et al. |
| 6,009,878 A | 1/2000 | Weijand et al. |
| 6,038,480 A | 3/2000 | Hrdlicka et al. |
| 6,051,017 A | 4/2000 | Loeb et al. |
| 6,058,330 A | 5/2000 | Borza |
| 6,092,531 A | 7/2000 | Chen et al. |
| 6,104,958 A | 8/2000 | Freed et al. |
| 6,132,384 A | 10/2000 | Christopherson et al. |
| 6,134,473 A | 10/2000 | Hemming et al. |
| 6,144,881 A | 11/2000 | Hemming et al. |
| 6,163,724 A | 12/2000 | Hemming et al. |
| 6,175,764 B1 | 1/2001 | Loeb et al. |
| 6,181,965 B1 | 1/2001 | Loeb et al. |
| 6,185,455 B1 | 2/2001 | Loeb et al. |
| 6,198,970 B1 | 3/2001 | Freed et al. |
| 6,212,431 B1 | 4/2001 | Hahn et al. |
| 6,214,032 B1 | 4/2001 | Loeb et al. |
| 6,240,316 B1 | 5/2001 | Richmond et al. |
| 6,240,318 B1 | 5/2001 | Phillips |
| 6,251,126 B1 | 6/2001 | Ottenhoff et al. |
| 6,269,269 B1 | 7/2001 | Ottenhoff et al. |
| 6,275,737 B1 | 8/2001 | Mann |
| 6,281,611 B1 | 8/2001 | Chen et al. |
| 6,305,381 B1 | 10/2001 | Weijand et al. |
| 6,324,430 B1 | 11/2001 | Zarinetchi et al. |
| 6,324,431 B1 | 11/2001 | Zarinetchi et al. |
| 6,331,744 B1 | 12/2001 | Chen et al. |
| 6,344,021 B1 | 2/2002 | Juster et al. |
| 6,345,202 B2 | 2/2002 | Richmond et al. |
| 6,358,281 B1 | 3/2002 | Berrang et al. |
| 6,389,318 B1 | 5/2002 | Zarinetchi et al. |
| 6,430,444 B1 | 8/2002 | Borza |
| 6,473,653 B1 | 10/2002 | Schallhorn et al. |
| 6,477,425 B1 | 11/2002 | Nowick et al. |
| 6,496,733 B2 | 12/2002 | Zarinetchi et al. |
| 6,572,543 B1 | 6/2003 | Christopherson et al. |
| 6,574,507 B1 | 6/2003 | Bonnet |
| 6,587,725 B1 | 7/2003 | Durand et al. |
| 6,622,049 B2 | 9/2003 | Penner et al. |
| 6,628,989 B1 | 9/2003 | Penner et al. |
| 6,636,767 B1 | 10/2003 | Knudson et al. |
| 6,648,914 B2 | 11/2003 | Berrang et al. |
| 6,657,351 B2 | 12/2003 | Chen et al. |
| 6,684,105 B2 | 1/2004 | Cohen et al. |
| 6,704,602 B2 | 3/2004 | Berg et al. |
| 6,735,475 B1 | 5/2004 | Whitehurst et al. |
| 6,736,771 B2 | 5/2004 | Sokolich et al. |
| 6,738,671 B2 | 5/2004 | Christophersom et al. |
| 6,764,446 B2 | 7/2004 | Wolinsky et al. |
| 6,770,022 B2 | 8/2004 | Mechlenburg et al. |
| 6,788,975 B1 | 9/2004 | Whitehurst et al. |
| 6,839,594 B2 | 1/2005 | Cohen et al. |
| 6,845,271 B2 | 1/2005 | Fang et al. |

(56) References Cited

U.S. PATENT DOCUMENTS

| | | |
|---|---|---|
| 6,850,803 B1 | 2/2005 | Jimenez et al. |
| 6,892,098 B2 | 5/2005 | Ayal et al. |
| 6,907,295 B2 | 6/2005 | Gross et al. |
| 6,928,324 B2 | 8/2005 | Park et al. |
| 6,937,891 B2 | 8/2005 | Leinders et al. |
| 7,024,248 B2 | 4/2006 | Penner et al. |
| 7,027,860 B2 | 4/2006 | Bruninga et al. |
| 7,039,468 B2 | 5/2006 | Freed et al. |
| 7,054,691 B1 | 5/2006 | Kuzma et al. |
| 7,103,408 B2 | 9/2006 | Haller et al. |
| 7,120,992 B2 | 10/2006 | He et al. |
| 7,132,173 B2 | 11/2006 | Daulton |
| 7,146,221 B2 | 12/2006 | Krulevitch et al. |
| 7,149,586 B2 | 12/2006 | Greenberg et al. |
| 7,155,278 B2 | 12/2006 | King et al. |
| 7,167,737 B2 | 1/2007 | Fujii et al. |
| 7,177,698 B2 | 2/2007 | Klosterman et al. |
| 7,181,287 B2 | 2/2007 | Greenberg |
| 7,198,603 B2 | 4/2007 | Penner et al. |
| 7,209,790 B2 | 4/2007 | Thompson et al. |
| 7,212,862 B2 | 5/2007 | Park et al. |
| 7,225,032 B2 | 5/2007 | Schmeling et al. |
| 7,257,438 B2 | 8/2007 | Kinast |
| 7,263,403 B2 | 8/2007 | Greenberg et al. |
| 7,273,457 B2 | 9/2007 | Penner |
| 7,277,749 B2 | 10/2007 | Gordon et al. |
| 7,280,873 B2 | 10/2007 | Freed et al. |
| 7,283,874 B2 | 10/2007 | Penner |
| 7,286,881 B2 | 10/2007 | Schommer et al. |
| 7,289,855 B2 | 10/2007 | Nghiem et al. |
| 7,308,316 B2 | 12/2007 | Schommer |
| 7,321,793 B2 | 1/2008 | Ben Ezra et al. |
| 7,324,853 B2 | 1/2008 | Ayal et al. |
| 7,338,522 B2 | 3/2008 | Greenberg et al. |
| 7,346,398 B2 | 3/2008 | Gross et al. |
| 7,351,921 B1 | 4/2008 | Haller et al. |
| 7,367,935 B2 | 5/2008 | Mechlenburg et al. |
| 7,392,091 B2 | 6/2008 | Bruinsma |
| 7,392,092 B2 | 6/2008 | Li et al. |
| 7,409,245 B1 | 8/2008 | Larson et al. |
| 7,428,438 B2 | 9/2008 | Parramon et al. |
| 7,437,193 B2 | 10/2008 | Parramon et al. |
| 7,447,551 B2 | 11/2008 | Kuo et al. |
| 7,482,783 B2 | 1/2009 | Schommer |
| 7,483,750 B2 | 1/2009 | Greenberg et al. |
| 7,489,966 B2 | 2/2009 | Leinders et al. |
| 7,493,172 B2 | 2/2009 | Whitehurst et al. |
| 7,499,754 B2 | 3/2009 | Greenberg et al. |
| 7,502,652 B2 | 3/2009 | Gaunt et al. |
| 7,512,443 B2 | 3/2009 | Phillips et al. |
| 7,527,621 B2 | 5/2009 | Greenberg et al. |
| 7,555,345 B2 | 6/2009 | Wahlstrand et al. |
| 7,561,922 B2 | 7/2009 | Cohen et al. |
| 7,587,241 B2 | 9/2009 | Parramon et al. |
| 7,599,744 B2 | 10/2009 | Giordano et al. |
| 7,610,065 B2 | 10/2009 | Vallapureddy et al. |
| 7,610,103 B2 | 10/2009 | Whitehurst et al. |
| 7,617,001 B2 | 11/2009 | Penner et al. |
| 7,628,750 B2 | 12/2009 | Cohen et al. |
| 7,630,771 B2 | 12/2009 | Cauller |
| 7,631,424 B2 | 12/2009 | Greenberg et al. |
| 7,634,317 B2 | 12/2009 | Ben-David et al. |
| 7,636,602 B2 | 12/2009 | Baru Fassio et al. |
| 7,640,061 B2 | 12/2009 | He et al. |
| 7,641,619 B2 | 1/2010 | Penner |
| 7,647,112 B2 | 1/2010 | Tracey et al. |
| 7,660,632 B2 | 2/2010 | Kirby et al. |
| 7,668,580 B2 | 2/2010 | Shin et al. |
| 7,668,602 B2 | 2/2010 | Ben-David et al. |
| 7,672,728 B2 | 3/2010 | Libbus et al. |
| 7,680,538 B2 | 3/2010 | Durand et al. |
| 7,684,866 B2 | 3/2010 | Fowler et al. |
| 7,711,435 B2 | 5/2010 | Schommer |
| 7,720,547 B2 | 5/2010 | Denker et al. |
| 7,725,195 B2 | 5/2010 | Lima et al. |
| 7,734,355 B2 | 6/2010 | Cohen et al. |
| 7,756,587 B2 | 7/2010 | Penner et al. |
| 7,766,216 B2 | 8/2010 | Daulton |
| 7,769,461 B2 | 8/2010 | Whitehurst et al. |
| 7,774,069 B2 | 8/2010 | Olson et al. |
| 7,778,702 B2 | 8/2010 | Ben-David et al. |
| 7,778,703 B2 | 8/2010 | Gross et al. |
| 7,778,711 B2 | 8/2010 | Ben-David et al. |
| 7,781,683 B2 | 8/2010 | Haller et al. |
| 7,797,050 B2 | 9/2010 | Libbus et al. |
| 7,805,203 B2 | 9/2010 | Ben-David et al. |
| 7,809,442 B2 | 10/2010 | Bolea et al. |
| 7,810,233 B2 | 10/2010 | Krulevitch et al. |
| 7,822,480 B2 | 10/2010 | Park et al. |
| 7,831,308 B2 | 11/2010 | Rezai et al. |
| 7,836,888 B2 | 11/2010 | Hegde et al. |
| 7,844,346 B2 | 11/2010 | Cohen et al. |
| 7,845,357 B2 | 12/2010 | Buscemi et al. |
| 7,881,800 B2 | 2/2011 | Daly et al. |
| 7,882,842 B2 | 2/2011 | Bhat et al. |
| 7,885,709 B2 | 2/2011 | Ben-David |
| 7,885,711 B2 | 2/2011 | Ben-Ezra et al. |
| 7,887,493 B2 | 2/2011 | Stahmann et al. |
| 7,890,178 B2 | 2/2011 | Testerman et al. |
| 7,890,185 B2 | 2/2011 | Cohen et al. |
| 7,890,193 B2 | 2/2011 | Tingey |
| 7,894,909 B2 | 2/2011 | Greenberg et al. |
| 7,904,151 B2 | 3/2011 | Ben-David et al. |
| 7,904,163 B2 | 3/2011 | Greenberg et al. |
| 7,904,167 B2 | 3/2011 | Klosterman et al. |
| 7,904,176 B2 | 3/2011 | Ben-Ezra et al. |
| 7,908,008 B2 | 3/2011 | Ben-David et al. |
| 7,909,037 B2 | 3/2011 | Hegde et al. |
| 7,909,038 B2 | 3/2011 | Hegde et al. |
| 7,925,356 B2 | 4/2011 | Li et al. |
| 7,930,031 B2 | 4/2011 | Penner |
| RE42,378 E | 5/2011 | Wolinsky et al. |
| 7,937,159 B2 | 5/2011 | Lima et al. |
| 7,945,334 B2 | 5/2011 | Jimenez et al. |
| 7,970,479 B2 | 6/2011 | Goroszeniuk |
| 7,973,722 B1 | 7/2011 | Hill et al. |
| 7,974,693 B2 | 7/2011 | Ben-David et al. |
| 7,979,126 B2 | 7/2011 | Payne et al. |
| 7,979,128 B2 | 7/2011 | Tehrani et al. |
| 7,979,137 B2 | 7/2011 | Tracey et al. |
| 7,980,248 B2 | 7/2011 | Hegde et al. |
| 7,991,478 B2 | 8/2011 | Greenberg et al. |
| 8,005,542 B2 | 8/2011 | Ben-Ezra et al. |
| 8,005,545 B2 | 8/2011 | Ben-David et al. |
| 8,010,205 B2 | 8/2011 | Rahman et al. |
| 8,014,878 B2 | 9/2011 | Greenberg et al. |
| 8,024,044 B2 | 9/2011 | Kirby et al. |
| 8,024,047 B2 | 9/2011 | Olson et al. |
| 8,027,735 B1 | 9/2011 | Tziviskos et al. |
| 8,032,227 B2 | 10/2011 | Parramon et al. |
| 8,035,255 B2 | 10/2011 | Kurs et al. |
| 8,036,745 B2 | 10/2011 | Ben-David et al. |
| 8,036,752 B2 | 10/2011 | Greenberg et al. |
| 8,060,197 B2 | 11/2011 | Ben-David et al. |
| 8,060,211 B2 | 11/2011 | Greenberg et al. |
| 8,065,021 B2 | 11/2011 | Gross et al. |
| 8,074,655 B2 | 12/2011 | Sanders |
| 8,078,284 B2 | 12/2011 | Greenberg et al. |
| 8,086,318 B2 | 12/2011 | Strother et al. |
| 8,115,618 B2 | 2/2012 | Robertson et al. |
| 8,116,881 B2 | 2/2012 | Cohen et al. |
| 8,122,596 B2 | 2/2012 | Krulevitch et al. |
| 8,126,562 B2 | 2/2012 | Fowler et al. |
| 8,127,424 B2 | 3/2012 | Haller et al. |
| 8,131,375 B2 | 3/2012 | Greenberg et al. |
| 8,140,167 B2 | 3/2012 | Donders et al. |
| 8,160,696 B2 | 4/2012 | Bendett et al. |
| 8,165,695 B2 | 4/2012 | DiUbaldi et al. |
| 8,170,680 B2 | 5/2012 | Ameri |
| 8,170,681 B2 | 5/2012 | Jimenez et al. |
| 8,174,460 B2 | 5/2012 | Larson et al. |
| 8,175,714 B2 | 5/2012 | Greenberg et al. |
| 8,175,716 B2 | 5/2012 | Rahman et al. |
| 8,180,460 B2 | 5/2012 | Nevsmith et al. |

(56) References Cited

U.S. PATENT DOCUMENTS

| | | | |
|---|---|---|---|
| 8,185,212 | B2 | 5/2012 | Carbunaru et al. |
| 8,204,591 | B2 | 6/2012 | Ben-David et al. |
| 8,214,009 | B2 | 7/2012 | Shin et al. |
| 8,214,045 | B2 | 7/2012 | Kronich et al. |
| 8,220,467 | B2 | 7/2012 | Sanders |
| 8,224,444 | B2 | 7/2012 | Ben-David et al. |
| 8,224,449 | B2 | 7/2012 | Carbunaru et al. |
| 8,229,567 | B2 | 7/2012 | Phillips et al. |
| 8,238,975 | B2 | 8/2012 | Vallapureddy et al. |
| 8,241,950 | B2 | 8/2012 | Pellinen et al. |
| 8,249,713 | B2 | 8/2012 | Fang et al. |
| 8,249,723 | B2 | 8/2012 | McCreery |
| 8,256,425 | B2 | 9/2012 | Bagley et al. |
| 8,260,432 | B2 | 9/2012 | DiGiore et al. |
| 8,260,439 | B2 | 9/2012 | Diubaldi et al. |
| 8,265,763 | B2 | 9/2012 | Fahey |
| 8,265,770 | B2 | 9/2012 | Toy et al. |
| 8,285,381 | B2 | 10/2012 | Fahey |
| 8,295,936 | B2 | 10/2012 | Wahlstrand et al. |
| 8,301,261 | B2 | 10/2012 | Bruinsma |
| 8,311,645 | B2 | 11/2012 | Bolea et al. |
| 8,336,553 | B2 | 12/2012 | Bhat et al. |
| 8,352,026 | B2 | 1/2013 | DiUbaldi |
| 8,359,108 | B2 | 1/2013 | McCreery |
| 8,369,957 | B2 | 2/2013 | Greenberg et al. |
| 8,381,735 | B2 | 2/2013 | Buscemi et al. |
| 8,386,046 | B2 | 2/2013 | Tesfayesus et al. |
| 8,386,048 | B2 | 2/2013 | McClure et al. |
| 8,386,056 | B2 | 2/2013 | Ben David et al. |
| 8,391,991 | B2 | 3/2013 | Rahman et al. |
| 8,406,886 | B2 | 3/2013 | Gaunt et al. |
| 8,408,213 | B2 | 4/2013 | Sanders |
| 8,417,343 | B2 | 4/2013 | Bolea et al. |
| 8,428,725 | B2 | 4/2013 | Meadows et al. |
| 8,428,727 | B2 | 4/2013 | Bolea et al. |
| 8,428,746 | B2 | 4/2013 | DiGiore et al. |
| 8,433,403 | B2 | 4/2013 | Fahey |
| 8,447,410 | B2 | 5/2013 | Greenberg et al. |
| 8,457,758 | B2 | 6/2013 | Olson et al. |
| 8,463,383 | B2 | 6/2013 | Sakai et al. |
| 8,463,394 | B2 | 6/2013 | Forsell |
| 8,463,395 | B2 | 6/2013 | Forsell |
| 8,473,025 | B2 | 6/2013 | Shin et al. |
| 8,489,200 | B2 | 7/2013 | Zarinetchi et al. |
| 8,494,641 | B2 | 7/2013 | Boling et al. |
| 8,494,655 | B2 | 7/2013 | Ayal et al. |
| 8,498,712 | B2 | 7/2013 | Bolea et al. |
| 8,498,716 | B2 | 7/2013 | Chen et al. |
| 8,509,909 | B2 | 8/2013 | Figueiredo et al. |
| 8,509,911 | B2 | 8/2013 | Li et al. |
| 8,510,939 | B2 | 8/2013 | Greenberg et al. |
| 8,515,544 | B2 | 8/2013 | Daly et al. |
| 8,532,787 | B2 | 9/2013 | Lambert et al. |
| 8,538,503 | B2 | 9/2013 | Kumar et al. |
| 8,540,631 | B2 | 9/2013 | Penner et al. |
| 8,540,632 | B2 | 9/2013 | Robertson et al. |
| 8,543,216 | B2 | 9/2013 | Carbunaru et al. |
| 8,560,046 | B2 | 10/2013 | Kumar et al. |
| 8,565,896 | B2 | 10/2013 | Ben-David et al. |
| 8,571,651 | B2 | 10/2013 | Ben-Ezra et al. |
| 8,571,653 | B2 | 10/2013 | Ben-David et al. |
| 8,571,679 | B2 | 10/2013 | Parramon et al. |
| 8,577,460 | B2 | 11/2013 | Penner |
| 8,578,937 | B2 | 11/2013 | Bhat et al. |
| 8,583,256 | B2 | 11/2013 | Tracey et al. |
| 8,588,901 | B2 | 11/2013 | Fahey |
| 8,588,924 | B2 | 11/2013 | Dion |
| 8,588,930 | B2 | 11/2013 | DiUbaldi et al. |
| 8,600,517 | B2 | 12/2013 | Forsell |
| 8,612,013 | B2 | 12/2013 | Forsell |
| 8,612,014 | B2 | 12/2013 | Rahman et al. |
| 8,615,294 | B2 | 12/2013 | Ben-David et al. |
| 8,620,437 | B2 | 12/2013 | Wahlstrand et al. |
| 8,620,447 | B2 | 12/2013 | D'Ambrosio et al. |
| 8,626,302 | B2 | 1/2014 | Bennett et al. |
| 8,626,304 | B2 | 1/2014 | Bolea et al. |
| 8,639,344 | B2 | 1/2014 | Greenberg et al. |
| 8,639,354 | B2 | 1/2014 | Bolea et al. |
| 8,644,939 | B2 | 2/2014 | Wilson et al. |
| 8,655,451 | B2 | 2/2014 | Klosterman et al. |
| 8,657,756 | B2 | 2/2014 | Stahmann et al. |
| 8,658,465 | B2 | 2/2014 | Pellinen et al. |
| 8,668,643 | B2 | 3/2014 | Kinast |
| 8,670,835 | B2 | 3/2014 | Park et al. |
| 8,676,332 | B2 | 3/2014 | Fahey |
| 8,700,177 | B2 | 4/2014 | Strother et al. |
| 8,703,537 | B2 | 4/2014 | Pellinen et al. |
| 8,718,758 | B2 | 5/2014 | Wagner et al. |
| 8,718,783 | B2 | 5/2014 | Bolea et al. |
| 8,718,791 | B2 | 5/2014 | Ben-David et al. |
| 8,725,271 | B2 | 5/2014 | Ayal et al. |
| 8,738,148 | B2 | 5/2014 | Olson et al. |
| 8,744,582 | B2 | 6/2014 | Wahlstrand et al. |
| 8,744,589 | B2 | 6/2014 | Bolea et al. |
| 8,751,003 | B2 | 6/2014 | DiUbaldi et al. |
| 8,751,005 | B2 | 6/2014 | Meadows et al. |
| 8,774,943 | B2 | 7/2014 | McCreery |
| 8,788,046 | B2 | 7/2014 | Bennett et al. |
| 8,788,047 | B2 | 7/2014 | Bennett et al. |
| 8,788,048 | B2 | 7/2014 | Bennett et al. |
| 8,798,763 | B2 | 8/2014 | Forsell |
| 8,813,753 | B2 | 8/2014 | Bhat et al. |
| 8,825,173 | B2 | 9/2014 | Forsell |
| 8,855,771 | B2 | 10/2014 | Tesfayesus et al. |
| 8,862,232 | B2 | 10/2014 | Zarinetchi et al. |
| 8,880,184 | B2 | 11/2014 | Phillips et al. |
| 8,886,304 | B2 | 11/2014 | Wagner et al. |
| 8,886,322 | B2 | 11/2014 | Meadows et al. |
| 8,886,325 | B2 | 11/2014 | Boling et al. |
| 8,886,329 | B2 | 11/2014 | Greenberg et al. |
| 8,886,337 | B2 | 11/2014 | Bennett et al. |
| 8,892,200 | B2 | 11/2014 | Wagner et al. |
| 8,892,205 | B2 | 11/2014 | Miller, III et al. |
| 8,892,210 | B2 | 11/2014 | Fahey |
| 8,897,871 | B2 | 11/2014 | Wagner et al. |
| 8,903,495 | B2 | 12/2014 | Greenberg et al. |
| 8,903,502 | B2 | 12/2014 | Perryman et al. |
| 8,914,129 | B2 | 12/2014 | Parramon et al. |
| 8,925,551 | B2 | 1/2015 | Sanders |
| 8,929,979 | B2 | 1/2015 | Wagner et al. |
| 8,929,986 | B2 | 1/2015 | Parker et al. |
| 8,934,972 | B2 | 1/2015 | Penner |
| 8,954,153 | B2 | 2/2015 | Boggs, II |
| 8,965,523 | B2 | 2/2015 | Forsell |
| 8,965,525 | B2 | 2/2015 | Forsell |
| 8,965,535 | B2 | 2/2015 | Dunlay et al. |
| 8,972,021 | B2 | 3/2015 | Edgell et al. |
| 8,977,354 | B2 | 3/2015 | Wagner et al. |
| 8,983,611 | B2 | 3/2015 | Mokelke et al. |
| 9,002,451 | B2 | 4/2015 | Staunton et al. |
| 9,026,222 | B2 | 5/2015 | Forsell |
| 9,031,654 | B2 | 5/2015 | Meadows et al. |
| 9,042,991 | B2 | 5/2015 | Reed et al. |
| 9,061,134 | B2 | 6/2015 | Askin, III et al. |
| 9,072,886 | B2 | 7/2015 | Gaunt et al. |
| 9,079,041 | B2 | 7/2015 | Park et al. |
| 9,079,043 | B2 | 7/2015 | Stark et al. |
| 9,089,690 | B2 | 7/2015 | Greenberg et al. |
| 9,113,838 | B2 | 8/2015 | Tesfayesus et al. |
| 9,125,290 | B2 | 9/2015 | Greenberg et al. |
| 9,126,039 | B2 | 9/2015 | Fahey |
| 9,149,228 | B2 | 10/2015 | Kinast |
| 9,149,386 | B2 | 10/2015 | Fahey et al. |
| 9,149,628 | B2 | 10/2015 | Wahlstrand et al. |
| 9,162,071 | B2 | 10/2015 | Parramon et al. |
| 9,186,496 | B2 | 11/2015 | Greenberg et al. |
| 9,186,511 | B2 | 11/2015 | Bolea |
| 9,205,258 | B2 | 12/2015 | Simon et al. |
| 9,205,262 | B2 | 12/2015 | Bolea et al. |
| 9,227,076 | B2 | 1/2016 | Sharma et al. |
| 9,233,258 | B2 | 1/2016 | Simon et al. |
| 9,241,649 | B2 | 1/2016 | Kumar et al. |
| 9,242,106 | B2 | 1/2016 | Klosterman et al. |
| 9,248,289 | B2 | 2/2016 | Bennett et al. |

(56) References Cited

U.S. PATENT DOCUMENTS

| | | |
|---|---|---|
| 9,272,081 B2 | 3/2016 | Cameron et al. |
| 9,289,142 B2 | 3/2016 | Kong et al. |
| 9,302,104 B2 | 4/2016 | Fahey |
| 9,308,370 B2 | 4/2016 | Lima et al. |
| 9,314,615 B2 | 4/2016 | Neysmith et al. |
| 9,314,618 B2 | 4/2016 | Imran et al. |
| 9,314,641 B2 | 4/2016 | Meadows et al. |
| 9,320,895 B2 | 4/2016 | Wagner et al. |
| 9,320,908 B2 | 4/2016 | Fletcher et al. |
| 9,339,647 B2 | 5/2016 | Strother et al. |
| 9,339,651 B2 | 5/2016 | Meadows et al. |
| 2002/0010495 A1 | 1/2002 | Freed et al. |
| 2002/0038138 A1 | 3/2002 | Zarinetchi et al. |
| 2002/0055763 A1 | 5/2002 | Zarinetchi et al. |
| 2002/0058971 A1 | 5/2002 | Zarinetchi et al. |
| 2002/0077572 A1 | 6/2002 | Fang et al. |
| 2002/0177884 A1 | 11/2002 | Ahn et al. |
| 2002/0188333 A1 | 12/2002 | Nowick et al. |
| 2003/0030342 A1 | 2/2003 | Chen et al. |
| 2003/0030593 A1 | 2/2003 | Tomomatsu et al. |
| 2003/0093128 A1 | 5/2003 | Freed et al. |
| 2003/0097165 A1 | 5/2003 | Krulevitch et al. |
| 2004/0064166 A1 | 4/2004 | Thompson et al. |
| 2004/0073272 A1 | 4/2004 | Knudson et al. |
| 2004/0098068 A1 | 5/2004 | Carbunaru et al. |
| 2004/0172104 A1 | 9/2004 | Berg et al. |
| 2004/0236387 A1 | 11/2004 | Fang et al. |
| 2005/0065553 A1 | 3/2005 | Ben Ezra et al. |
| 2005/0085874 A1 | 4/2005 | Davis et al. |
| 2005/0102006 A1 | 5/2005 | Whitehurst et al. |
| 2005/0177067 A1 | 8/2005 | Tracey et al. |
| 2005/0267547 A1 | 12/2005 | Knudson et al. |
| 2005/0288743 A1 | 12/2005 | Ahn et al. |
| 2006/0009816 A1 | 1/2006 | Fang et al. |
| 2006/0064140 A1 | 3/2006 | Whitehurst et al. |
| 2006/0090762 A1 | 5/2006 | Hegde et al. |
| 2006/0116739 A1 | 6/2006 | Betser et al. |
| 2006/0187049 A1* | 8/2006 | Moser ............... G06K 19/0701 340/572.5 |
| 2006/0190056 A1 | 8/2006 | Fowler et al. |
| 2006/0192628 A1 | 8/2006 | Schulman et al. |
| 2006/0270968 A1 | 11/2006 | Greenberg et al. |
| 2007/0004994 A1* | 1/2007 | Sherman ............... A61B 5/0031 602/26 |
| 2007/0055324 A1 | 3/2007 | Thompson et al. |
| 2007/0144535 A1 | 6/2007 | Hegde et al. |
| 2007/0205291 A1 | 9/2007 | Aramaki et al. |
| 2007/0233204 A1 | 10/2007 | Lima et al. |
| 2007/0261701 A1 | 11/2007 | Sanders |
| 2008/0021506 A1* | 1/2008 | Grocela ............... A61N 1/3601 607/9 |
| 2008/0046016 A1 | 2/2008 | Ben-David et al. |
| 2008/0047566 A1 | 2/2008 | Hegde et al. |
| 2008/0057179 A1 | 3/2008 | Greenberg et al. |
| 2008/0058898 A1 | 3/2008 | Greenberg et al. |
| 2008/0064946 A1 | 3/2008 | Greenberg et al. |
| 2008/0078411 A1 | 4/2008 | Buscemi et al. |
| 2008/0078412 A1 | 4/2008 | Buscemi et al. |
| 2008/0091241 A1 | 4/2008 | Ben-Ezra et al. |
| 2008/0091245 A1 | 4/2008 | Ben-Ezra et al. |
| 2008/0109045 A1 | 5/2008 | Gross et al. |
| 2008/0119898 A1 | 5/2008 | Ben-David et al. |
| 2008/0125819 A1 | 5/2008 | Ben-David et al. |
| 2008/0125827 A1 | 5/2008 | Ben-David et al. |
| 2008/0132964 A1 | 6/2008 | Cohen et al. |
| 2008/0147137 A1 | 6/2008 | Cohen et al. |
| 2008/0177351 A1 | 7/2008 | Fang et al. |
| 2008/0300657 A1 | 12/2008 | Stultz |
| 2009/0005845 A1 | 1/2009 | David et al. |
| 2009/0038623 A1 | 2/2009 | Farbarik et al. |
| 2009/0069866 A1 | 3/2009 | Farbarik et al. |
| 2009/0078275 A1 | 3/2009 | Hegde et al. |
| 2009/0173351 A1 | 7/2009 | Sahin et al. |
| 2009/0240314 A1 | 9/2009 | Kong et al. |
| 2010/0010603 A1 | 1/2010 | Ben-David et al. |
| 2010/0016929 A1 | 1/2010 | Prochazka |
| 2010/0063568 A1 | 3/2010 | Staunton et al. |
| 2010/0069994 A1 | 3/2010 | Cauller |
| 2010/0076524 A1* | 3/2010 | Forsberg ............... A61N 1/3787 607/61 |
| 2010/0106223 A1* | 4/2010 | Grevious ............... A61N 1/3787 607/60 |
| 2010/0131029 A1 | 5/2010 | Durand et al. |
| 2010/0152809 A1 | 6/2010 | Boggs, II |
| 2010/0164296 A1* | 7/2010 | Kurs ............... H01Q 1/248 307/104 |
| 2010/0174341 A1 | 7/2010 | Bolea et al. |
| 2010/0198103 A1 | 8/2010 | Meadows et al. |
| 2010/0217353 A1 | 8/2010 | Forsell |
| 2010/0241195 A1 | 9/2010 | Meadows et al. |
| 2010/0319711 A1 | 12/2010 | Hegde et al. |
| 2011/0009920 A1 | 1/2011 | Whitehurst et al. |
| 2011/0071591 A1 | 3/2011 | Bolea et al. |
| 2011/0112601 A1 | 5/2011 | Meadows et al. |
| 2011/0152706 A1 | 6/2011 | Christopherson et al. |
| 2011/0160794 A1 | 6/2011 | Bolea et al. |
| 2011/0172733 A1 | 7/2011 | Lima et al. |
| 2011/0190849 A1 | 8/2011 | Faltys et al. |
| 2011/0202119 A1 | 8/2011 | Ni et al. |
| 2011/0213438 A1 | 9/2011 | Lima et al. |
| 2011/0240037 A1 | 10/2011 | Hegde et al. |
| 2011/0245734 A1 | 10/2011 | Wagner et al. |
| 2011/0265322 A1 | 11/2011 | Greenberg et al. |
| 2011/0275927 A1 | 11/2011 | Wagner et al. |
| 2012/0022609 A1 | 1/2012 | Bolea et al. |
| 2012/0065701 A1 | 3/2012 | Cauller |
| 2012/0109020 A1 | 5/2012 | Wagner et al. |
| 2012/0192874 A1 | 8/2012 | Bolea et al. |
| 2012/0227748 A1 | 9/2012 | Sanders |
| 2012/0262108 A1* | 10/2012 | Olson ............... H02J 7/025 320/108 |
| 2012/0286582 A1 | 11/2012 | Kim et al. |
| 2012/0290055 A1 | 11/2012 | Boggs, II |
| 2012/0303080 A1 | 11/2012 | Ben-David et al. |
| 2013/0002423 A1 | 1/2013 | Robertson et al. |
| 2013/0110195 A1 | 5/2013 | Fletcher et al. |
| 2013/0116745 A1 | 5/2013 | Fletcher et al. |
| 2013/0165996 A1 | 6/2013 | Meadows et al. |
| 2013/0197615 A1 | 8/2013 | Rundle et al. |
| 2013/0213404 A1 | 8/2013 | Leibitzki et al. |
| 2013/0218251 A1 | 8/2013 | Penner |
| 2013/0238044 A1 | 9/2013 | Penner |
| 2013/0238066 A1 | 9/2013 | Boggs, II et al. |
| 2013/0274842 A1 | 10/2013 | Gaunt et al. |
| 2013/0338452 A1 | 12/2013 | Robertson et al. |
| 2014/0012342 A1 | 1/2014 | Penner et al. |
| 2014/0046407 A1 | 2/2014 | Ben-Ezra et al. |
| 2014/0058495 A1 | 2/2014 | Sakai et al. |
| 2014/0121741 A1 | 5/2014 | Bennett et al. |
| 2014/0152246 A1 | 6/2014 | Forsell |
| 2014/0155959 A1 | 6/2014 | Forsell |
| 2014/0163661 A1 | 6/2014 | Ben-David et al. |
| 2014/0207220 A1 | 7/2014 | Boling et al. |
| 2014/0214135 A1 | 7/2014 | Ben-David et al. |
| 2014/0249361 A1 | 9/2014 | DiUbaldi et al. |
| 2014/0323839 A1 | 10/2014 | McCreery |
| 2014/0330340 A1 | 11/2014 | Bennett et al. |
| 2014/0330356 A1 | 11/2014 | Bennett et al. |
| 2014/0378740 A1 | 12/2014 | Wagner et al. |
| 2015/0025613 A1 | 1/2015 | Nyberg, II et al. |
| 2015/0039055 A1 | 2/2015 | Wagner et al. |
| 2015/0039067 A1 | 2/2015 | Greenberg et al. |
| 2015/0051678 A1 | 2/2015 | Reed et al. |
| 2015/0066106 A1 | 3/2015 | Greenberg et al. |
| 2015/0105702 A1 | 4/2015 | Wagner et al. |
| 2015/0105840 A1 | 4/2015 | Boggs, II |
| 2015/0119629 A1 | 4/2015 | Wagner et al. |
| 2015/0134037 A1 | 5/2015 | Bennett et al. |
| 2015/0142075 A1 | 5/2015 | Miller, III et al. |
| 2015/0142120 A1 | 5/2015 | Papay |
| 2015/0148713 A1 | 5/2015 | Wagner et al. |
| 2015/0151123 A1 | 6/2015 | Wagner et al. |
| 2015/0174409 A1 | 6/2015 | Parker et al. |
| 2015/0264816 A1 | 9/2015 | Askin, III et al. |

(56) References Cited

U.S. PATENT DOCUMENTS

| | | |
|---|---|---|
| 2015/0321004 A1 | 11/2015 | Reed et al. |
| 2015/0321008 A1 | 11/2015 | Tesfayesus et al. |
| 2015/0321018 A1 | 11/2015 | Fletcher et al. |
| 2015/0328455 A1 | 11/2015 | Meadows et al. |
| 2015/0374985 A1 | 12/2015 | Fahey |
| 2015/0374998 A1 | 12/2015 | Fletcher et al. |
| 2016/0001079 A1 | 1/2016 | Fletcher et al. |
| 2016/0008608 A1 | 1/2016 | Boling et al. |
| 2016/0022481 A1 | 1/2016 | Fahey et al. |
| 2016/0030746 A1 | 2/2016 | Reed et al. |
| 2016/0059011 A1 | 3/2016 | Bolea et al. |
| 2016/0067396 A1 | 3/2016 | Stark et al. |
| 2016/0089540 A1 | 3/2016 | Bolea |
| 2016/0114174 A1 | 4/2016 | Colvin et al. |
| 2016/0114175 A1 | 4/2016 | Colvin et al. |
| 2016/0114177 A1 | 4/2016 | Colvin et al. |
| 2016/0135746 A1 | 5/2016 | Kumar et al. |
| 2016/0144180 A1 | 5/2016 | Simon et al. |
| 2017/0106190 A1 | 4/2017 | Papay |
| 2017/0274210 A1 | 9/2017 | Papay |
| 2017/0296815 A1 | 10/2017 | Papay |

FOREIGN PATENT DOCUMENTS

| | | |
|---|---|---|
| DE | 69529951 T2 | 2/2004 |
| DE | 69722782 T2 | 2/2004 |
| DE | 69629238 T2 | 5/2004 |
| DE | 69532514 T2 | 10/2004 |
| DE | 69730842 T2 | 9/2005 |
| DE | 69927438 T2 | 6/2006 |
| DE | 69928748 T2 | 6/2006 |
| DE | 69636883 T2 | 10/2007 |
| DE | 60315327 T2 | 1/2008 |
| DE | 69535686 T2 | 1/2009 |
| DE | 112008001669 T5 | 5/2010 |
| DE | 202007019439 U1 | 9/2012 |
| EP | 0702977 B1 | 3/1996 |
| EP | 0706808 B1 | 4/1996 |
| EP | 0743076 B1 | 11/1996 |
| EP | 0814868 B1 | 1/1998 |
| EP | 0970713 B1 | 1/2000 |
| EP | 0998328 B1 | 5/2000 |
| EP | 1052935 B1 | 11/2000 |
| EP | 1175919 B1 | 1/2002 |
| EP | 1277491 B1 | 1/2003 |
| EP | 1306104 B1 | 5/2003 |
| EP | 1331969 B1 | 8/2003 |
| EP | 1389079 B1 | 2/2004 |
| EP | 1429837 B1 | 6/2004 |
| EP | 1446188 B1 | 8/2004 |
| EP | 1494753 B1 | 1/2005 |
| EP | 1507473 B1 | 2/2005 |
| EP | 1524007 A1 | 4/2005 |
| EP | 1545693 B1 | 6/2005 |
| EP | 1554012 B1 | 7/2005 |
| EP | 1608432 B1 | 12/2005 |
| EP | 1609502 A1 | 12/2005 |
| EP | 1613396 B1 | 1/2006 |
| EP | 1648559 B1 | 4/2006 |
| EP | 1675648 B1 | 7/2006 |
| EP | 1676526 B1 | 7/2006 |
| EP | 1682222 B1 | 7/2006 |
| EP | 1706178 B1 | 10/2006 |
| EP | 1750801 B1 | 2/2007 |
| EP | 1776922 A1 | 4/2007 |
| EP | 1861162 B1 | 12/2007 |
| EP | 1874397 A2 | 1/2008 |
| EP | 1897586 B1 | 3/2008 |
| EP | 1904153 B1 | 4/2008 |
| EP | 1907048 A2 | 4/2008 |
| EP | 1981583 B1 | 10/2008 |
| EP | 1981589 B1 | 10/2008 |
| EP | 2036588 B1 | 3/2009 |
| EP | 2040790 B1 | 4/2009 |
| EP | 2089100 B1 | 8/2009 |
| EP | 2116274 B1 | 11/2009 |
| EP | 2143465 B1 | 1/2010 |
| EP | 2167187 A2 | 3/2010 |
| EP | 2228095 A3 | 9/2010 |
| EP | 2243509 A1 | 10/2010 |
| EP | 2266164 B1 | 12/2010 |
| EP | 2272562 A1 | 1/2011 |
| EP | 2286871 B1 | 2/2011 |
| EP | 2289596 B1 | 3/2011 |
| EP | 2298408 A2 | 3/2011 |
| EP | 2310088 B1 | 4/2011 |
| EP | 2318088 B1 | 5/2011 |
| EP | 2380625 A1 | 10/2011 |
| EP | 2383015 A1 | 11/2011 |
| EP | 2462982 A1 | 6/2012 |
| EP | 2468358 B1 | 6/2012 |
| EP | 2476458 B1 | 7/2012 |
| EP | 2478931 B1 | 7/2012 |
| EP | 2550992 B1 | 1/2013 |
| EP | 2462983 A1 | 6/2013 |
| EP | 2617396 A2 | 7/2013 |
| EP | 2617457 A2 | 7/2013 |
| EP | 2617460 A2 | 7/2013 |
| EP | 2667933 B1 | 12/2013 |
| EP | 2905051 A1 | 8/2015 |
| EP | 2907542 A1 | 8/2015 |
| EP | 2932998 A1 | 10/2015 |
| EP | 2965782 A1 | 1/2016 |
| EP | 3002035 A1 | 4/2016 |
| EP | 2211977 A1 | 6/2016 |
| EP | 3071288 B1 | 11/2018 |
| JP | 06-007724 Y | 3/1994 |
| JP | 11-195921 A | 7/1999 |
| JP | 2007-13662 | 1/2007 |
| JP | 2011-500143 A | 1/2011 |
| JP | 4953996 B | 3/2012 |
| WO | WO 96/40367 | 12/1996 |
| WO | WO 97/37720 | 10/1997 |
| WO | WO 97/49454 | 12/1997 |
| WO | WO 98/11942 | 3/1998 |
| WO | WO 98/24510 | 6/1998 |
| WO | WO 99/39769 | 8/1999 |
| WO | WO 99/62594 | 12/1999 |
| WO | WO 00/02212 | 1/2000 |
| WO | WO 00/24456 | 5/2000 |
| WO | WO 01/39830 | 6/2001 |
| WO | WO 01/78216 | 10/2001 |
| WO | WO 03/009749 | 2/2003 |
| WO | WO 03/061335 | 7/2003 |
| WO | WO 03/066153 | 8/2003 |
| WO | WO 03/099377 | 12/2003 |
| WO | WO 2004/002572 | 1/2004 |
| WO | WO 2004/008954 | 1/2004 |
| WO | WO 2004/028624 | 4/2004 |
| WO | WO 2004/064729 | 8/2004 |
| WO | WO 2004/103455 | 12/2004 |
| WO | WO 2004/110549 | 12/2004 |
| WO | WO 2004/110550 | 12/2004 |
| WO | WO 2005/011805 | 2/2005 |
| WO | WO 2005/037370 | 4/2005 |
| WO | WO 2005/077276 | 8/2005 |
| WO | WO 2005/082452 | 9/2005 |
| WO | WO 2006/093964 | 9/2006 |
| WO | WO 2006/132810 | 12/2006 |
| WO | WO 2007/035361 | 3/2007 |
| WO | WO 2007/035774 | 3/2007 |
| WO | WO 2007/081714 | 7/2007 |
| WO | WO 2007/090047 | 8/2007 |
| WO | WO 2007/092865 | 8/2007 |
| WO | WO 2007/098202 | 8/2007 |
| WO | WO 2007/120305 | 10/2007 |
| WO | WO 2007/149571 | 12/2007 |
| WO | WO 2008/005903 | 1/2008 |
| WO | WO 2008/014028 | 1/2008 |
| WO | WO 2008/016802 | 2/2008 |
| WO | WO 2008/039921 | 4/2008 |
| WO | WO 2008/042058 | 4/2008 |
| WO | WO 2008/048724 | 4/2008 |
| WO | WO 2008/079700 | 7/2008 |

(56) References Cited

FOREIGN PATENT DOCUMENTS

| | | |
|---|---|---|
| WO | WO 2008/076646 | 8/2008 |
| WO | WO 2009/032625 | 3/2009 |
| WO | WO 2009/046044 | 4/2009 |
| WO | WO 2009/048580 | 4/2009 |
| WO | WO 2009/051536 | 4/2009 |
| WO | WO 2009/051538 | 4/2009 |
| WO | WO 2009/051539 | 4/2009 |
| WO | WO 2009/061537 | 5/2009 |
| WO | WO 2009/070086 | 6/2009 |
| WO | WO 2009/111012 | 9/2009 |
| WO | WO 2009/126354 | 10/2009 |
| WO | WO 2009/140636 | 11/2009 |
| WO | WO 2010/003106 | 1/2010 |
| WO | WO 2010/039853 | 4/2010 |
| WO | WO 2010/042020 | 4/2010 |
| WO | WO 2010/042404 | 4/2010 |
| WO | WO 2010/096776 | 8/2010 |
| WO | WO 2011/060056 | 5/2011 |
| WO | WO 2011/139779 | 11/2011 |
| WO | WO 2011/143490 | 11/2011 |
| WO | WO 2012/030522 | 3/2012 |
| WO | WO 2012/055389 | 5/2012 |
| WO | WO 2013/067538 | 5/2013 |
| WO | WO 2013/078092 | 5/2013 |
| WO | WO 2013/086212 | 6/2013 |
| WO | WO 2013/147799 | 10/2013 |
| WO | WO 2013/173214 | 11/2013 |
| WO | WO 2013/188400 | 12/2013 |
| WO | WO 2014/004526 | 1/2014 |
| WO | WO 2014/0179685 | 11/2014 |

\* cited by examiner

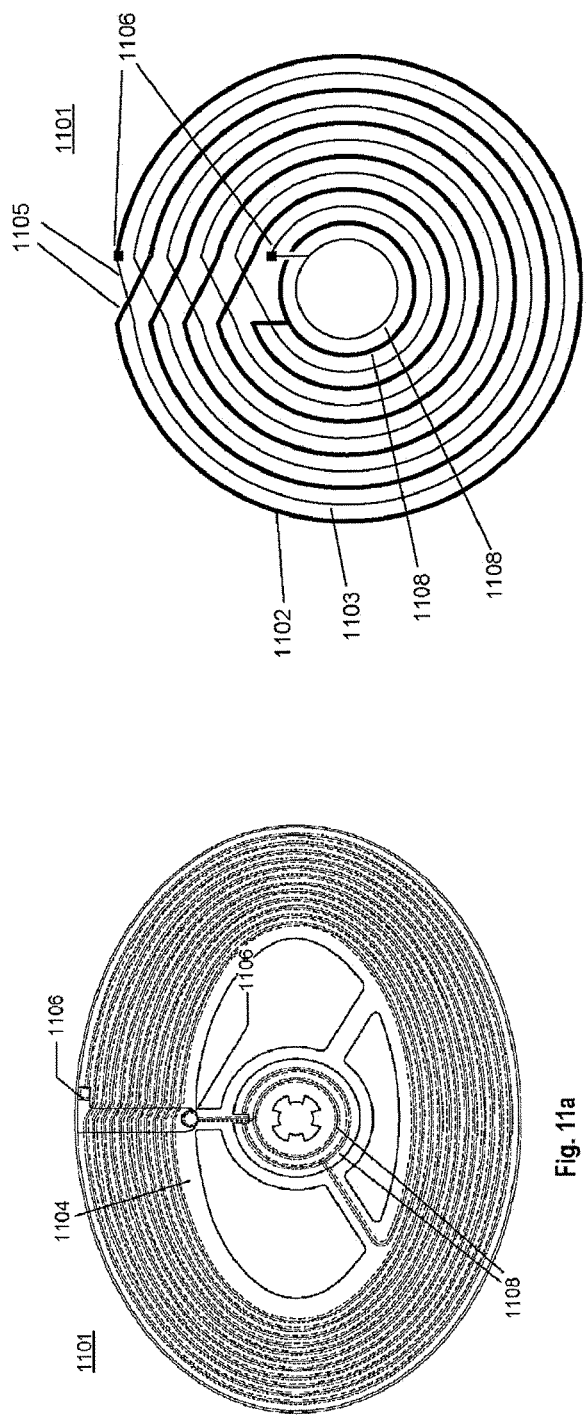
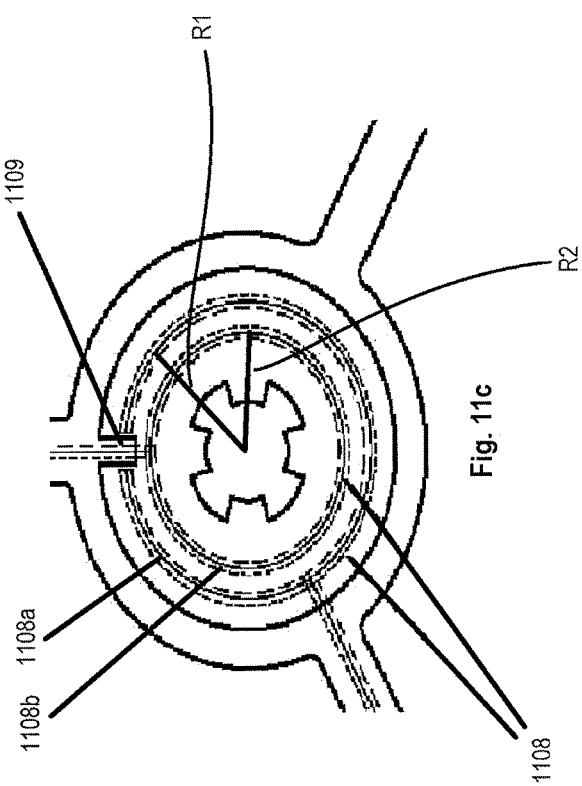
Fig. 11a
Fig. 11b
Fig. 11c

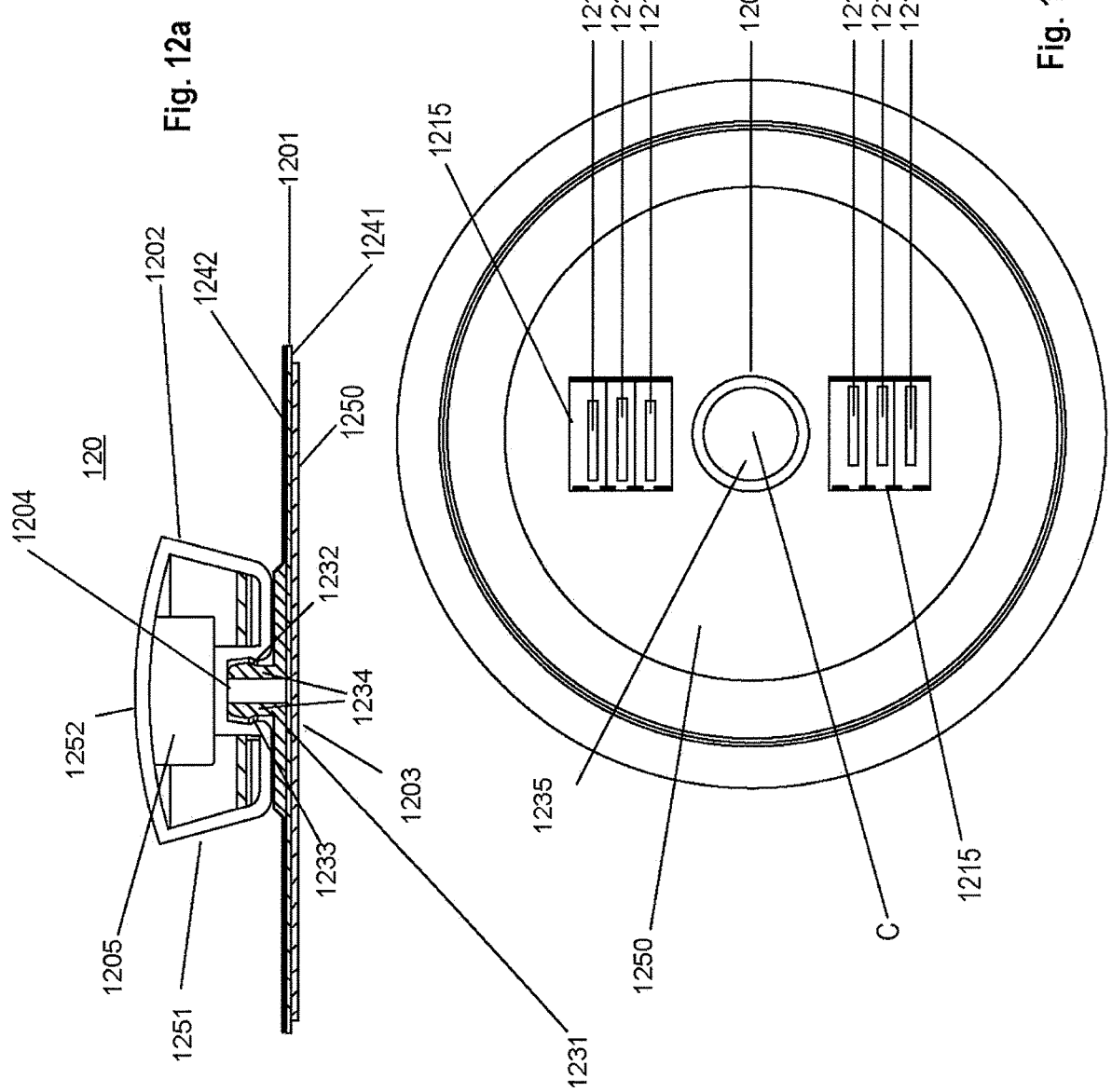

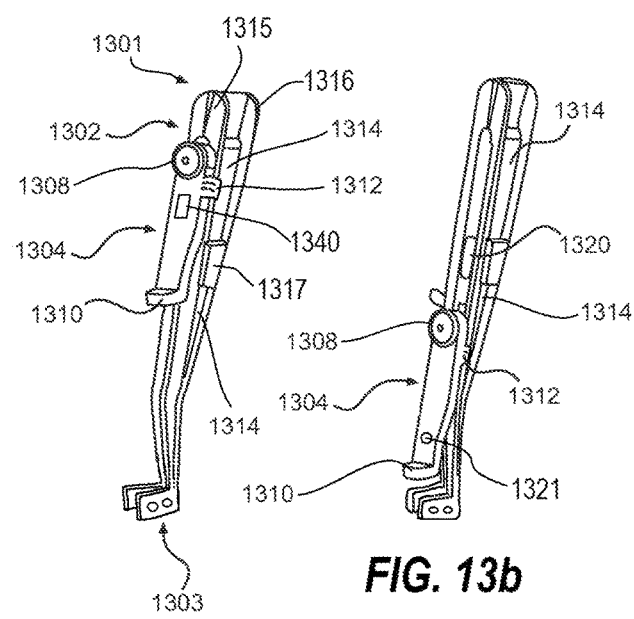
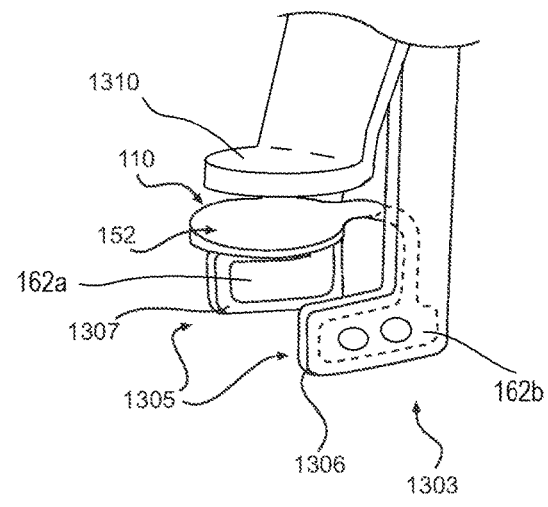
FIG. 13a
FIG. 13b
FIG. 13c

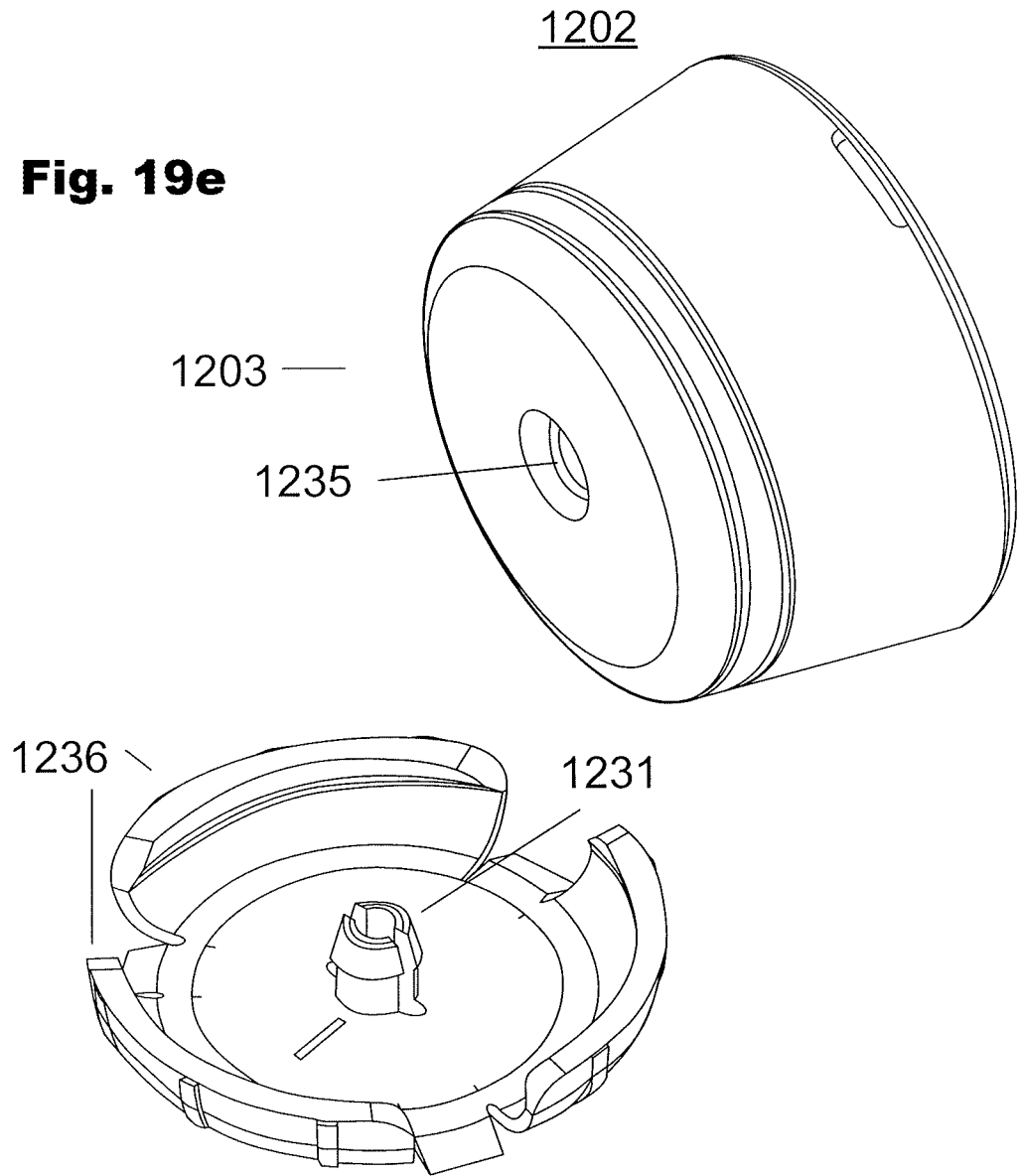

SLEEP DISORDERED BREATHING TREATMENT APPARATUS

RELATED APPLICATIONS

This application is a continuation-in-part application of application Ser. No. 14/059,632, filed on Oct. 22, 2013, now U.S. Pat. No. 9,855,032; application Ser. No. 14/322,877, filed on Jul. 2, 2014, now U.S. Pat. No. 9,327,132; application Ser. No. 14/519,663, filed on Oct. 21, 2014, now U.S. Pat. No. 9,393,435; application Ser. No. 13/951,590, filed on Jul. 26, 2013, now U.S. Pat. No. 9,031,653; application Ser. No. 14/496,212, filed Sep. 25, 2014, now U.S. Pat. No. 9,220,908; application Ser. No. 13/952,015, filed Jul. 26, 2013, now U.S. Pat. No. 9,555,257; application Ser. No. 13/952,063, filed Jul. 26, 2013, now U.S. Pat. No. 9,526,906; application Ser. No. 14/059,651, filed Jul. 26, 2013, now U.S. Pat. No. 9,504,828; application Ser. No. 13/952,152, filed Jul. 26, 2013, now U.S. Pat. No. 9,095,725; application Ser. No. 13/952,150, filed Jul. 26, 2013, now U.S. Pat. No. 10,918,376; application Ser. No. 13/952,143, filed Jul. 26, 2013, now U.S. Pat. No. 8,958,893; application Ser. No. 14/476,715, filed Sep. 3, 2014, now U.S. Pat. No. 9,220,907; and application Ser. No. 13/952,082, filed Jul. 26, 2013, now U.S. Pat. No. 9,511,238. Application Ser. No. 14/059,632 is a continuation of application Ser. No. 13/951,753, filed on Jul. 26, 2013, which claims the benefit of priority under 35 U.S.C. § 119(e) to U.S. Provisional Application No. 61/676,327, filed on Jul. 26, 2012. Application Ser. No. 14/322,877 is a divisional of application Ser. No. 13/951,606, filed on Jul. 26, 2013, now U.S. Pat. No. 8,812,135, issued on Aug. 19, 2014, which claims the benefit of priority under 35 U.S.C. § 119(e) to U.S. Provisional Application No. 61/676,327, filed on Jul. 26, 2012. Application Ser. No. 14/519,663 is a divisional of application Ser. No. 13/952,031, filed on Jul. 26, 2013, now U.S. Pat. No. 8,897,880, issued on Nov. 25, 2014, which claims the benefit of priority under 35 U.S.C. § 119(e) to U.S. Provisional Application No. 61/676,327, filed on Jul. 26, 2012. Application Ser. No. 13/951,590 claims the benefit of priority under 35 U.S.C. § 119(e) to U.S. Provisional Application No. 61/676,327, filed on Jul. 26, 2012. Application Ser. No. 14/4946,212 is a divisional application of application Ser. No. 13/951,856, filed on Jul. 26, 2013, now U.S. Pat. No. 8,903,515, issued on Dec. 2, 2014, which claims the benefit of priority under 35 U.S.C. § 119(e) to U.S. Provisional Application No. 61/676,327, filed on Jul. 26, 2012. Application Ser. No. 13/952,015 claims the benefit of priority under 35 U.S.C. § 119(e) to U.S. Provisional Application No. 61/676,327, filed on Jul. 26, 2012. Application Ser. No. 13/952,063 claims the benefit of priority under 35 U.S.C. § 119(e) to U.S. Provisional Application No. 61/676,327, filed on Jul. 26, 2012. Application Ser. No. 14/059,651 is a divisional application of application Ser. No. 13/952,027, filed on Jul. 26, 2013, now U.S. Pat. No. 8,948,871, issued on Feb. 3, 2015, which claims the benefit of priority under 35 U.S.C. § 119(e) to U.S. Provisional Application No. 61/676,327, filed on Jul. 26, 2012. Application Ser. No. 14/476,715 is a divisional application of application Ser. No. 13/952,106, filed on Jul. 26, 2013, now U.S. Pat. No. 8,838,256, issued on Sep. 16, 2014, which claims the benefit of priority under 35 U.S.C. § 119(e) to U.S. Provisional Application No. 61/676,327, filed on Jul. 26, 2012. Application Ser. No. 13/952,152 claims the benefit of priority under 35 U.S.C. § 119(e) to U.S. Provisional Application No. 61/676,327, filed on Jul. 26, 2012. Application Ser. No. 13/952,150 claims the benefit of priority under 35 U.S.C. § 119(e) to U.S. Provisional Application No. 61/676,327, filed on Jul. 26, 2012. Application Ser. No. 13/952,143 claims the benefit of priority under 35 U.S.C. § 119(e) to U.S. Provisional Application No. 61/676,327, filed on Jul. 26, 2012. Application Ser. No. 13/952,082 claims the benefit of priority under 35 U.S.C. § 119(e) to U.S. Provisional Application No. 61/676,327, filed on Jul. 26, 2012. All of the above referenced applications are incorporated herein by reference in their entirety.

TECHNICAL FIELD

Embodiments of the present disclosure generally relate to devices and methods for conveying power from a location external to a subject to a location within the subject. More particularly, embodiments of the present disclosure relate to devices and methods for transcutaneously conveying power to an implanted neuromodulation device.

BACKGROUND

Neural modulation presents the opportunity to treat many physiological conditions and disorders by interacting with the body's own natural neural processes. Neural modulation includes inhibition (e.g. blockage), stimulation, modification, regulation, or therapeutic alteration of activity, electrical or chemical, in the central, peripheral, or autonomic nervous system. By modulating the activity of the nervous system, for example through the stimulation of nerves or the blockage of nerve signals, several different goals may be achieved. Motor neurons may be stimulated at appropriate times to cause muscle contractions. Sensory neurons may be blocked, for instance to relieve pain, or stimulated, for instance to provide a signal to a subject. In other examples, modulation of the autonomic nervous system may be used to adjust various involuntary physiological parameters, such as heart rate and blood pressure. Neural modulation may provide the opportunity to treat several diseases or physiological conditions, a few examples of which are described in detail below.

Among the conditions to which neural modulation may be applied is sleep disordered breathing, examples of which include obstructive sleep apnea (OSA) and snoring. OSA is a respiratory disorder characterized by recurrent episodes of partial or complete obstruction of the upper airway during sleep. During the sleep of a person without OSA, the pharyngeal muscles relax during sleep and gradually collapse, narrowing the airway. The airway narrowing limits the effectiveness of the sleeper's breathing, causing a rise in $CO_2$ levels in the blood. The increase in $CO_2$ results in the pharyngeal muscles contracting to open the airway to restore proper breathing. The largest of the pharyngeal muscles responsible for upper airway dilation is the genioglossus muscle, which is one of several different muscles in the tongue. The genioglossus muscle is responsible for forward tongue movement and the stiffening of the anterior pharyngeal wall. In patients with OSA, the neuromuscular activity of the genioglossus muscle is decreased compared to normal individuals, accounting for insufficient response and contraction to open the airway as compared to a normal individual. This lack of response contributes to a partial or total airway obstruction, which significantly limits the effectiveness of the sleeper's breathing. In OSA patients, there are often several airway obstruction events during the night. Because of the obstruction, there is a gradual decrease of oxygen levels in the blood (hypoxemia). Hypoxemia leads to night time arousals, which may be registered by EEG, showing that the brain awakes from any stage of sleep to a short arousal. During the arousal, there is a conscious breath or gasp, which resolves the airway obstruction. An increase in sympathetic tone activity rate through the release of hormones such as epinephrine and noradrenaline also often occurs as a response to hypoxemia. As a result of the increase in sympathetic tone, the heart enlarges in an attempt to pump more blood and increase the blood pressure and heart rate, further arousing the patient. After the resolution of the apnea event, as the patient returns to sleep, the airway collapses again, leading to further arousals.

These repeated arousals, combined with repeated hypoxemia, leaves the patient sleep deprived, which leads to daytime somnolence and worsens cognitive function. This cycle can repeat itself up to hundreds of times per night in severe patients. Thus, the repeated fluctuations in and sympathetic tone and episodes of elevated blood pressure during the night evolve to high blood pressure through the entire day. Subsequently, high blood pressure and increased heart rate may cause other diseases.

Efforts for treating OSA include Continuous Positive Airway Pressure (CPAP) treatment, which requires the patient to wear a mask through which air is blown into the nostrils to keep the airway open. Other treatment options include the implantation of rigid inserts in the soft palate to provide structural support, tracheotomies, or tissue ablation.

Another condition to which neural modulation may be applied is the occurrence of migraine headaches. Pain sensation in the head is transmitted to the brain via the occipital nerve, specifically the greater occipital nerve, and the trigeminal nerve. When a subject experiences head pain, such as during a migraine headache, the inhibition of these nerves may serve to decrease or eliminate the sensation of pain.

Neural modulation may also be applied to hypertension. Blood pressure in the body is controlled via multiple feedback mechanisms. For example, baroreceptors in the carotid body in the carotid artery are sensitive to blood pressure changes within the carotid artery. The baroreceptors generate signals that are conducted to the brain via the glossopharyngeal nerve when blood pressure rises, signaling the brain to activate the body's regulation system to lower blood pressure, e.g. through changes to heart rate, and vasodilation/vasoconstriction. Conversely, parasympathetic nerve fibers on and around the renal arteries generate signals that are carried to the kidneys to initiate actions, such as salt retention and the release of angiotensin, which raise blood pressure. Modulating these nerves may provide the ability to exert some external control over blood pressure.

The foregoing are just a few examples of conditions to which neuromodulation may be of benefit, however embodiments of the invention described hereafter are not necessarily limited to treating only the above-described conditions.

SUMMARY

Some embodiments of the disclosure may include a device for wirelessly powering an implant unit in a body of a subject from a location outside of the body of the subject, wherein the implant unit includes a secondary antenna for wirelessly receiving energy. The device may include a primary antenna configured to be located external to a subject, a circuit electrically connected to the primary antenna and associated with a plurality of selectable capacitance values. The device may also include at least one processor configured to determine a transmission efficiency value between the primary antenna and the secondary antenna for each of a plurality of frequencies; and select a capacitance value to be included in the circuit, from among the plurality of selectable capacitance values, based on the determined transmission efficiencies.

Additional features of the disclosure will be set forth in part in the description that follows, and in part will be obvious from the description, or may be learned by practice of the disclosed embodiments.

It is to be understood that both the foregoing general description and the following detailed description are exemplary and explanatory only, and are not restrictive of the invention, as claimed.

BRIEF DESCRIPTION OF THE DRAWINGS

The accompanying drawings, which are incorporated in and constitute a part of this specification, illustrate several embodiments of the disclosure and, together with the description, serve to explain the principles of the embodiments disclosed herein.

FIGS. 11a, 11b, and 11c illustrate a double-layer crossover antenna.

FIGS. 12a and 12b illustrate an exemplary embodiment of an external unit.

FIGS. 13a-13c illustrate various aspects of a delivery tool.

FIGS. 19a-f illustrate several additional exemplary embodiments of structures for enabling selective mounting of a housing to a carrier.

DESCRIPTION OF EXEMPLARY EMBODIMENTS

Figure 1:
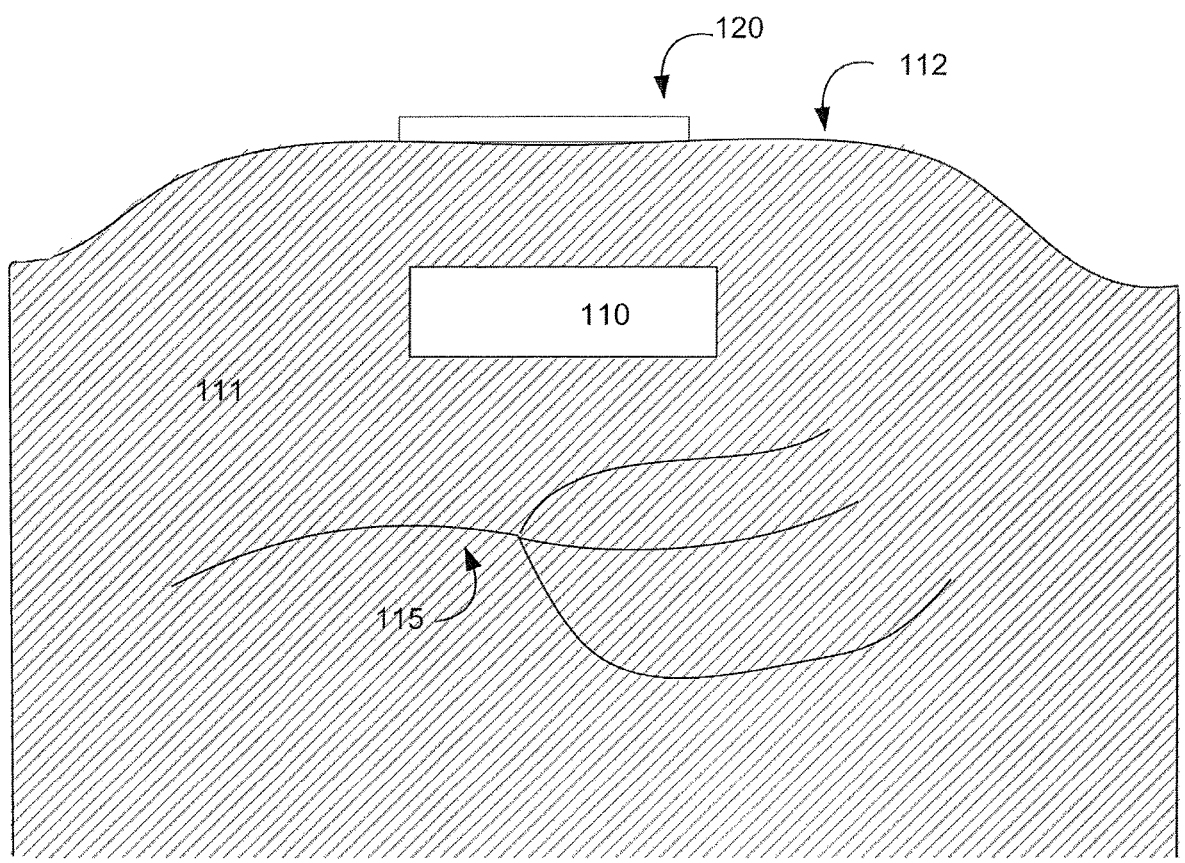
FIG. 1 diagrammatically illustrates an implant unit and external unit, according to exemplary embodiments of the present disclosure.

Reference will now be made in detail to exemplary embodiments of the present disclosure, examples of which are illustrated in the accompanying drawings. Wherever possible, the same reference numbers will be used throughout the drawings to refer to the same or like parts.

Some embodiments of the present disclosure relate to a device (also referred to as an external unit) having a primary antenna wirelessly powering an implantable device (also referred to as an implant unit) having a secondary antenna. When the two antennas are in resonant frequency match, the efficiency of energy transfer between the external unit and the implant unit may be higher than circumstances in which a resonant frequency associated with the primary antenna of the external unit does not match a resonant frequency associated with the secondary antenna of the implant unit. In some cases, however, the resonant frequency associated with the secondary antenna on the implant unit may change over time for a variety of reasons, including, for example, as a result of effects associated with implantation in the subject's body. The present disclosure describes embodiments configured to change or reduce a frequency mismatch between a resonant frequency associated with the secondary antenna of the implant unit and a resonant frequency associated with the primary antenna of the external unit.

The implantable device may be employed, for example, to modulate at least one nerve in the subject's body. Nerve modulation, or neural modulation, includes inhibition (e.g., blockage), stimulation, modification, regulation, or therapeutic alteration of activity, electrical or chemical, in the central, peripheral, or autonomic nervous system. Nerve modulation may take the form of nerve stimulation, which may include providing energy to the nerve to create a voltage change sufficient for the nerve to activate, or propagate an electrical signal of its own. Nerve modulation may also take the form of nerve inhibition, which may include providing energy to the nerve sufficient to prevent the nerve from propagating electrical signals. Nerve inhibition may be performed through the constant application of energy, and may also be performed through the application of enough energy to inhibit the function of the nerve for some time after the application. Other forms of neural modulation may modify the function of a nerve, causing a heightened or lessened degree of sensitivity. As referred to herein, modulation of a nerve may include modulation of an entire nerve and/or modulation of a portion of a nerve. For example, modulation of a motor neuron may be performed to affect only those portions of the neuron that are distal of the location to which energy is applied.

In patients with sleep disordered breathing, for example, a primary target response of nerve stimulation may include contraction of a tongue muscle (e.g., the muscle) in order to move the tongue to a position that does not block the patient's airway. In the treatment of migraine headaches, nerve inhibition may be used to reduce or eliminate the sensation of pain. In the treatment of hypertension, neural modulation may be used to increase, decrease, eliminate or otherwise modify nerve signals generated by the body to regulate blood pressure.

While embodiments of the present disclosure may be disclosed for use in patients with specific conditions, the embodiments may be used in conjunction with any patient/portion of a body where nerve modulation may be desired. That is, in addition to use in patients with sleep disordered breathing, migraine headaches, or hypertension, embodiments of the present disclosure may be use in many other areas, including, but not limited to: deep brain stimulation (e.g., treatment of epilepsy, Parkinson's, and depression); cardiac pace-making, stomach muscle stimulation (e.g., treatment of obesity), back pain, incontinence, menstrual pain, and/or any other condition that may be affected by neural modulation.

FIG. 1 illustrates an implant unit and external unit, according to an exemplary embodiment of the present disclosure. An implant unit 110, may be configured for implantation in a subject, in a location that permits it to modulate a nerve 115. The implant unit 110 may be located in a subject such that intervening tissue 111 exists between the implant unit 110 and the nerve 115. Intervening tissue may include muscle tissue, connective tissue, organ tissue, or any other type of biological tissue. Thus, location of implant unit 110 does not require contact with nerve 115 for effective neuromodulation. The implant unit 110 may also be located directly adjacent to nerve 115, such that no intervening tissue 111 exists. In further embodiments, the implant unit may be placed in conjunction with any nerve that one may desire to modulate. For example, modulation of the occipital nerve, the greater occipital nerve, and/or the trigeminal nerve may be useful for treating pain sensation in the head, such as that from migraines. Modulation of parasympathetic nerve fibers on and around the renal arteries (i.e., the renal nerves), the vagus nerve, and/or the glossopharyngeal nerve may be useful for treating hypertension. Additionally, any nerve of the peripheral nervous system (both spinal and cranial), including motor neurons, sensory neurons, sympathetic neurons and parasympathetic neurons, may be modulated to achieve a desired effect.

In treating sleep disordered breathing, implant unit 110 may be located on a genioglossus muscle of a patient. Such a location is suitable for modulation of the hypoglossal nerve, branches of which run inside the genioglossus muscle. For example, implant 110 may be configured to modulate terminal fibers of the hypoglossal nerve from a location spaced apart from (e.g., not contacting) the terminal fibers. Implant unit 110 may also be configured for placement in other locations. For example, migraine treatment may require subcutaneous implantation in the back of the neck, near the hairline of a subject, or behind the ear of a subject, to modulate the greater occipital nerve and/or the trigeminal nerve. Treating hypertension may require the implantation of a neuromodulation implant intravascularly inside the renal artery or renal vein (to modulate the parasympathetic renal nerves), either unilaterally or bilaterally, inside the carotid artery or jugular vein (to modulate the glossopharyngeal nerve through the carotid baroreceptors). Alternatively or additionally, treating hypertension may require the implantation of a neuromodulation implant subcutaneously, behind the ear or in the neck, for example, to directly modulate the glossopharyngeal nerve.

External unit 120 may be configured for location external to a patient, either directly contacting, or close to the skin 112 of the patient. External unit 120 may be configured to be affixed to the patient, for example, by adhering to the skin 112 of the patient, or through a band or other device configured to hold external unit 120 in place. Adherence to the skin of external unit 120 may occur such that it is in the vicinity of the location of implant unit 110.

Figure 2:
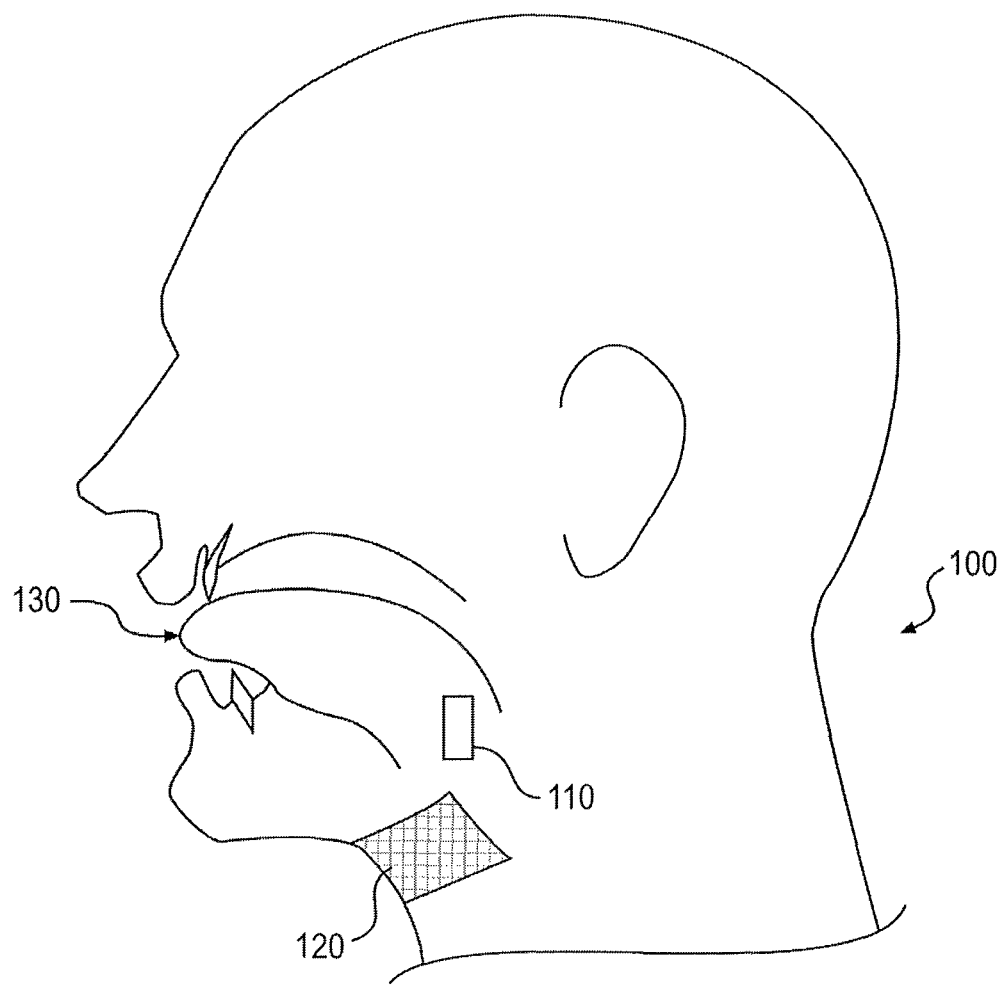
FIG. 2 is a partially cross-sectioned side view of a subject with an implant unit and external unit, according to exemplary embodiments of the present disclosure.

FIG. 2 illustrates an exemplary embodiment of a neuromodulation system for delivering energy in a patient 100 with sleep disordered breathing. The system may include an external unit 120 that may be configured for location external to the patient. In some embodiments of the present disclosure, external unit 120 may include devices for conveying power from a location external to a subject to a location within a subject. For example, external unit 120 may include a carrier and an electronics housing, each configured as a portion of a system to convey power to implant unit 110, located within the subject.

As illustrated in FIG. 2, external unit 120 may be configured to be affixed to the patient 100. FIG. 2 illustrates that in a patient 100 with sleep disordered breathing, the external unit 120 may be configured for placement underneath the patient's chin and/or on the front of patient's neck. In some embodiments, external unit 120 may be positioned at a location on the patient's skin opposite to a location of terminal fibers of the hypoglossal nerve. The suitability of placement locations may be determined by communication between external unit 120 and implant unit 110, discussed in greater detail below. In alternate embodiments, for the treatment of conditions other than sleep disordered breathing, the external unit may be configured to be affixed anywhere suitable on a patient, such as the back of a patient's neck, i.e. for communication with a migraine treatment implant unit, on the outer portion of a patient's abdomen, i.e. for communication with a stomach modulating implant unit, on a patient's back, i.e. for communication with a renal artery modulating implant unit, and/or on any other suitable external location on a patient's skin, depending on the requirements of a particular application.

External unit 120 may further be configured to be affixed to an alternative location proximate to the patient. For example, in one embodiment, the external unit may be configured to fixedly or removably adhere to a strap or a band that may be configured to wrap around a part of a patient's body. Alternatively, or in addition, the external unit may be configured to remain in a desired location external to the patient's body without adhering to that location.

The external unit 120 may include a housing and a carrier. The housing may include any suitable container configured for retaining components. In addition, while the external unit is illustrated schematically in FIG. 2, the housing may be any suitable size and/or shape and may be rigid or flexible. Non-limiting examples of housings for the external unit 120 include one or more of patches, buttons, or other receptacles having varying shapes and dimensions and constructed of any suitable material. The carrier may include any type of substrate, rigid or flexible, to which the housing may be mounted. In one embodiment, for example, the carrier may include a flexible material such that external unit 120 may be configured to conform to a desired location. For example, as illustrated in FIG. 2, the carrier may include a skin patch, which, in turn, may include a flexible substrate. The material of the flexible substrate may include, but is not limited to, plastic, silicone, woven natural fibers, and other suitable polymers, copolymers, and combinations thereof. Any portion of external unit 120 may be flexible or rigid, depending on the requirements of a particular application.

As previously discussed, in some embodiments external unit 120 may be configured to adhere to a desired location. Accordingly, in some embodiments, at least one side of the carrier may include an adhesive material. The adhesive material may include a biocompatible material and may allow for a patient to adhere the external unit to the desired location and remove the external unit upon completion of use. The adhesive may be configured for single or multiple uses of the external unit. Suitable adhesive materials may include, but are not limited to biocompatible glues, starches, elastomers, thermoplastics, and emulsions.

Figure 3:
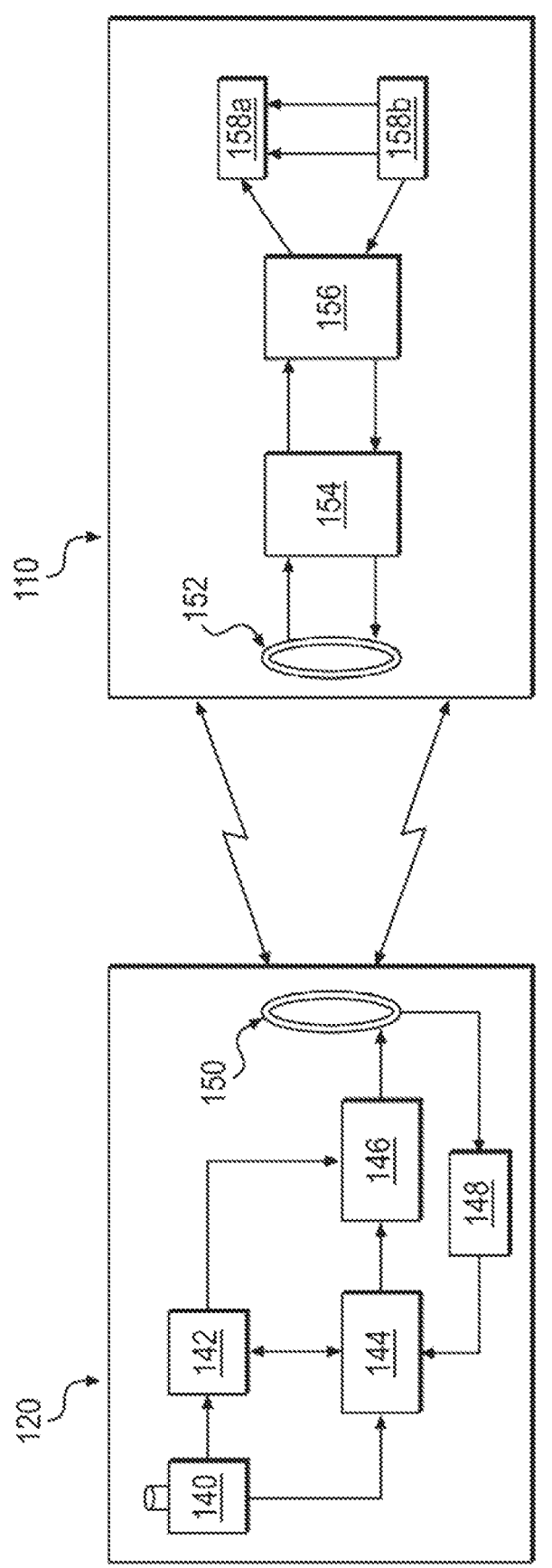
FIG. 3 illustrates a system including an implant unit and an external unit, according to exemplary embodiments of the present disclosure.

FIG. 3 is a diagrammatic representation of an exemplary device (e.g., external unit 120) and exemplary implantable unit (e.g., implant unit 110). In one embodiment, implant unit 110 may comprise a carrier (e.g., flexible carrier 161 illustrated in FIG. 4), an implantable circuit (e.g., circuit 180 illustrated in FIG. 6), an antenna (e.g., secondary antenna 152), and at least one component for receiving energy from the implantable circuit (e.g., implant electrodes 158a, 158b). Prior to implantation in the subject's body, the implantable circuit and the secondary antenna provide a certain resonant frequency. When implanted in the body of the subject, however, this resonant frequency may change due, for example, to various effects associated with locating the implant unit into the body of the subject. In some embodiments, the changes to the resonant frequency associated with the implant unit after implantation may be known, predictable, or predicted, etc. To account for this change in resonant frequency (or resonant frequency drift), the implant unit may be manufactured to have a resonant frequency associated with the antenna and implantable circuit that is mismatched from a resonant frequency of an external circuit (e.g., circuit 170) configured to communicate with the implantable circuit of the implant unit. This resonant frequency mismatch may be eliminated after the implant unit is placed in the body of the subject and changes in the resonant frequency associated with the implant unit occur. In some embodiments, internal unit 110 may be configured as a unit to be implanted into the body of a patient, and external unit 120 may be configured to send signals to and/or receive signals from implant unit 110.

As shown in FIG. 3, various components may be included within a housing of external unit 120 or otherwise associated with external unit 120. As illustrated in FIG. 3, at least one processor 144 may be associated with external unit 120. For example, the at least one processor 144 may be located within the housing of external unit 120. In alternative embodiments, the at least one processor 144 may be configured for wired or wireless communication with the external unit from a location external to the housing.

The at least one processor 144 may include any electric circuit that may be configured to perform a logic operation on at least one input variable. The at least one processor 144 may therefore include one or more integrated circuits, microchips, microcontrollers, and microprocessors, which may be all or part of a central processing unit (CPU), a digital signal processor (DSP), a field programmable gate array (FPGA), or any other circuit known to those skilled in the art that may be suitable for executing instructions or performing logic operations.

FIG. 3 illustrates that the external unit 120 may further be associated with a power source 140. The power source may be removably couplable to the external unit 120 at an exterior location relative to external unit 120. Alternatively, as shown in FIG. 3, power source 140 may be permanently or removably coupled to a location within external unit 120. The power source may further include any suitable source of power configured to be in electrical communication with the processor. In one embodiment, for example the power source 140 may include a battery.

The power source may be configured to power various components within the external unit. As illustrated in FIG. 3, power source 140 may be configured to provide power to the processor 144. In addition, the power source 140 may be configured to provide power to a signal source 142 and a feedback circuit 148. The signal source 142 may be in communication with the processor 144 and may include any device configured to generate a signal (e.g., a sinusoidal signal, square wave, triangle wave, microwave, radio-frequency (RF) signal, or any other type of electromagnetic signal). Signal source 142 may include, but is not limited to, a waveform generator that may be configured to generate alternating current (AC) signals and/or direct current (DC) signals. In one embodiment, for example, signal source 142 may be configured to generate an AC signal for transmission to one or more other components. Signal source 142 may be configured to generate a signal of any suitable frequency. In some embodiments, signal source 142 may be configured to generate a signal having a frequency of from about 6.5 MHz to about 13.6 MHz. In additional embodiments, signal source 142 may be configured to generate a signal having a frequency of from about 7.4 to about 8.8 MHz. In further embodiments, signal source 142 may generate a signal having a frequency as low as 90 kHz or as high as 28 MHz.

Signal source 142 may be configured for direct or indirect electrical communication with an amplifier 146. The amplifier may include any suitable device configured to amplify one or more signals generated from signal source 142. Amplifier 146 may include one or more of various types of amplification devices, including, for example, transistor based devices, operational amplifiers, RF amplifiers, power amplifiers, or any other type of device that can increase the gain associated with one or more aspects of a signal. The amplifier may further be configured to output the amplified signals to one or more components within external unit 120.

Feedback circuit 148, as shown in FIG. 3, may be in communication with various components of external unit 120. For example, feedback circuit 148 may be in direct or indirect electrical contact with processor 144 and a primary antenna 150. In some embodiments, feedback circuit 148 may include, for example, a signal analyzer or a detector.

The external unit 120 may additionally include a primary antenna 150. The primary antenna 150. As shown in FIG. 2, primary antenna 150 may be configured as part of a circuit within external unit 120 and may be coupled either directly or indirectly to various components in external unit 120. For example, as shown in FIG. 3, primary antenna 150 may be configured for communication with the amplifier 146.

The primary antenna 150 may include any conductive structure that may be configured to create an electromagnetic field. The primary antenna 150 may further be of any suitable size, shape, and/or configuration. The size, shape, and/or configuration may be determined by the size of the patient, the placement location of the implant unit, the size and/or shape of the implant unit, the amount of energy required to modulate a nerve, a location of a nerve to be modulated, the type of receiving electronics present on the implant unit, etc. The primary antenna 150 may include any suitable antenna known to those skilled in the art that may be configured to send and/or receive signals. Suitable antennas may include, but are not limited to, a long-wire antenna, a patch antenna, a helical antenna, etc. In one embodiment, for example, as illustrated in FIG. 3, primary antenna 150 may include a coil of electrically conductive material. Such a coil may be made from any suitable electrically conductive material and may be configured to include any suitable arrangement of conductive coils (e.g., diameter, number of coils, layout of coils, etc.). A coil antenna suitable for use as primary antenna 150 may have a diameter of between about 1 cm and 10 cm, and may be circular or oval shaped. In some embodiments, a coil antenna may have a diameter between 5 cm and 7 cm, and may be oval shaped. A coil antenna suitable for use as primary antenna 150 may have any number of windings, e.g. 4, 8, 12, or more. A coil antenna suitable for use as primary antenna 150 may have a wire diameter between about 0.01 mm and 2 mm. These antenna parameters are exemplary only, and may be adjusted above or below the ranges given to achieve suitable results.

As noted, implant unit 110 may be configured to be implanted in a patient's body (e.g., beneath the patient's skin). FIG. 2 illustrates that the implant unit 110 may be configured to be implanted for modulation of a nerve associated with a muscle of the subject's tongue 130. Modulating a nerve associated with a muscle of the subject's tongue 130 may include stimulation to cause a muscle contraction. In further embodiments, the implant unit 110 may be configured to be placed in conjunction with any nerve that one may desire to modulate. For example, modulation of the occipital nerve, the greater occipital nerve, and/or the trigeminal nerve may be useful for treating pain sensation in the head, such as that from migraines. Modulation of parasympathetic nerve fibers on and around the renal arteries (i.e. the renal nerves), the vagus nerve, and/or the glossopharyngeal nerve may be useful for treating hypertension. Additionally, any nerve of the peripheral nervous system (both spinal and cranial), including motor neurons, sensory neurons, sympathetic neurons and parasympathetic neurons, may be modulated to achieve a desired effect.

Implant unit 110 may be formed of any materials suitable for implantation into the body of a patient. In some embodiments, implant unit 110 may include a flexible carrier 161 (FIG. 4) including a flexible, biocompatible material. Such materials may include, for example, silicone, polyimides, phenyltrimethoxysilane (PTMS), polymethyl methacrylate (PMMA), Parylene C, polyimide, liquid polyimide, laminated polyimide, black epoxy, polyether ether ketone (PEEK), Liquid Crystal Polymer (LCP), Kapton, etc. Implant unit 110 may further include circuitry including conductive materials, such as gold, platinum, titanium, or any other biocompatible conductive material or combination of materials. Implant unit 110 and flexible carrier 161 may also be fabricated with a thickness suitable for implantation under a patient's skin. Implant 110 may have thickness of less than about 4 mm or less than about 2 mm.

Other components that may be included in or otherwise associated with the implant unit are illustrated in FIG. 3. For example, implant unit 110 may include a secondary antenna 152 mounted onto or integrated with flexible carrier 161. Similar to the primary antenna, the secondary antenna may include any suitable antenna known to those skilled in the art that may be configured to send and/or receive signals. The secondary antenna may include any suitable size, shape, and/or configuration. The size, shape and/or configuration may be determined by the size of the patient, the placement location of the implant unit 110, the amount of energy required to modulate the nerve, etc. Suitable antennas may include, but are not limited to, a long-wire antenna, a patch antenna, a helical antenna, etc. In some embodiments, for example, secondary antenna 152 may include a coil antenna having a circular shape (see also FIG. 4) or oval shape. Such a coil antenna may be made from any suitable conductive material and may be configured to include any suitable arrangement of conductive coils (e.g., diameter, number of coils, layout of coils, etc.). A coil antenna suitable for use as secondary antenna 152 may have a diameter of between about 5 mm and 30 mm, and may be circular or oval shaped. A coil antenna suitable for use as secondary antenna 152 may have any number of windings, e.g. 4, 15, 20, 30, or 50. A coil antenna suitable for use as secondary antenna 152 may have a wire diameter between about 0.001 mm and 1 mm. These antenna parameters are exemplary only, and may be adjusted above or below the ranges given to achieve suitable results.

FIGS. 11a and 11b illustrate a double-layer crossover antenna 1101 suitable for use as either primary antenna 150. While the double-layer crossover antenna 1101 illustrated in FIGS. 4a and 4b includes features making it suitable for use as a primary antenna 150, some or all of the features of the double-layer crossover antenna, as described below, may also be utilized in a secondary antenna 152. While a double-layer crossover antenna is shown and described, other antenna configurations may also be suitable for primary antenna 150 and/or secondary antenna 152. For example, single layer antennas may be used where antenna components (e.g., coils) are arranged in a single layer, e.g., either on or within a dielectric or insulating material. Also, while a crossover pattern is shown, other patterns may also be suitable. For example, in some embodiments, a wire associated with primary antenna 150 and/or secondary antenna 152 may include a pattern of traces of progressively decreasing dimension. In the case of traces arranged in coils, for example, each loop could include rings of progressively decreasing diameter to create a pattern that spirals inwardly. A similar approach may be viable using traces of other shapes as well.

Returning to FIG. 11a, this figure illustrates a single coil of double-layer crossover antenna 1101, while FIG. 11b illustrates two layers of double layer crossover antenna 1101. Antenna 1101 may include a first coil of wire 1102 arranged on a first side of a dielectric carrier 1104 and a second coil of wire 1103 on a second side of a dielectric carrier 1104.

Arranging the antenna coils in a double layer may serve to increase the transmission range of the antenna without increasing the size of the antenna. Such an arrangement, however, may also serve to increase capacitance between the wires of each coil. In each wire coil, an amount of parasitic capacitance between wires may partially depend on the distance each wire is from its neighbor. In a single layer coil, capacitance may be generated between each loop of the coil and its neighbors to either side. Thus, more compact coils may generate more parasitic capacitance. When a second layer coil is added, additional capacitance may then be generated between the wires of the first coil and the wires of the second coil. This additional capacitance may be further increased if corresponding loops of the first and second coils have the same or similar diameters, and/or if a dielectric carrier separating the loops is made very thin. Increased parasitic capacitance in an antenna may serve to alter characteristics, such as resonant frequency, of the antenna in unpredictable amounts based on manufacturing specifications. Additionally, resonant frequency drift, caused, for example by moisture incursion or antenna flexing, may be increased by the presence of increased parasitic capacitance. Thus, in order to decrease variability in the manufactured product, it may be advantageous to reduce the levels of parasitic capacitance in a dual layer antenna.

FIG. 11b illustrates a double layer crossover antenna 1101 which may exhibit a parasitic capacitance in a manufactured antenna lower than single layer counterparts. As illustrated in FIG. 11b, a first coil of wire 1102 is concentrically offset from a second coil of wire 1103. In contrast to a configuration where each loop of a first coil 1102 has the same diameter as corresponding loop of the second coil 1103, concentrically offsetting corresponding loops of each wire coil serves to increase the distance between a single loop of the first coil 1102 with a corresponding loop of the second coil 1103. This increased distance, in turn, may decrease the parasitic wire-to-wire capacitance between loops of first coil 1102 and corresponding loops of second coil 1103. This configuration may be particularly advantageous in reducing parasitic capacitance in a situation where a dielectric carrier 1104 is thin enough such that the concentric distance by which each coil is offset is relatively large compared to the thickness of the dielectric carrier 1104. For example, in a situation where a dielectric carrier is 0.5 mm thick, a concentric offset of 0.5 mm or more may produce a large change in parasitic capacitance. In contrast, in a situation where a dielectric carrier is 5 mm thick, a concentric offset of 0.5 mm may produce a smaller change in parasitic capacitance. The concentric offset between a first coil 1102 and a second coil 1103 may be achieved, for example, by a plurality of electrical trace steps 1105 that offset each loop of the coils from each preceding loop. Electrical trace steps 1105 on a first side of dielectric carrier 1104 cross over electrical trace steps 1105 on a second side of dielectric carrier 1104, thus providing the crossover feature of double-layer crossover antenna 1101.

In additional embodiments, double layer crossover antenna 1101 may include openings 1106 in dielectric carrier 1104 to facilitate the electrical connection of first and second coils 1102, 1103. First and second coils 1102, 1103 of double layer crossover antenna 1101 may also include exposed electrical portions 1108, 1109 configured to electrically connect with an electrical connector of a device housing that may be coupled to antenna 1101. Exposed electrical portions 1108, 1109 may be configured so as to maintain electrical contact with the electrical connector of a device housing independent of the axial orientation of the connection. As shown in FIG. 11c, exposed electrical portions 1108 may be configured in a pattern suitable for maintaining electrical contact with corresponding electrodes on an external unit 120, for example. In some embodiments, exposed electrical portions 1108 may be arranged in or may comprise continuous or discontinuous patterns of conductive material associated with carrier 1104. For example, exposed electrical portions 1108 may be arranged in continuous or discontinuous circles, ellipses, polygons, or any other suitable shape. In some embodiments, exposed electrical portions 1108 may include a first exposed electrical portion 1108a, forming a discontinuous circle, and a second exposed electrical portion 1108b, forming a continuous circle and located inside first exposed electrical portion 1108a. In some embodiments, first electrical portions 1108a may form an arc shape. Exposed electrical portion 1108 may include a plurality of first and second electrical portions 1108a, 1108b (respectively), for example, 1, 2, 4, or 5 of each. Additionally, exposed electrical portion 1108 may include an unequal number of first exposed electrical portions 1108a and second exposed electrical portions 1108b. For example, a greater number of first exposed electrical portions 1108a may be included as compared to second exposed electrical portions 1108b.

First exposed electrical portion 1108a may form a C-shape or U-shape configuration, providing a space 1109 between open ends. As shown in FIG. 11c, space 1109 may be configured for an electrical trace to pass through without contacting first exposed electrical portion 1108a. For example, space 1109 may allow the electrical trace to connect with second exposed electrical portion 1108b, or to other electrical components located within the circle of first exposed electrical portion 1108a.

FIG. 11c illustrates an exposed electrical portion 1108 with substantially circular first and second exposed electrical portions 1108a, 1108b. However, it is further contemplated that other shapes may be utilized, for example, elliptical, triangular, square, etc. Additionally, although antenna 1101 is shown in FIG. 11a with substantially elliptical coils, other shapes, such as circular, triangular, square, etc., may be also be used in different embodiments. Elliptical coils may facilitate placement of external unit 120 in certain areas (e.g., under the chin of a subject) while maintaining desirable electrical performance characteristics. FIGS. 12a and 12b illustrate an exemplary embodiment of external unit 120, including features that may be found in any combination in other embodiments. FIG. 12a illustrates a side view of external unit 120, depicting carrier 1201 and electronics housing 1202.

Housing 1202 may be configured to contain various electrical and mechanical components, as further discussed below with respect to FIG. 12a. Housing 1202 may include a bottom surface 1250, a top surface 1252, and at least one sidewall 1251. When configured in a generally cylindrical arrangement, sidewall 1251 may include a continuous surface. Bottom surface 1250 may be configured to directly contact carrier 1201 or various contacts may be included on bottom surface 1250 to interact with carrier 1201.

Carrier 1201 may include a skin patch configured for adherence to the skin of a subject, and having a first side 1241 and a second side 1242. Carrier 1201 may be flexible or rigid, or may have flexible portions and rigid portions. A securing element 1250 may be disposed on the first side 1241 of carrier 1201. Securing element 1250 may include a chemical-based agent (e.g., an adhesive material) or mechanical structures configured to secure carrier 1201 to a patient (e.g., to the patient's skin). In some embodiments, securing element 1240 may include an adhesive, a bonding material, a strap, or any suitable fastener. As shown in FIG. 12a, securing element 150 may be disposed along the entire length of first side 1241 or along a portion of first side. For example, securing element 1250 may only be disposed along flexible portions of carrier 1201.

Carrier 1201 and may include primary antenna 150, for example, a double-layer crossover antenna 1101 such as that illustrated in FIGS. 11a and 11b. Carrier 1201 may also include power source 140, such as a paper battery, thin film battery, or other type of substantially flat and/or flexible battery. Carrier 1201 may also include any other type of battery or power source.

Carrier 1201 may also include a connector 1203 configured for selectively or removably connecting carrier 1201 to electronics housing 1202. Connector 1203 may include a mechanical or electrical connection. For example, connector 1203 may include a protrusion extending or protruding away from second side 1242. As shown in FIG. 12a, connector 1203 may form a rod-like extension 1234 configured to mate with a receiver 1204 in electronics housing 1202. Receiver 1204 may include a recess or depression in electronics housing 1202. In some embodiments, connector 1203 and receive 1204 may form an interference fit. One or more detents 1232 on connector 1203 may engage one or more detent engagement portions 1233 on electronics housing 1202 to secure connector 1203 to electronics housing 1202. Alternatively, connector 1203 may form a recess, for example opening 1235 as shown in FIG. 12b. Opening 1235 may be configured to engage one or more securing means on electronics housing 1202 to secure carrier 1201 to electronics housing.

Connector 1203 may include various configurations. For example, connector 1203 may include a rodlike element 1231. Rodlike element 1231 may include any elongated structure of any cross-section. For example, rodlike element 1231 may be circular or oval in cross section, or may include a square or other-sided polygonal cross-section. Rodlike element 1231 may include a single integral protrusion, or may consist of several discrete protrusions grouped together to form rodlike element 1231. Such discrete portions may include flexible arms 1234. Connector 1203 may further include a detent portion 1232, for example, a notch or tab configured to engage with a corresponding detent engagement portion 1233 disposed on receiver 1204. Detent engagement portion may be, for example, a lip, rim, or flange. In some embodiments, detent portion 1232 may be disposed on flexible arms 1234, configured to elastically bend to permit engagement with receiver 1204 and return to their original positions to retain electronics housing 1202 in a mounted configuration. In some embodiments, connector 1203 may include a bayonet connector. In additional embodiments, connector 1203 may include a twist-lock connector. In some embodiments, connector 1203 may include various combinations of the above described retention features.

In further embodiments, connector 1203 may Connector 1203 may include various configurations and dimensions. For example, connector 1203 may be configured as a non-pouch connector, configured to provide a selective connection to electronics housing 1204 without the substantial use of concave feature. Connector 1203 may include, for example a peg, and may have flexible arms. Connector 1203 may further include a magnetic connection, a velcro connection, and/or a snap dome connection. Connector 1203 may also include a locating feature, configured to locate electronics housing 1202 at a specific height, axial location, and/or axial orientation with respect to carrier 1201. A locating feature of connector 1203 may further include pegs, rings, boxes, ellipses, bumps, etc.

Connector 1203 may be centered on carrier 1201, may be offset from the center by a predetermined amount, or may be provided at any other suitable location of carrier 1201. Multiple connectors 1203 may be provided on carrier 1201. Additionally, connector 1203 may be removable from electronics housing. In some embodiments, connector 1203 may be configured such that removal from electronics housing 1202 may cause breakage of connector 1203. This may prevent re-use of carrier 1201, which may be desirable when carrier 1201 loses efficacy through continued use.

Receiver 1204 may also include various configurations to facilitate the retention of mechanical connector 1203. For example, in the embodiment illustrated in FIGS. 12a and 12b, receiver 1204 may include an opening into which mechanical connector 1203 extends. The opening may be a concavity 1235, configured to receive and retain connector 1203. The concavity may include a rim portion, extending around at least a portion of the perimeter of the interior of the cavity, and configured to engage a detent portion 1232 of connector 1203. Alternative embodiments or receiver 1204 and connector 1203 are described below with respect to FIGS. 19a-f.

As illustrated in FIG. 12a, when a user mounts housing 1202 to carrier 1201, housing 1202 may be retained by connector 1203 in a manner in which at least a portion of a sidewall 1251 and a top surface 1252 of the housing is exposed when mounted to the carrier. The exposure of a portion of a sidewall 1251 and a top surface 1252 of the housing may permit a user to easily grasp housing 1202, to facilitate mounting and/or removal from carrier 1201. In alternative embodiments, wherein housing 1202 is mounted to carrier 1201 via engagement with a receiver 1204 disposed at a perimeter of housing 1202, connector 1203 may engage with receiver 1204 at portions of the perimeter, thereby leaving at least top surface 1252 exposed.

Electronics housing 1202 is illustrated in side view in FIG. 12*a* and in a bottom view in FIG. 12*b*. Electronics housing 1202 may be disposed on second side 1242 of carrier 1201, and may include electronics portion 1205, which may be arranged inside electronics housing 1202 in any manner that is suitable. Electronics portion 1205 may include various components, further discussed below, of external unit 120. For example, electronics portion 1205 may include any combination of at least one processor 144 associated with external unit 120, a power source 140, such as a battery, a primary antenna 152, and an electrical circuit 170. Electronics portion 1205 may also include any other component described herein as associated with external unit 120. Additional components may also be recognized by those of skill in the art.

Electronics housing 1202 may include receiver 1204 configured to receive and retain connector 1203. Electronics housing 1202 may include at least one electrical connector 1210, 1211, 1212. Electrical connectors 1210, 1211, 1212 may be arranged with pairs of electrical contacts, as shown in FIG. 12*b*, or with any other number of electrical contacts. The pair of electrical contacts of each electrical connector 1210, 1211, 1212 may be electrically connected with each other inside of housing 1202, such that the pair of electrical contacts represents a single connection point to a circuit. In such a configuration, it may only be necessary that one of the electrical contacts within a pair be contacted in order to establish a suitable electrical connection between electrical connectors 1210, 1211, 1212 and any corresponding connection elements provided on housing 1202, for example. Electrical connectors 1210, 1211, and 1212 may thus include redundant electrical contacts. The electrical contacts of each electrical connector 1210, 1211, 1212 may also represent opposite ends of a circuit, for example, the positive and negative ends of a battery charging circuit. In an exemplary embodiment, as shown in FIG. 12*b*, mechanical connector 1203 may be configured to maintain contact between electrical connectors 1210, 1211, and 1212, arranged on bottom surface 1250 of housing 1202 and exposed electrical portions 1108, 1109 (FIG. 6) of carrier 1201 when mechanical connector 1203 is received by receiver 1204 of electronics housing 1202.

As illustrated in FIGS. 12*a* and 12*b*, mechanical connector 1203 may be adapted to permit relative rotation between carrier 1201 and housing 1202. For example, in an embodiment wherein mechanical connector 1203 includes substantially circular extension, housing 1202 may include a spin on connector 1203, permitting relative rotation between carrier 1201 and housing 1202. In alternative examples, wherein mechanical connector 1203 engages with receiver 1204 disposed on a perimeter of housing 1202, housing 1202 may be permitted to rotate within a circular portion defined by mechanical connector 1203.

In an exemplary embodiment, electronics housing 1202 and carrier 1201 may be configured to maintain electrical contact independent of an axial orientation of housing 1202 with respect to carrier 1201. Therefore, when housing 1202 is mated with and secured to carrier 1201, for example, through connector 1203 and receiver 1204, housing 1202 may be configured to rotate with respect to carrier 1201 while maintaining electrical contact between housing 1202 and carrier 1201. Housing 1202 may be configured to rotate a predetermined degree of rotation while maintaining electrical contact. The predetermined degree of rotation may include, for example, about 360 degrees, more than about 360 degrees, or an angle less than 360 degrees (e.g. about 180 degrees, about 90 degrees, or about 45 degrees). Additionally, housing 1202 may be configured to rotate upwards or downwards with respect to carrier 1201. For example, a left side of sidewall 1251 may rotate upward and away from carrier 1201 while a right side of sidewall 1251 may rotate downward and toward carrier 1201, while still maintaining electrical contact between housing 1202 and carrier 1201. It is further contemplated that carrier 1201 may be configured to rotate with respect to housing 1201.

Rotation of housing 1201 and/or carrier 1201, while maintaining electrical contact between the components, may be accomplished through connectors 1210, 1211, 1212 on housing 1202 and exposed electrical portions 1108 on carrier 1201, electrical connectors 1210, 1211, and 1212 may be configured so as to maintain electrical contact with exposed electrical portions 1108, on carrier 1201, independent of an axial orientation of electronics housing 1202. Connection between any or all of electrical connectors 1210, 1211, 1212 and exposed electrical portions 1108 may thus be established and maintained irrespective of relative axial positions of carrier 1201 and housing 1202. Thus, when connector 1203 is mated with receiver 1204, housing 1202 may rotate with respect to carrier 1201 without interrupting electrical contact between at least one of electrical connectors 1210, 1211, 1212 and exposed electrical portions 1108, 1109. Axial orientation independence may be achieved, for example, through the use of circular exposed electrical portions 1108, 1109 and each of a pair of contact portions 1213 of electrical connectors 1210, 1211, 1212 disposed equidistant from a center of receiver 1204 at a radius approximately equal to that of a corresponding exposed first electrical portion 1108. In this fashion, even if exposed electrical portion 1108 includes a discontinuous circle, at least one electrical contact 1213 of electrical connectors 1210, 1211, and 1212 may make contact with a corresponding first electrical portion 1108. In FIG. 12*b*, electrical connectors 1210, 1211, 1212 are illustrated as pairs of rectangular electrical contacts. Electrical connectors 1210, 1211, 1212, however, may include any number of contacts 1213, be configured as continuous or discontinuous circles, or have any other suitable shape or configuration.

Electrical connectors 1210, 1211, 1212, may be arranged in a predetermined pattern with respect to exposed electrical portions 1108 to achieve the axial orientation independence of housing 1202 and carrier 1201. For example, the pairs of electrical contacts 1215 may be disposed equidistant from a center C of bottom surface 1250 of housing 1202 (FIG. 12*b*). In some embodiments, the pairs of electrical contacts 1215 may be disposed equidistant from a center of receiver 1204. This arrangement of the pairs of electrical contacts 1215 may allow electrical connectors 1210, 1211, 1212 to be equally spaced from the center as electrical connectors 1210, 1211, 1212 on a corresponding electrical contact 1215. For example, as shown in FIG. 12*b*, an outer connector 1210 on a first electrical contact 1215 is disposed at a distance from the center C equal to a distance from the center C where outer connector 1210 on a second (or other) electrical contact 1215 is located. In such a configuration, as housing 1202 rotates relative to carrier 1201, at least one electrode from one or more of the pairs of electrodes 1210, pairs 1211, and pairs 1212 may remain in electrical contact with respective electrodes or electrical portions associated with housing 1202.

The electrical connectors 1210, 1211, 1212 may be disposed a distance from center C substantially equal to the radius of a corresponding exposed electrical portion 1108. For example, electrical connector 1210 may be disposed a distance equal to the radius R1 of first exposed electrical portion 1108*a* (FIG. 11*c*). Therefore, electrical connector 1210 may be disposed substantially directly over first exposed electrical portion 1108*a*. Additionally, electrical connector 1211 may be disposed a distance equal to the radius R2 of second exposed electrical portion 1108*b*, and therefore substantially over second exposed electrical portion 1108*b*. Each of electrical connectors 1210, 1211, 1212 may make contact with its corresponding exposed electrical portion 1108. Therefore, first exposed electrical portion 1108*a* may be in electrical contact with electrical connector 1210, and second exposed electrical portion 1108*b* may be in electrical contact with connector 1211. When exposed electrical portions 1108 include a discontinuous circle, such as first exposed electrical portion 1108*a*, thereby substantially preventing electrical contact between first exposed electrical portion 1108*a* and its corresponding electrical connector 1210, electrical contact between housing 1202 and carrier 1201 may still be maintained between second exposed electrical portion 1108*b* and electrical connector 1211.

In other embodiments, electrical connectors 1210, 1211, 1212 may make contact with an offset exposed electrical portion 1108. For example, continuing the above example, electrical connector 1212 may be offset from second electrical portion 1108*b*, but still configured to make electrical contact with second electrical portion 1108*b*. Therefore, when housing 1202 includes more electrical connectors than there are exposed electrical portions 1108, each electrical connector may be in continuous electrical contact with carrier 1201. Housing 1202 may include any number of electrical connectors with regard to the number of exposed electrical portions 1108 on carrier 1201.

When in electrical contact with electrical connectors 1210, 1211, 1212, exposed electrical portions 1108 may also be electrically connected to the electrical components contained in electronics portion 1205. However, in some embodiments, electrical connectors 1210, 1211, 1212 may be used in configurations not involving contact with electrodes on carrier 1201. In such embodiments, for example, electrical connectors 1210, 1211, 1212 may be configured to function as opposite ends of a battery charging circuit and may be configured and used to charge a battery contained in electronics portion 1205 when electronics housing 1202 is not being used for therapy. A battery charger unit may be provided with a connector similar to that of connector 1203, and configured to engage with receiver 1204. Upon engaging with receiver 1204, electrode contacts of the battery charger unit may contact electrical contact portions 1213 of connector 1210 to charge a battery contained within electronics portion 1205.

As shown in FIG. 12*b*, electrical connectors 1210, 1211, 1212 are illustrated as substantially rectangular. However, electrical connectors 1210, 1211, 1212 may include a variety of shapes and configurations. For example, these electrical connectors may be circular, elliptical, triangular, square, etc. In some embodiments, electrical connectors 1210, 1211, 1212 may be configured as continuous or discontinuous patterns (e.g., circular patterns or patterns of any other suitable shape). It is further contemplated that housing 1202 may include any suitable number of connectors.

In an additional embodiment consistent with the present disclosure, electronics housing 1202 may include an activator chip. Processor 144 may be configured to activate when at least one of electrical connectors 1210, 1211, 1212 contact exposed electrical portions 1108 included in carrier 1201. In this manner, an electronics housing 1202 may be charged and left dormant for many days prior to activation. Simply connecting electronics housing 1202 to carrier 1201 (and inducing contact between an electrical connector 1210, 1211, 1212 and an electrical portion 1108) may cause the processor to activate. Upon activation, processor 144 may be configured to enter a specific mode of operation, such as a calibration mode (for calibrating the processor after placement of the carrier on the skin), a placement mode (for assisting a user to properly place the carrier on the skin), and/or a therapy mode (to begin a therapy session). The various modes of processor 144 may include waiting periods at the beginning, end, or at any time during. For example, a placement mode may include a waiting period at the end of the mode to provide a period during which a subject may fall asleep. A therapy mode may include a similar waiting period at the beginning of the mode. Additionally or alternatively, processor 144 may be configured to provide waiting periods separate from the described modes, in order to provide a desired temporal spacing between system activities.

In accordance with an exemplary embodiment of the disclosure, processor 144 may be configured to initiate a therapy protocol upon coupling of electronics housing 1202 and carrier 1201. For example, processor 144 may be activated immediately upon coupling electronics housing 1202 to carrier 1201 or at a time after coupling to initiate the therapy protocol. Activation may be manually or automatically achieved.

More particularly, in some embodiments, electronics housing 1202 may include an activator circuit associated with processor 144. In certain embodiments, a user may manually trigger the activator circuit and thus activate processor 144. In other embodiments, the activator circuit may be triggered when at least one electrical connector 1210, 1211, 1212 contacts on exposed electrical portion 1108 on carrier 1202. In this manner, simply connecting electronics housing 1202 to carrier 1201 and inducing contact between at least one electrical connector 1210, 1211, 1212 on electronics housing 1202 and an electrode portion 1108 on carrier 1201, may cause processor 144 to automatically activate.

Upon activation, processor 144 may communicate with implant unit 110. Processor 144 may be further configured to generate and deliver one or more therapeutic control signals to implant unit 110 for modulating at least one nerve in the subject's body. These therapeutic control signals will be discussed in more detail below.

In the present disclosure, processor 144 may be configured to delay generation of the therapeutic control signals so that one or more events can occur. For example, processor 144 may be configured to delay the generation of the therapeutic control signals by a predetermined amount of time following the activation of processor 144 so that one or more pre-treatment actions may occur. Such actions may include physical placement of external unit 120 on the subject's body or calibration of control unit 1252 (e.g., calibration of one or more processes or functions provided by processor 144). The delay may also be selected to enable the subject to fall asleep, etc. The subject may initiate the delay, or the delay may automatically occur. The predetermined amount of time may be set by the subject, another person (e.g., the manufacturer or a doctor), or stored as data in a memory accessible by processor 144.

As noted above, in certain embodiments, processor 144 may be configured to delay the generation of the therapeutic control signals to enable physical placement of external unit 120 on the subject's body. The delay may be of sufficient duration to properly position the external unit 120 relative to implant unit 110, and adhere carrier 1201 to the skin of the subject. For example, the delay may be of sufficient duration to enable the subject or another user to position carrier 1201 at multiple locations on the subject's skin prior to placement of carrier 1201 at a final, desired location. The final location may be on, for example, the neck, head, and/or chin of the subject. In such embodiments, a delay period sufficient to enable positioning of external unit 120 may be set at 30 seconds, 1 minute, 2 minutes, 5 minutes, 10 minutes, or at any other suitable duration.

In some embodiments, processor 144 may be configured to generate signals indicative of the placement or location of external unit 120 relative to implant 110. Alternatively, processor 144 may receive signals from implant unit 110 indicative of the placement or location of external unit relative to implant unit 110 or that can be used to determine such placement or location. The subject or another person may position carrier 1201 at a location on the subject's body based on feedback (e.g., a visual indicator, audible indicator, haptic indicator, or any other suitable indication) associated with the determined location or relative orientation between implant unit 110 and external unit 120. Processor 144 may be further configured to emit a control signal (e.g., a sub-modulation control signal having an amplitude, duration, etc. selected so as to fall below a stimulation threshold for a nerve or nerve tissue) in order to determine the location of implant unit 110 relative to external unit 120. Processor 144 may be configured to discontinue the control signal after the carrier has been affixed or adhered to subject's skin at a desired location.

In certain other embodiments, processor 144 may be configured to delay the generation of the therapeutic control signals to enable calibration of control unit 1252 including components (e.g., processor 144) of control unit 1252. The delay may be of sufficient duration such that the calibration procedure occurs over a time duration equal to or less than the selected delay period. In some embodiments, the calibration delay period may extend for a few microseconds, a few milliseconds, 1 second, 5 seconds, or over any other suitable time duration. If two or more processors are included in electronics housing 1202, the delay may be of sufficient duration so that both processors may be calibrated within a single delay period.

In yet other embodiments, processor 144 may be configured to delay the generation of the therapeutic control signals to enable the subject to fall asleep. For example, the duration of the delay may be in the range of about 15 minutes to about 90 minutes. In preferred embodiments, the delay may be in the range of about 30 minutes to about 90 minutes. In some embodiments, especially in view of experimental results indicating that the patients do not perceive the modulation events, a waiting period for allowing the subject to fall asleep may not be required. In such embodiments, the predetermined amount of time may be zero i.e., processor 144 may immediately enable generation of the modulation signals.

It is contemplated that the delay may be of sufficient duration to enable two or more of the actions discussed above to occur. It is further contemplated that the delay may be of sufficient duration to enable three or more actions to occur following activation of processor 144. In certain embodiments no delay may be required, and therefore no delay may occur.

Figure 6:
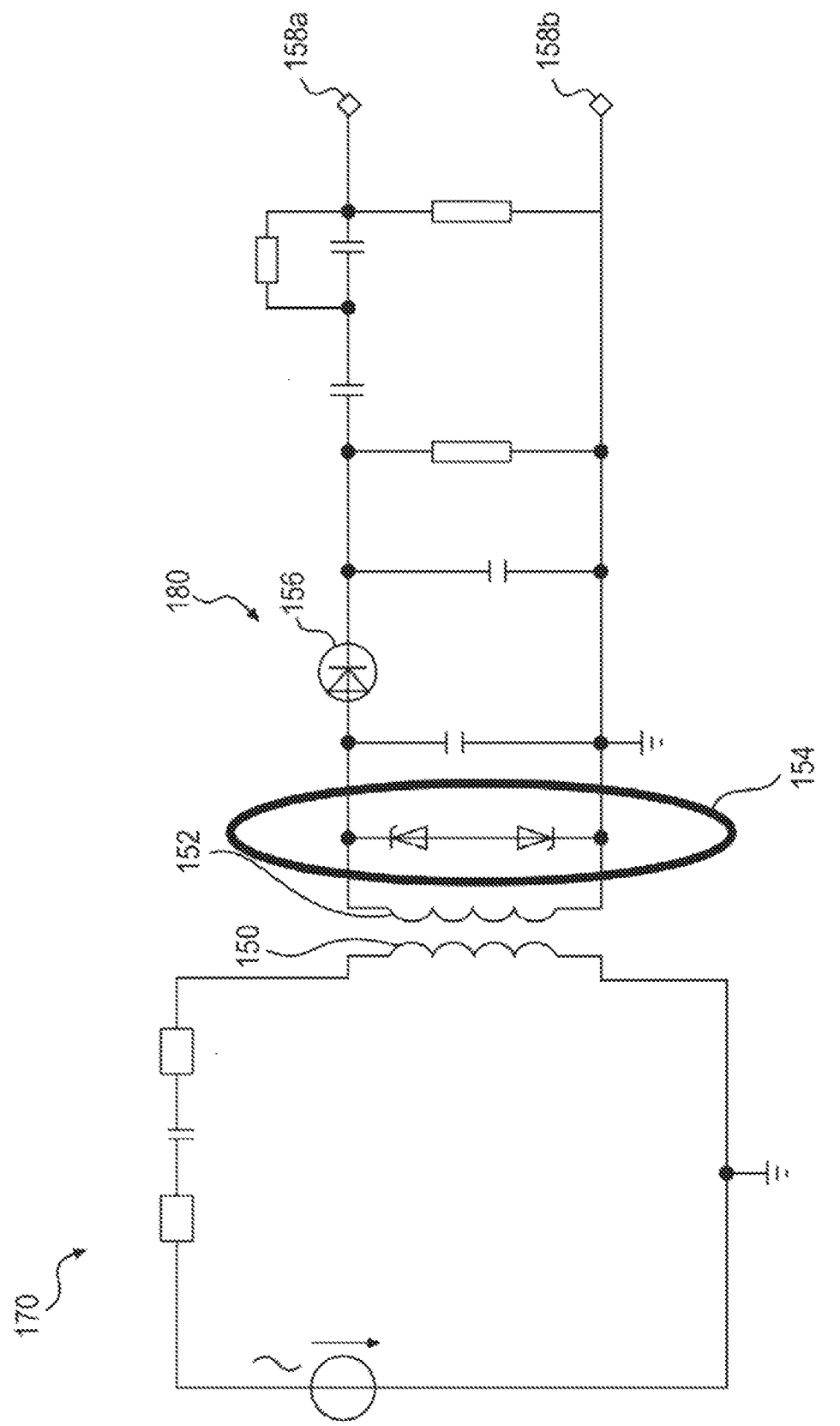
FIG. 6 illustrates circuitry of an implant unit and an external unit, according to exemplary embodiments of the present disclosure.
Figure 18:
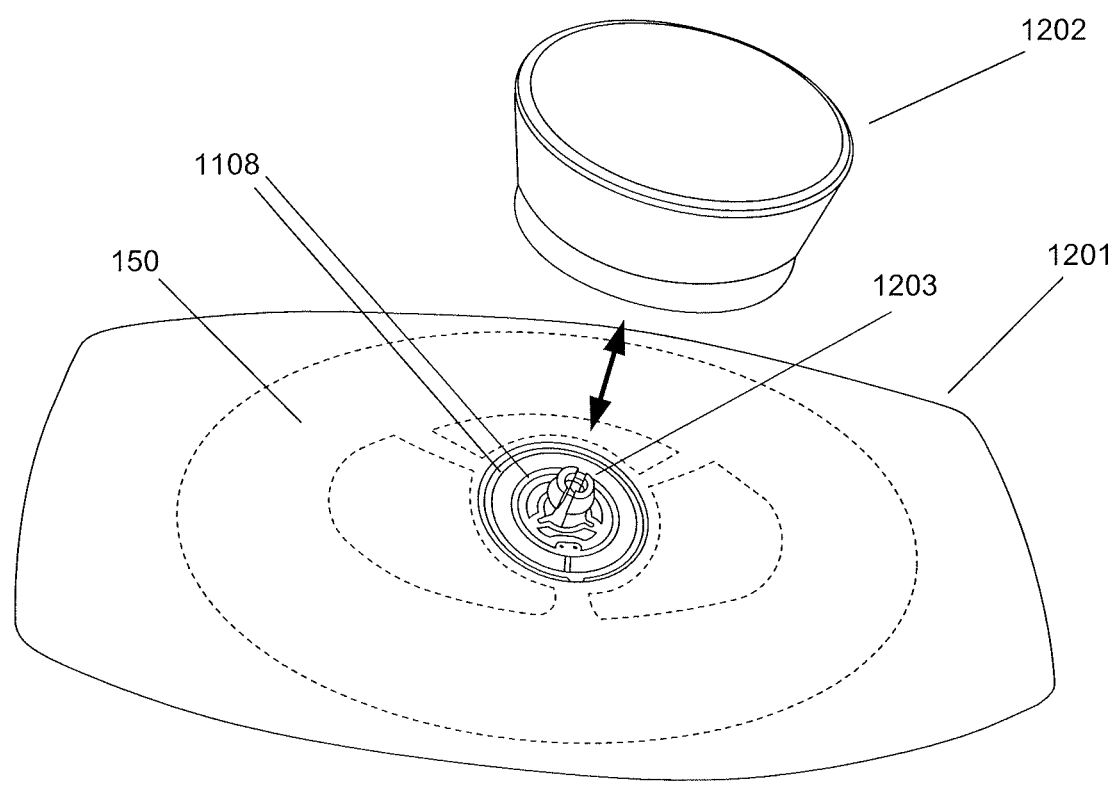
FIG. 18 is a perspective view of an exemplary external unit.

FIG. 18 provides a perspective view of an exemplary external unit 120. As illustrated in FIG. 6, carrier 1201 may include a connector 1203 extending from carrier 1201. Connector 1203 may be configured to be received and retained by a receiver associated with housing 1202. For example, connector 1203 may be configured as a peg, post, tab (or any of the structures described above relative to connector 1203) shaped to be received into one or more recessed areas associated with housing 1202. Similarly, connector 1203 and/or housing 1202 may include structures (e.g., detents, etc.) to enable selective attachment to and retention of connector 1203 by housing 1202. In this way, housing 1202 may be mounted on carrier 1201. Once mounted, the electrical connectors 1210, 1211, 1212 of housing 1202 may engage with exposed electrical portions 1108, 1109 of carrier 1201.

Figure 19A:
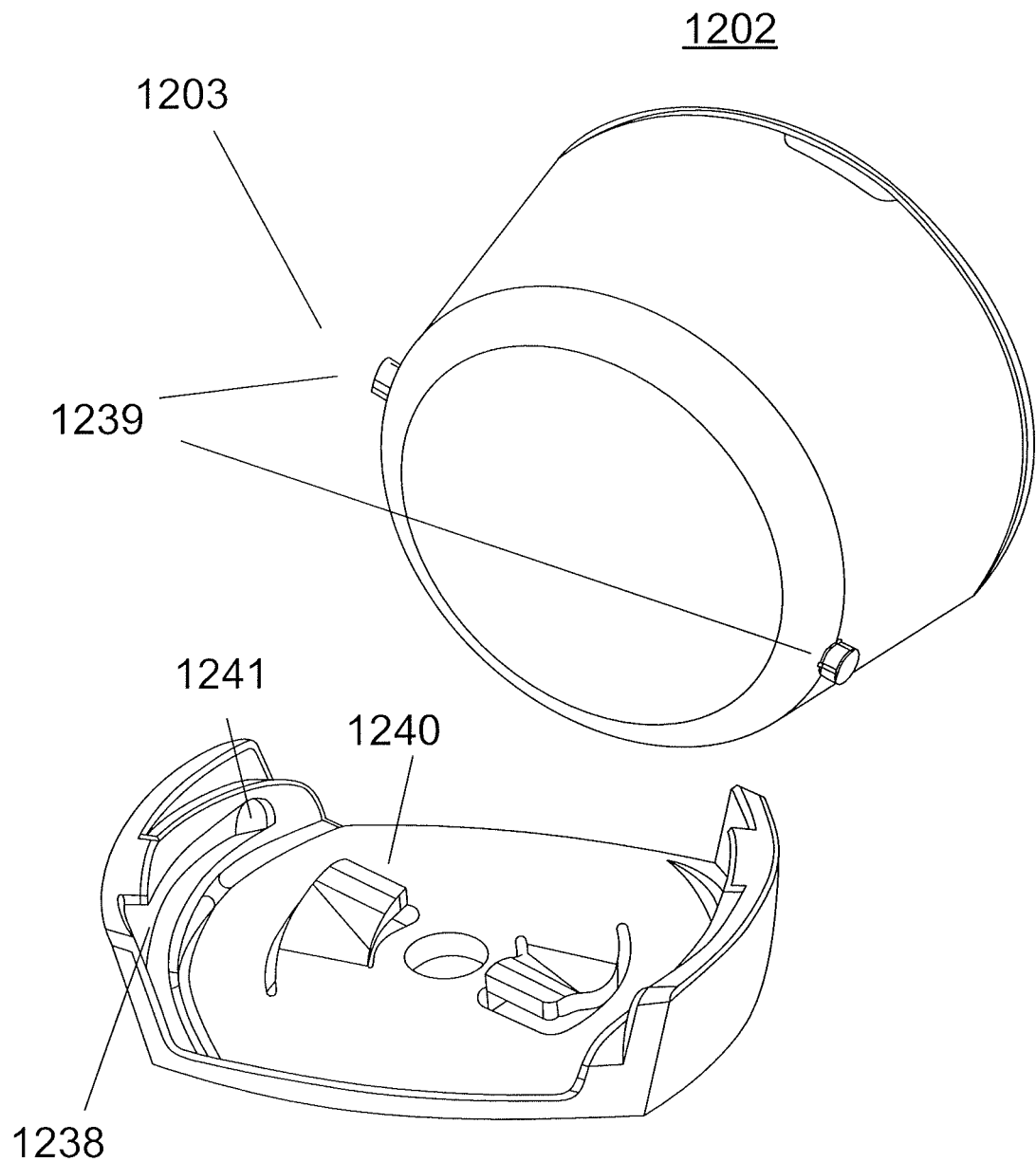

FIGS. 19*a-f* illustrate several additional exemplary embodiments of structures for enabling selective mounting of housing 1202 to carrier 1201. For example, FIG. 19*a* illustrates an exemplary embodiment of an external unit featuring a bayonet mount. In this embodiment connector 1203 may include extending portions 1218 configured to extend or protrude from carrier 1201. Extending portions 1218 may include receptor slots 1238 and retaining portions 1241. Further, connector 1203 may include at least one biasing mechanism 1240 configured to extend or protrude from the carrier. Receiver 1203 may include a plurality of radial pins 1239, corresponding in number to receptor slots 1238. Radial pins 1239 may be disposed on a portion of a perimeter of the housing. Carrier 1201 is not illustrated in FIG. 19*a*; however, connector 1203 may form part of carrier 1201, for example, as an integrally formed portion or as a portion affixed to carrier 1201. Radial pins 1239 may be configured as protrusions extending from the housing, and may be configured to engage and retain receptor slots 1238 of connector 1203. Radial pins 1239 may further be configured to be inserted into the receptor slots 1238 and to securely engage connector 1203 when the housing 1202 is rotated with respect to connector 1203. Although FIG. 19*a* illustrates an embodiment including two radial pins 1239, any suitable number of radial pins 1239 may be included. Biasing mechanism 1240 may provide a vertical force to seat radial pins 1239 in retention portion 1241 of receptor slot 1238. Biasing mechanism 1240 may include any type of elastically deformable element capable of providing a biasing force. For example, biasing mechanism may include a spring, or may include flexible plastic tabs. In some embodiments, biasing mechanism 1240 and electrical connectors 1210, 1211, and 1212 may be incorporated in the same structure. For example, electrical connectors 1210, 1211, and 1212 may include elastically deformable metal tabs configured to act as biasing mechanism 1240 by providing a biasing force. Biasing mechanism 1240 may be provided on as part of connector 1203 (as illustrated) or, in some embodiments, as part of receiver 1204 on housing 1202.

Figure 19B:
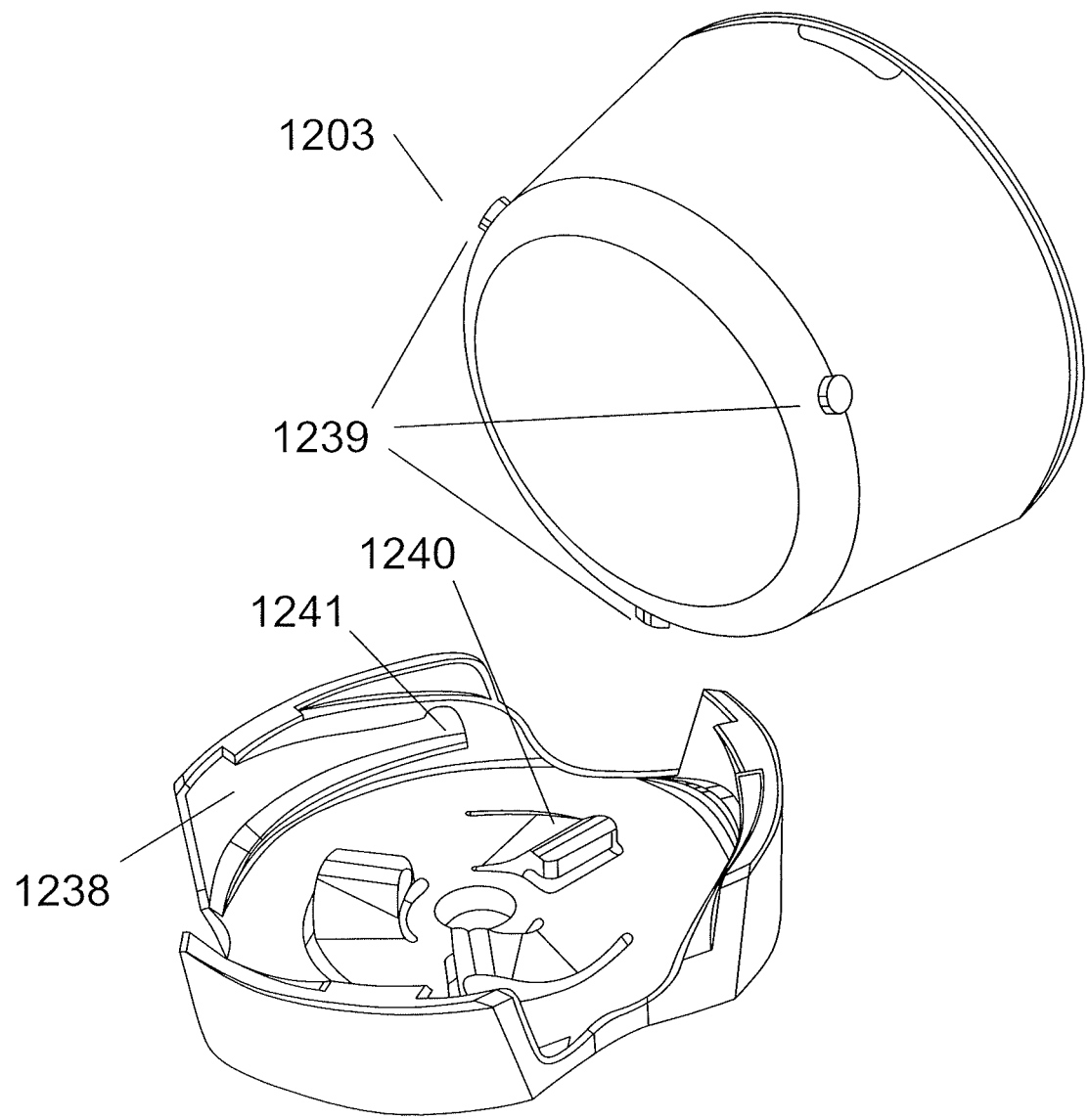

FIG. 19*b* illustrates an additional embodiment including a bayonet mount. FIG. 19*b* illustrates a bayonet mount including three radial pins 1239. Carrier 1201 is not illustrated in FIG. 19*b*; however, connector 1203 may form part of carrier 1201, for example, as an integrally formed portion or as a portion affixed to carrier 1201.

Figure 19C:
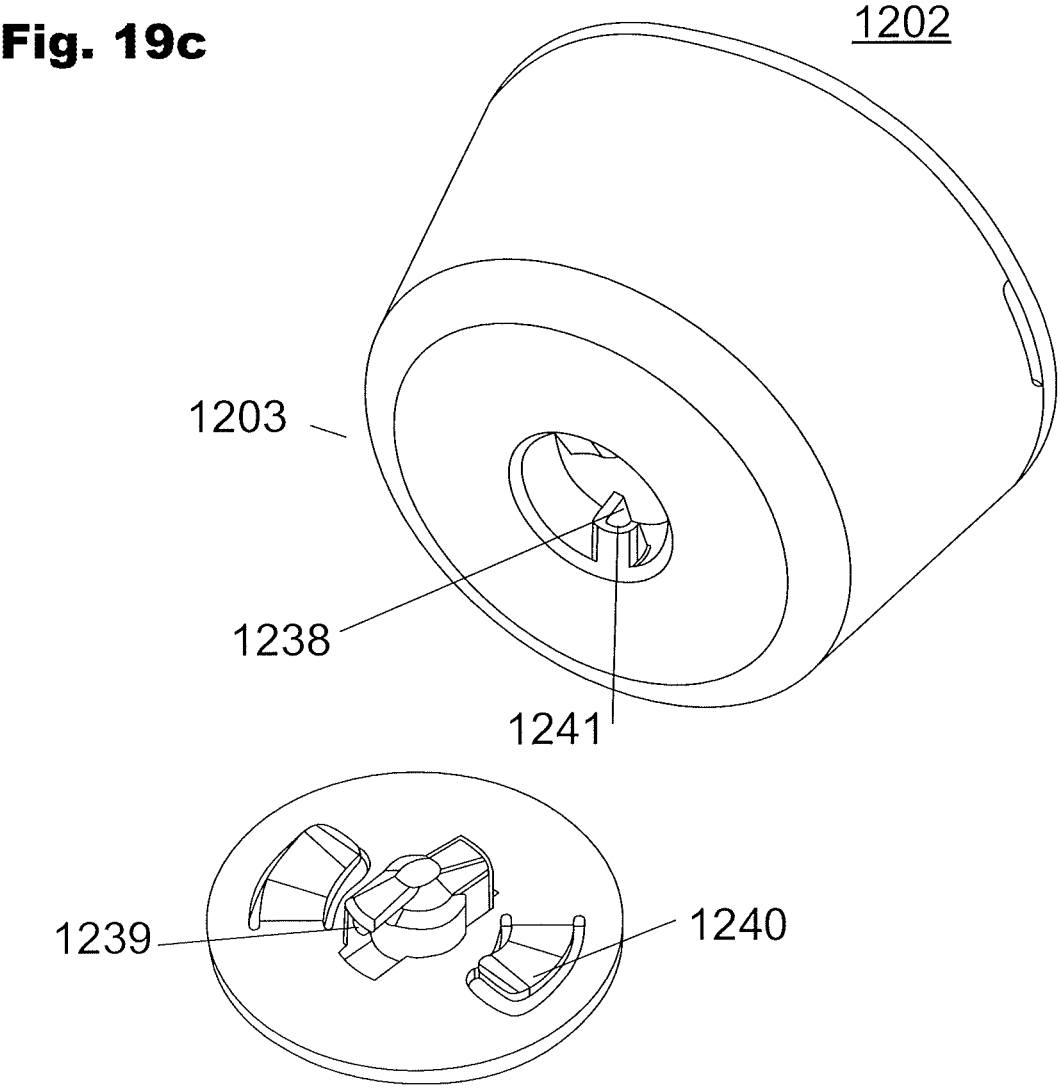

FIG. 19*c* illustrate an additional embodiment including a bayonet mount. For clarity purposes, carrier 1201 is not illustrated in FIG. 19c. Connector 1203 may include an extending portion 1218 and biasing mechanisms 1240 configured to extend or protrude from carrier 1201. As illustrated in FIG. 19c, protruding connector 1203 may include radial pins 1239 for bayonet mounting, and may be arranged inside of a perimeter provided by biasing mechanism 1240. Receiver 1204 may include a recessed portion including receptor slot 1238 and retention portions 1241. Connector 1203 may be configured to engage and be retained by receiver 1204 by inserting extending portion 1218 into the recessed portion of receiver 1204 and rotating housing 1202 with respect to connector 1203. During rotation, biasing mechanisms 1240 may be compressed. When radial pins 1239 are seated in retention portions 1241, biasing mechanisms 1240 may press housing 1202 away from carrier 1201, thus preventing further rotation between the two.

Figure 19D:
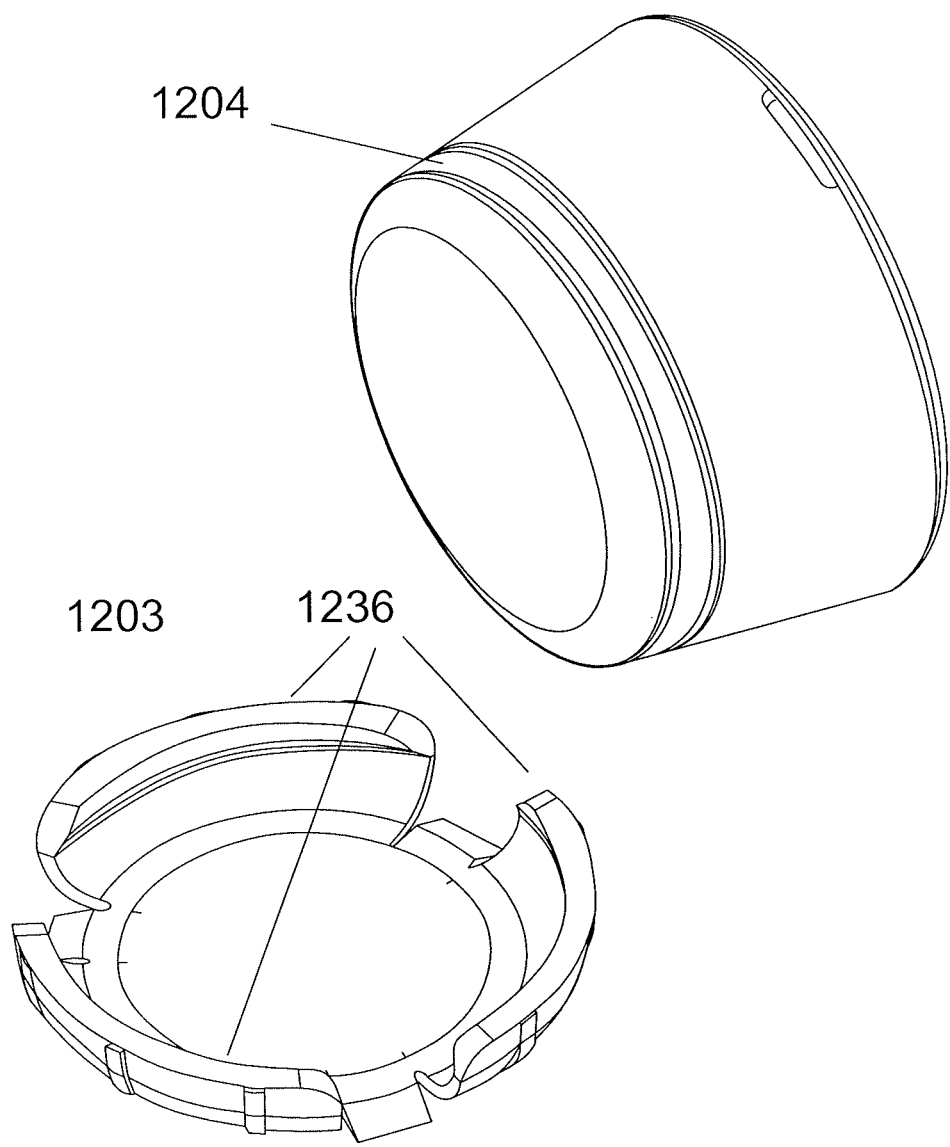

FIG. 19d illustrates an embodiment wherein receiver 1204 includes an annular groove 1217 and is disposed on at least a portion of a perimeter of housing 1202. In this embodiment, annular groove 1217 may form a recessed portion of receiver 1204. Annular groove 1217 may include a detent engagement portion 1233, for example, a lip, rim, or flange. In this embodiment, receiver 1204 may be configured to engage a connector 1203 including a plurality of flexible extension arms 1236. Flexible arms 1236 may each include a detent portion 1232, such as a tab or a hook, for engagement with detent engagement portion 1233 of annular groove 1217. Upon engagement, flexible extension arms 1236 may elastically deform outwards to accommodate receiver 1204 before "snapping" into an engaged position. For clarity purposes, carrier 1201 is not illustrated in FIG. 19d, Flexible extension arms 1236 of connector 1203 may extend or protrude from carrier 1201.

FIG. 19e illustrates an embodiment wherein mechanical connector 1203 features both a central rodlike element 1231 and flexible extension arms 1236 arranged at a perimeter. Both connector 1203 and flexible extension arms 1236 may extend or protrude from carrier 1201 (not illustrated). Rodlike element 1231 may also include flexible extension arms 1234. Either or both of flexible extension arms 1236 and 1234 may include detent portions 1232. Receiver 1204, in this embodiment, may include a plurality of recessed portions, for example, both a centrally located concavity 1235 and a peripherally located annular groove 1217 of housing 1202. Either or both of annular groove 1217 and concavity 1235 may include detent engagement portions 1233 to engage detent portions 1232 of extension arms 1236 and/or extension arms 1234, respectively. Upon engagement, retention of housing 1202 may be secured by either or both of the engagement between rodlike element 1231 and concavity 1235 and the engagement between extension arms 1236 and annular groove 1217. Extension arms 1234 and 1236 may be configured to elastically deform to facilitate engagement. In some embodiments, either rodlike element 1231 or flexible arms 1236 do not include detent portions, and function only to facilitate alignment of connector 1203 and receiver 1204.

Figure 19F:
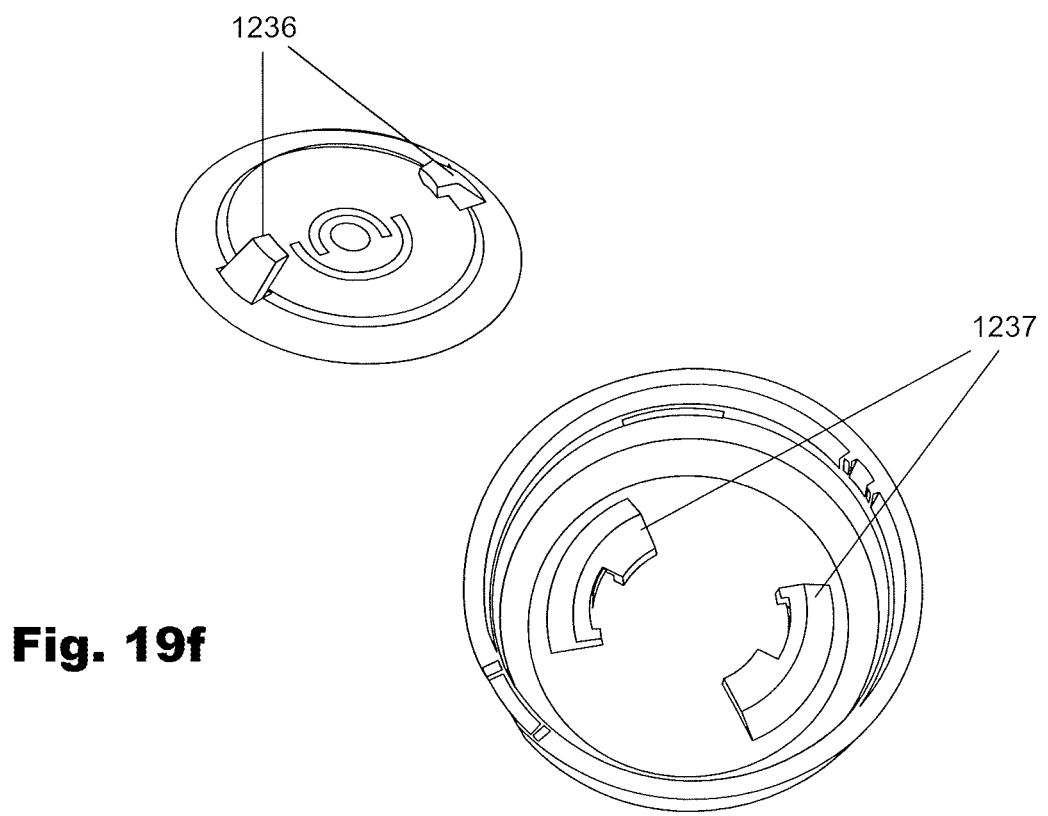

FIG. 19f shows an embodiment configured to engage connector 1203 including a twist-lock connector. As illustrated, receiver 1204 may include a plurality of recesses 1237 including detent engagement portions 1233 while connector 1203 includes a plurality of extension arms 1236 including detent portions 1232. The extension arms 1236 may be configured to be inserted into the recesses 1237 and to securely engage the housing 1202 when the housing 1202 is rotated with respect to the extension arms 1236. Extension arms 1236 of connector 1203 may extend or protrude from carrier 1201 (not illustrated).

The foregoing examples of embodiments of receiver 1204 and connector 1203 are provided for exemplary purposes only. The exemplary embodiments discuss various combinations of features that provide a releasable engagement between carrier 1201 and housing 1202. In alternative embodiments, the various features described may be combined in different ways. For example, while the embodiments discussed in the foregoing generally include a receiver 1204 disposed on a housing 1202 and a connector 1203 disposed on a carrier 1201, this arrangement may be reversed. That is, receiver 1204 may be located on carrier 1201 and connector 1203 may be located on housing 1202. In such embodiments, connector 1203 and receiver 1204 may include any or all of the features discussed above with respect to connector 1203 and receiver 1204. For example, connector 1203 may be a protrusion extending from housing 1202, and receiver 1204 may include recessed portion or concavity of carrier 1201. In such an arrangement, connector 1203 may be configured to engage and be retained within the recessed portion or concavity of receiver 1204. In such an arrangement at least a portion of a sidewall 1251 and a top surface 1252 of housing 1202 may be exposed when the housing is mounted on the flexible adhesive patch.

Figure 4:
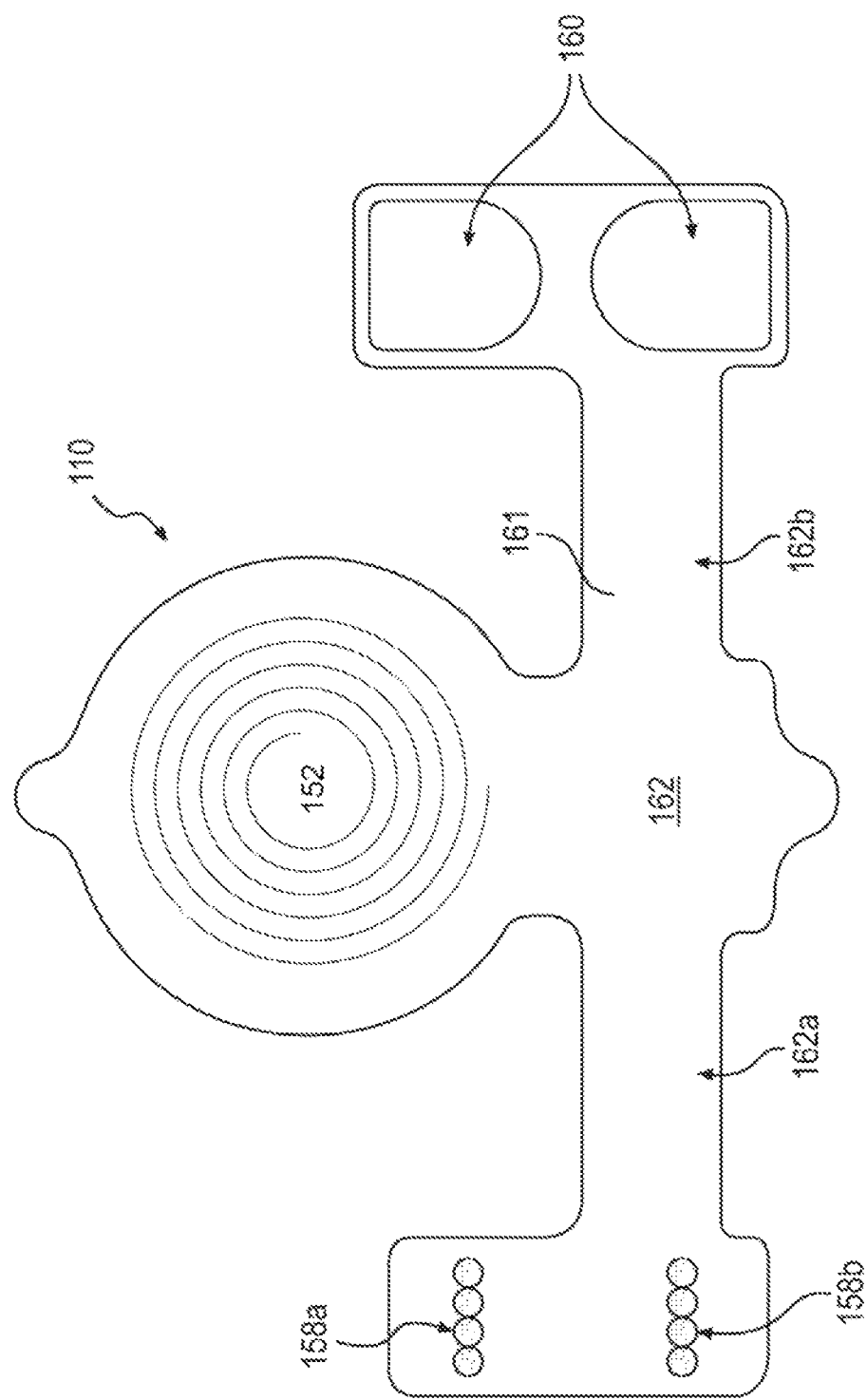
FIG. 4 is a top view of an implant unit, according to exemplary embodiments of the present disclosure.

Implant unit 110, as shown in FIG. 3, may additionally include a plurality of field-generating implant electrodes 158a, 158b. The electrodes may include any suitable shape and/or orientation on the implant unit so long as the electrodes may be configured to generate an electric field in the body of a patient. Implant electrodes 158a and 158b may also include any suitable conductive material (e.g., copper, silver, gold, platinum, iridium, platinum-iridium, platinum-gold, conductive polymers, etc.) or combinations of conductive (and/or noble metals) materials. In some embodiments, for example, the electrodes may include short line electrodes, circular electrodes, and/or circular pairs of electrodes. As shown in FIG. 4, electrodes 158a and 158b may be located on an end of a first extension 162a of an elongate arm 162. The electrodes, however, may be located on any portion of implant unit 110. Additionally, implant unit 110 may include electrodes 158a, 158b located at a plurality of locations, for example on an end of both a first extension 162a and a second extension 162b of elongate arm 162, as illustrated, for example, in FIG. 5. Implant electrodes 158a, 158b may have a thickness between about 200 nanometers and 1 millimeter. Anode and cathode electrode pairs of electrodes 158a, 158b may be spaced apart by about a distance of about 0.2 mm to 25 mm. In additional embodiments, anode and cathode electrode pairs may be spaced apart by a distance of about 1 mm to 10 mm, or between 4 mm and 7 mm. Adjacent anodes or adjacent cathodes may be spaced apart by distances as small as 0.001 mm or less, or as great as 25 mm or more. In some embodiments, adjacent anodes or adjacent cathodes may be spaced apart by a distance between about 0.2 mm and 1 mm.

FIG. 4 provides a schematic representation of an exemplary configuration of implant unit 110. As illustrated in FIG. 4, in one embodiment, the field-generating electrodes 158a and 158b may include two sets of four circular electrodes, provided on flexible carrier 161, with one set of electrodes providing an anode and the other set of electrodes providing a cathode. Implant unit 110 may include one or more structural elements to facilitate implantation of implant unit 110 into the body of a patient. Such elements may include, for example, elongated arms, suture holes, polymeric surgical mesh, biological glue, spikes of flexible carrier protruding to anchor to the tissue, spikes of additional biocompatible material for the same purpose, etc. that facilitate alignment of implant unit 110 in a desired orientation within a patient's body and provide attachment points for securing implant unit 110 within a body. For example, in some embodiments, implant unit 110 may include an elongate arm 162 having a first extension 162a and, optionally, a second extension 162b. Extensions 162a and 162b may aid in orienting implant unit 110 with respect to a particular muscle (e.g., the genioglossus muscle), a nerve within a patient's body, or a surface within a body above a nerve. For example, first and second extensions 162a, 162b may be configured to enable the implant unit to conform at least partially around soft or hard tissue (e.g., nerve, bone, or muscle, etc.) beneath a patient's skin.

Further, implant unit 110 may also include one or more suture holes as attachment points for securing implant unit 110 to tissue in the patient's body. Implant unit 110 may include any number of suture holes suitable for a particular application. For example, in some embodiments, implant unit 110 may include one or more suture holes 160, as shown in FIG. 4. In other embodiments, implant unit 110 may include one or more suture holes 1060, 1064 and may also include one or more suture holes 1050.

Figure 10:
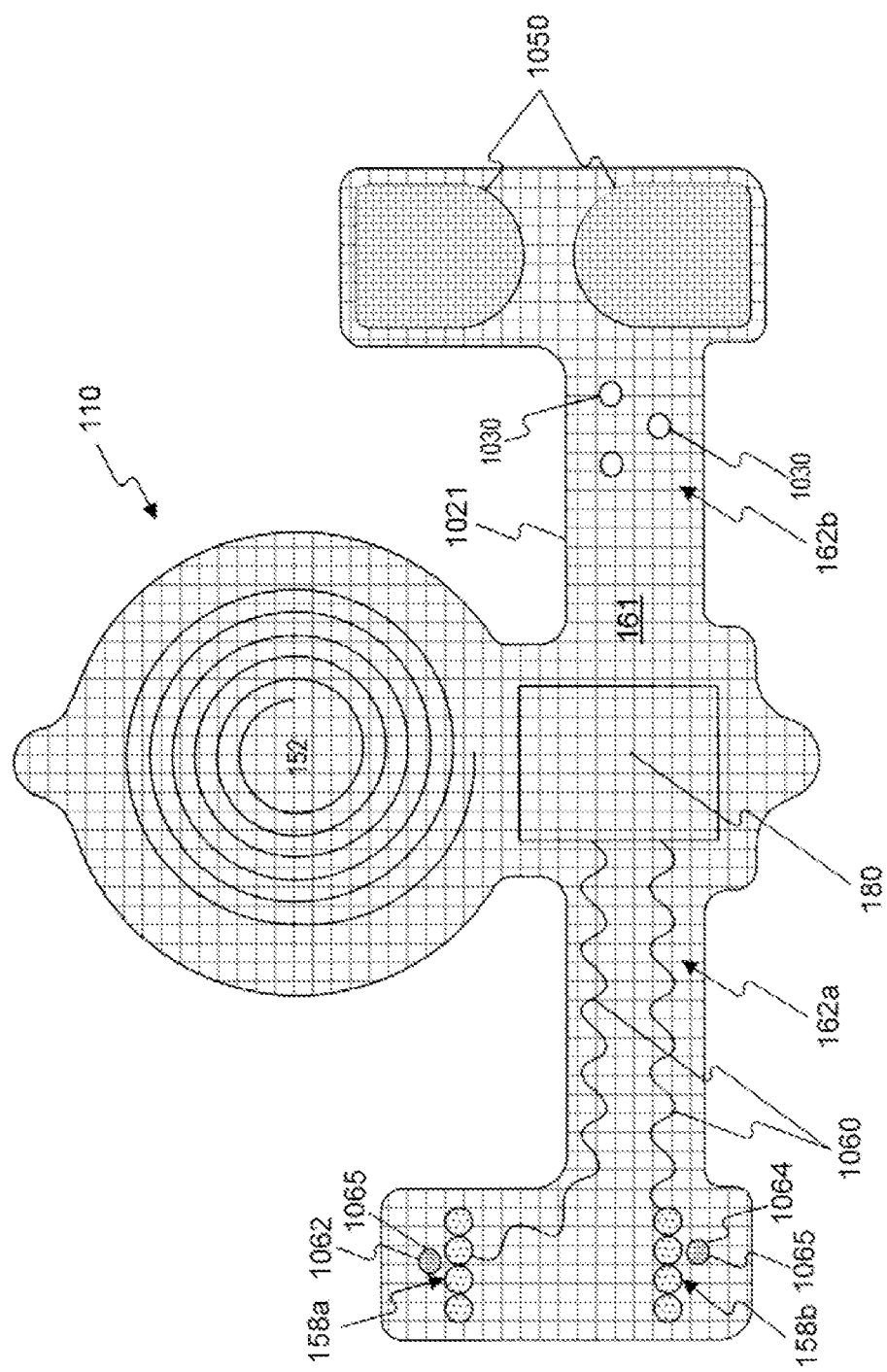
FIG. 10 illustrates additional features of an embodiment of implant unit 110.

The one or more suture holes 160 may be located anywhere on implant unit 110. In some embodiments the one or more suture holes may be located on one end of the implant unit 110, on one side of implant unit 110, or on an extension portion of implant unit 110. Alternatively, or in addition, the one or more suture holes may be located on opposite ends of implant unit 110. FIG. 4 illustrates that in some embodiments, the one or more suture holes may be located on flexible carrier 161. In some embodiments, the one or more suture holes 160 (FIG. 4), the one or more suture holes 1050 (FIG. 10), or the one or more suture holes 1062, 1064 (FIG. 10) may be positioned on the elongate arm 162 of flexible carrier 161. For example, any of the described suture holes may be placed on at least one of the first extension 162a and the second extension 162b of elongate arm 162. As illustrated in FIGS. 4 and 10, at least one pair of suture holes 160 and/or 1050 may be placed on second extension 162b of elongate arm 162. Suture holes 1062 and 1064 may be included on first extension 162a of elongate arm 162.

The one or more suture holes 160 may further be configured with any desired size, shape, or configuration so long as the one or more suture holes 160, 1050, 1062, 1064 may be configured to enable passage of a suture and suture needle. In some embodiments, for example, the one or more suture holes may be sized such that they include a minor dimension (e.g., a diameter if the hole is circular, or a width if the hole is oval, oblong, rectangular, square, etc.) that is sized to allow passage of a standard suture needle. For example, in some embodiments, the one or more suture holes (e.g., suture holes 1062, 1064) may have a minor dimension of less than about 2 mm. In some embodiments, the one or more suture holes may include a minor dimension less than about 1 mm.

Additionally, or alternatively, the one or more suture holes may include at least one suture hole having a minor dimension that is larger than a minor dimension associated with at least one other suture hole on implant unit 110. For example, in some embodiments, this larger suture hole (e.g., suture holes 160 or 1050) may include a minor dimension of at least 3.75 mm. In some embodiment, the larger suture hole may include a minor dimension of 4 mm or greater.

In addition, the shape of the one or more suture holes 160, 1050, 1062, 1064 may include any suitable shape. For example, in some embodiments, the one or more suture holes may include a shape with rounded edges (e.g., a circle or oval) and/or a shape with one or more straight edges (e.g., a polygon). In some embodiments, the one or more suture holes may be shaped such that they include both straight and rounded edges. Each of the one or more suture holes 160 may be identically shaped and sized. Alternatively, in some embodiments, the one or more suture holes 160 may vary in shape and size from one another. For example, one or more suture holes 160 on one end of the implant unit 110 may include a first size and shape, and one or more suture holes 160 on a second, opposite end of the implant unit 110 may include a second size and shape, such that the first size and/or shape may be different from the second size and/or shape.

In some embodiments, the suture holes may be arranged on implant unit 110 to facilitate the implant procedure. For example, in some embodiments, implant unit 110 may include a flexible carrier configured to conform to tissue in a subject's body. In such embodiments, when the carrier conforms to tissue, the carrier may wrap around the tissue such that one portion of the carrier resides opposite to another portion of the carrier with intervening tissue there between. In some cases, it may be desirable to affix implant unit 110 in such a location. Thus, at least one suture hole may be arranged on a first portion of implant unit 110 (e.g., on first or second extension arm 162a, 162b) such that when the flexible carrier conforms to tissue in the subject's body, the at least one suture hole aligns with another suture hole located on another portion of implant unit 110 (e.g., the other of the first or second extension arm 162a, 162b) across intervening tissue therebetween. In some embodiments, more than one suture hole (e.g., a pair of holes) may be located on the first portion of implant 110 and positioned to allow for tissue to intervene between the one or more suture holes on the first portion and respective holes located on another portion of implant unit 110 when the carrier conforms to or is placed on tissue in the subject's body.

Such configurations may facilitate attachment of implant unit 110 to tissue in the subject's body. For example, in some embodiments, a set of one or more smaller suture holes may be positioned on one side of tissue in the body and may be configured to receive a suture needle at the beginning of the suturing process. Because these holes may be the first holes accessed by the suture needle, they may be configured with a size just large enough to pass the suture needle (e.g., less than 2 mm, less than 1 mm, etc.). To suture implant unit 110 in place, a suture needle may be passed through a first suture hole on one portion of implant unit 110, through tissue in the subject's body, and then through a second suture hole located on another portion of implant unit 110 and across from the first suture hole.

To make the second suture hole easier to access after the suture needle passes through the intervening tissue, the second suture hole may be sized larger than the first suture hole. For example, in some embodiments, the second suture hole may have a minor dimension of at least two times a minor dimension of the first suture hole. In some embodiments, the second suture hole may have a minor dimension of at least about 3.75 mm, at least about 4 mm, or greater.

Referring to the exemplary embodiment shown in FIG. 10, flexible carrier 161 of implant unit 110 may be configured to conform to tissue in a subject's body. For example, in some embodiments, implant unit 110 may be configured to conform to a genioglossus muscle in a subject such that a first extension arm 162a extends on one side of the genioglossus muscle while a second extension art 162b extends on a second side of the genioglossus muscle opposite to the first side. In such embodiments, when implant unit 110 conforms to tissue of the genioglossus muscle or tissue near the genioglossus muscle, suture hole 1062 may be positioned across from a first one of suture holes 1050 through intervening tissue, and suture hole 1054 may be positioned across from another one of suture holes 1050 through intervening tissue. Such a configuration, which may position electrodes 158*a* and 158*b* proximate to or adjacent to terminal fibers of the hypoglossal nerve in order to facilitate modulation of the hypoglossal nerve via the terminal fibers, may also facilitate attachment of implant 110 to tissue of the genioglossus muscle. For example, after a suture needle is passed through one of the smaller holes 1062 or 1064 on one portion of implant unit 110, the larger holes 1050 may be easier to locate with the suture needle, after it emerges from the genioglossus muscle tissue, as compared to holes sized similarly to holes 1062 or 1064.

In some embodiments, the one or more suture holes 160, 1050, 1062, and/or 1064 may include a perforated material extending partially or fully across openings of suture holes 160, 1050, 1062, and/or 1064. The perforated material may be biologically compatible and may facilitate anchoring of sutures within suture holes 160, 1050, 1062, and/or 1064. The perforated material may include any biocompatible perforated material known to those skilled in the art and configured to capture a surgical suture as the surgical suture is passed through the one or more suture holes 160. In addition, the perforated material may be configured to encourage tissue surrounding implant unit to bond with implant unit. In some embodiments the perforated material may include a surgical mesh.

In some embodiments, implant unit may appear substantially as illustrated in FIG. 4. In other embodiments, implant unit 110 may lack illustrated structures such as second extension 162*b*, or may have additional or different structures in different orientations. Additionally, implant unit 110 may be formed with a generally triangular, circular, or rectangular shape, as an alternative to the winged shape shown in FIG. 4. In some embodiments, the shape of implant unit 110 (e.g., as shown in FIG. 4) may facilitate orientation of implant unit 110 with respect to a particular nerve to be modulated. Thus, other regular or irregular shapes may be adopted in order to facilitate implantation in differing parts of the body.

As illustrated in FIG. 4, secondary antenna 152 and electrodes 158*a*, 158*b* may be mounted on or integrated with flexible carrier 161. Various circuit components and connecting wires (discussed further below) may be used to connect secondary antenna with implant electrodes 158*a* and 158*b* in a manner permitting the antenna to transfer at least some of the energy received at the antenna (e.g., from a unit including a primary antenna located external to the body of the subject) to one or more of electrodes 158*a*, 158*b*. Other components that may be included in or otherwise associated with circuitry connecting secondary antenna 152 with electrodes 158*a* and 158*b* may include, for example, modifier circuit 154, diode 156, sensor (not shown), etc. To protect the antenna, electrodes, circuit components, and connecting wires from the environment within a patient's body, implant unit 110 may include a protective coating that encapsulates implant unit 110. In some embodiments, the protective coating may be made from a flexible material to enable bending along with flexible carrier 161. The encapsulation material of the protective coating may also resist humidity penetration and protect against corrosion. In some embodiments, the protective coating may include a plurality of layers, including different materials or combinations of materials in different layers.

Figure 5:
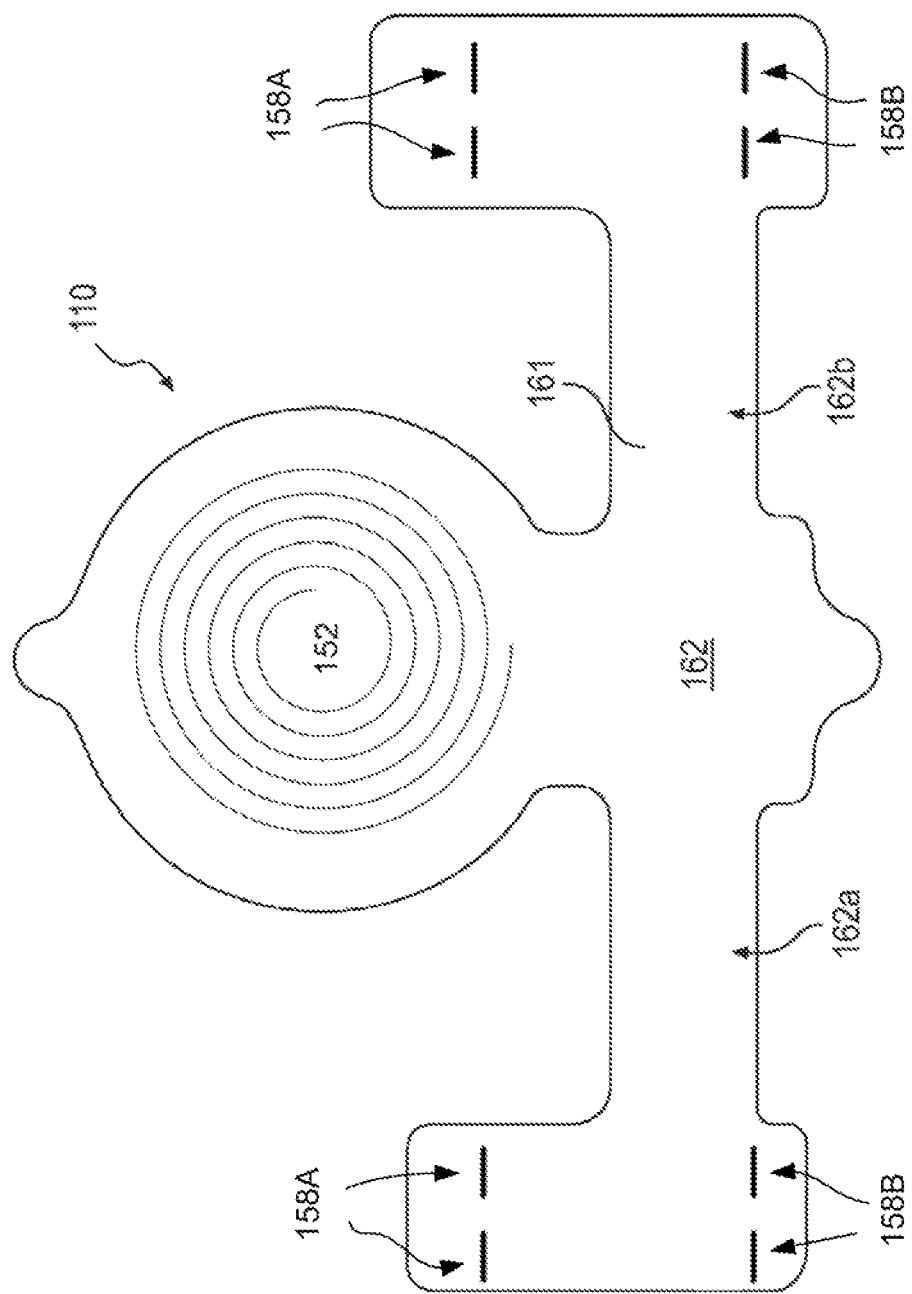
FIG. 5 is a top view of an alternate embodiment of an implant unit, according to exemplary embodiments of the present disclosure.

FIG. 5 is a perspective view of an alternate embodiment of an implant unit 110, according to an exemplary embodiment of the present disclosure. As illustrated in FIG. 5, implant unit 110 may include a plurality of electrodes 158*a*, 158*b*, located, for example, at the ends of first extension 162*a* and second extension 162*b*. FIG. 5 illustrates an embodiment wherein implant electrodes 158*a* and 158*b* include short line electrodes.

In some embodiments of the present disclosure, the encapsulation structure of implanted unit may include two layers. For example, a first layer may be disposed over at least a portion of the implantable circuit arranged on the substrate, and a second layer may be disposed over the first layer. In some embodiments, the first layer may be disposed directly over the implantable circuit, but in other embodiments, the first layer may be disposed over an intervening material between the first layer and the implantable circuit. In some embodiments, the first layer may provide a moisture barrier and the second layer may provide a mechanical protection (e.g., at least some protection from physical damage that may be caused by scratching, impacts, bending, etc.) for the implant unit. The terms "encapsulation" and "encapsulate" as used herein may refer to complete or partial covering of a component. In some embodiments component may refer to a substrate, implantable circuit, antenna, electrodes, any parts thereof, etc. The term "layer" as used herein may refer to a thickness of material covering a surface or forming an overlying part or segment. The layer thickness can be different from layer to layer and may depend on the covering material and the method of forming the layer. For example, a layer disposed by chemical vapor may be thinner than a layer disposed through other methods.

Other configurations may also be employed. For example, another moisture barrier may be formed over the outer mechanical protection layer. In such embodiments, a first moisture barrier layer (e.g., parylene) may be disposed over (e.g., directly over or with intervening layers) the implantable circuit, a mechanical protection layer (e.g., silicone) may be formed over the first moisture barrier, and second moisture barrier (e.g., parylene) may be disposed over the mechanical protection layer. FIG. 10 illustrates exemplary embodiment of encapsulated implant unit 110. Exemplary embodiments may incorporate some or all of the features illustrated in FIG. 10 as well as additional features. A protective coating of implant unit 110 may include a primary capsule 1021. Primary capsule 1021 may encapsulate the implant unit 110 and may provide mechanical protection for the implant unit 110. For example, the components of implant unit 110 may be delicate, and the need to handle the implant unit 110 prior to implantation may require additional protection for the components of implant unit 110, and primary capsule 1021 may provide such protection. Primary capsule 1021 may encapsulate all or some of the components of implant unit 110. For example, primary capsule 1021 may encapsulate antenna 152, flexible carrier 161, and implantable circuit 180. The primary capsule may leave part or all of electrodes 158*a*, 158*b* exposed enabling them to deliver energy for modulating a nerve unimpeded by material of the primary capsule. In alternative embodiments, different combinations of components may be encapsulated or exposed. Primary capsule 1021 may be fashioned of a material and thickness such that implant unit 110 remains flexible after encapsulation. Primary capsule 1021 may include any suitable bio-compatible material, such as silicone, or polyimides, phenyltrimethoxysilane (PTMS), polymethyl methacrylate (PMMA), Parylene C, liquid polyimide, laminated polyimide, polyimide, Kapton, black epoxy, polyether ketone (PEEK), Liquid Crystal Polymer (LCP), or any other suitable biocompatible coating.

Figure 20A:
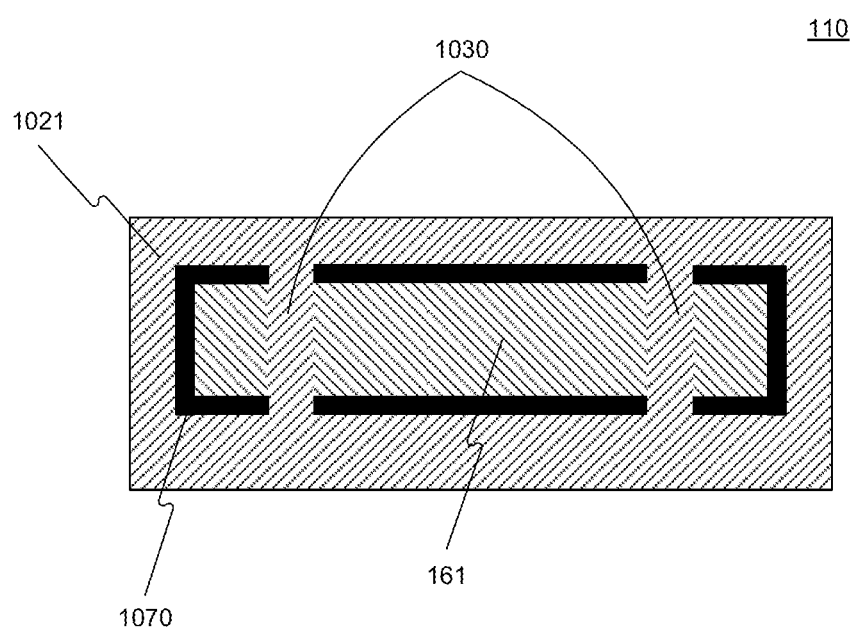
FIG. 20a provides a diagrammatic side sectional view of the implant unit encapsulation, according to an exemplary disclosed embodiment.

FIG. 20a illustrates polymer material having a density less than a density of a polymer material used to form secondary capsule 1070. For example, in some embodiments, primary capsule 1021 may include silicone, polyurethane, epoxy, acrylic, etc., and secondary capsule 1070 may include parylene N, parylene C, parylene HD, parylene D, etc. Additionally, other embodiments may include an outer barrier 1022 formed over the primary capsule 1021. The outer barrier 1022 (FIG. 20c) may serve as a moisture barrier or may be selected to provide other desired properties. For example, in some embodiments the outer barrier 1022 may be formed of a polymer having a density greater than the density of the primary capsule 1021. The outer barrier 1022 may be formed of parylene, for example.

Secondary capsule 1070 may provide environmental protection for the implant unit 110 when it is implanted in the body. For example, primary capsule 1021 may be constructed of silicone, which may be subject to moisture incursion from the body. Such moisture incursion may limit a life-span of the implant unit 110 due to possible corrosive effects. Secondary capsule 1070 may be provided underneath the primary capsule 1021 to protect implant unit 110 from the corrosive effects of bodily implantation. For example, a layer of parylene may serve as a secondary capsule and may be provided to encapsulate all or some of the components of implant unit 110.

In exemplary embodiments, secondary capsule 1070 may encapsulate any or all components associated with implant unit 110 and may fully or partially cover those components. For example, secondary capsule 1070 may cover the substrate, secondary antenna 152, carrier 161, implantable circuit 180, and electrodes 158a, 158b. The secondary capsule 1070 may, in turn, be encapsulated by primary capsule 1021.

Figure 20B:
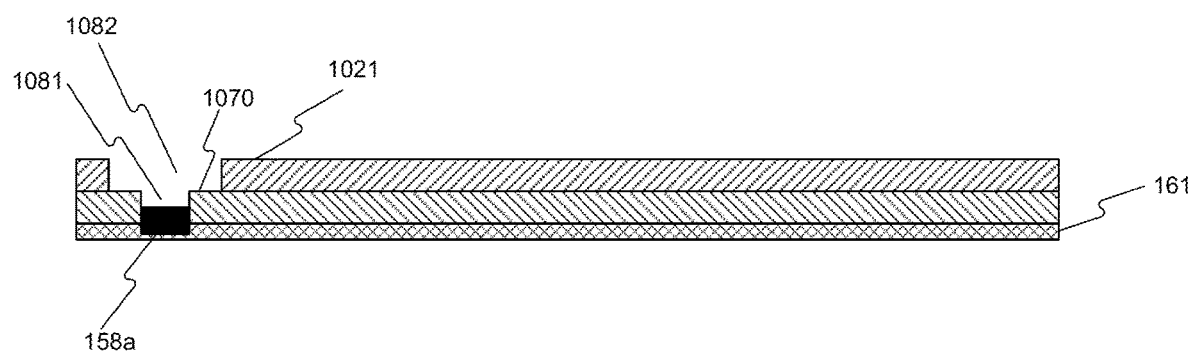
FIG. 20b illustrates a first and second window of exposure of the implant unit encapsulation, according to an exemplary disclosed embodiment.
Figure 20C:
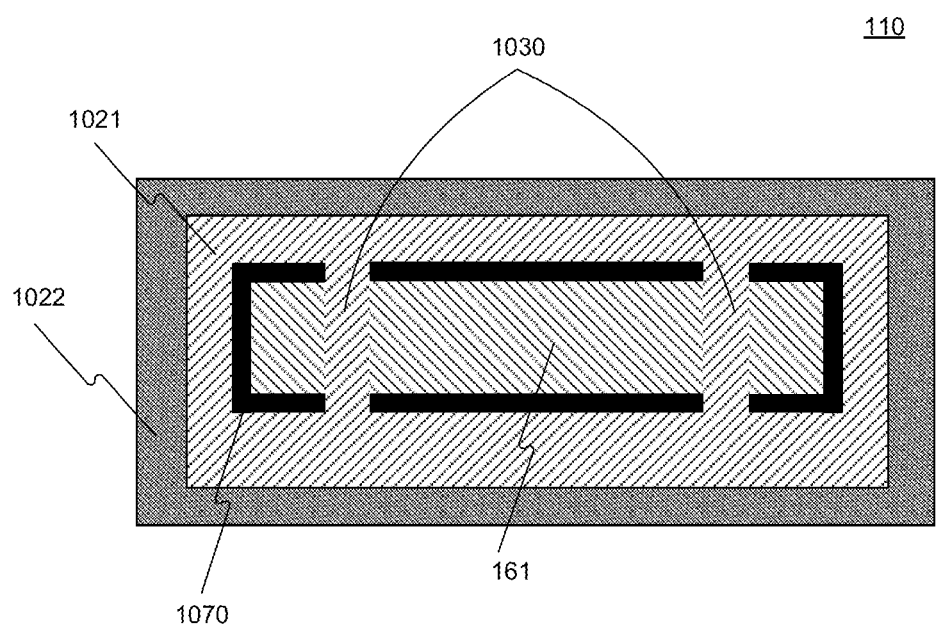
FIG. 20c provides another diagrammatic side sectional view of the implant unit encapsulation, according to an exemplary disclosed embodiment.

In some embodiments, secondary capsule 1070 may cover less than all of the components of implant unit 110. For example, in some embodiments, at least a portion of electrode 158a and/or 158b may remain uncovered by secondary capsule 1070. Similarly, as noted above, portions of electrode 158a and/or 158b may remain uncovered by primary capsule 1021. In some embodiments, as illustrated in FIG. 20b, a secondary window of exposure 1081 through secondary capsule 1070 may be smaller than a primary window of exposure 1082 through primary capsule 1021. Thus, from a perspective above electrode 158a, for example, an exposed lip of material associated with secondary capsule 1070 the edge of which forms the secondary window of exposure 1081 through secondary capsule 1070 would extend beyond a boundary of the primary window of exposure 1082 through primary capsule 1021.

Secondary capsule 1070, may include, for example parylene, parylene C or any other suitable material for preventing the effects of moisture incursion on implant unit 110. In some embodiments, a secondary capsule layer 1070 may be deposited by chemical vapor deposition and may have a thickness of about 1 molecule in thickness, between 1 and 5 molecules in thickness, or any other suitable film thickness.

Some combinations of primary and secondary capsule materials, such as silicone and parylene C, may bond relatively weakly to one another. Where such combinations of materials are used, a plurality perforations or penetrating holes 1030 (FIG. 20a) may be provided to pass through both carrier 161 and a secondary capsule 1070 to improve the adherence of the primary capsule 1021 to implant unit 110. For example, when penetrating holes 1030 are provided, the material of primary capsule 1021 may flow through the penetrating holes during fabrication, permitting the material of primary capsule 1021 to flow into and adhere to itself. A plurality of penetrating holes 1030 provided through carrier 161 and a secondary capsule 1070 may provide anchor points to permit the self-adherence of the material used to form primary capsule 1021. Penetrating holes 1030 may be provided and sized such that, after encapsulation by primary capsule 1021, at least some portion of holes 1030 remain free of primary capsule material, or they may be provided and sized such that, after encapsulation, holes 1030 are filled in (as illustrated in FIG. 20a).

Also illustrated in FIG. 10 are suture holes 1050, 1062 and 1064, which may include encapsulated surgical mesh 1064 therein. Suture holes 1050 may provide a larger target area for surgeons to use when suturing implant unit 110 into place during implantation. The entire suture holes 1050 may be encapsulated by primary capsule 1021 and may permit a surgeon to pass a needle through any portion of the suture holes without compromising the integrity of implant unit 110. Surgical mesh 1064 may be used to cover suture holes 1050, permitting larger suture holes 1050 that may provide surgeons with a greater target area. Surgical mesh 1064 may also encourage surrounding tissue to bond with implant unit 110. In some embodiments, a surgeon may pass a surgical suture needle through suture holes 160, located on one extension 162a of an elongate arm 162 of implant unit 110, through tissue of the subject, and through surgical mesh 1064 provided on a second extension 162b of elongate arm 162 of implant unit 110. In this embodiment, the larger target area provided by suture holes 1050 may facilitate the suturing process because it may be easier to locate a larger suture hole after a suture needle passes first through a suture hole in extension 162a and subsequently passes through tissue in the subject's body.

The primary and secondary capsules may be provided such that implant unit 110 remains flexible after encapsulation. Implant unit 110 may include one or more additional features to allow components of implant unit 110 to bend and flex with flexible carrier 161. For example, implant unit 110 can include meandering electrical traces 1060.

For purposes of this disclosure, the term "electrical trace" generally refers to a conductive element such as, for example, a lead, a wire, a cable, a ribbon, or other conductive component. The phrase "meandering electrical trace" generally refers to an electrical trace that is longer than the shortest distance between the electrical components that it connects and includes one or more features designed to lengthen the electrical trace for a purpose other than routing of the electrical trace around various circuit elements. In conventional implanted units, repeated bending, twisting or stretching of the carrier can cause degradation of the electrical traces, as they are repeatedly stressed with the flexure of carrier 161. The configuration of the disclosed meandering electrical traces 1060 on flexible carrier 161 may increase the lifetime of the traces and, consequently, the implant 110.

Meandering electrical traces 1060 may be formed of any suitable conductive material. Such materials may include metals including gold, platinum, titanium, copper, silver, iridium, platinum-iridium, platinum-gold, etc. Additionally and/or alternatively, meandering electrical traces 1060 may be formed of conductive polymer materials including polyacetylene, polypyrrole, and polyaniline. Meandering electrical traces 1060 may also be composed of metal-polymer composites or any other biocompatible conductive material or combinations of materials. Meandering electrical traces 1060 may have any cross-sectional shape and may have any desired dimension, including thickness, suitable for assembly in implant unit 110 on flexible carrier 161.

Meandering electrical traces 1060 may be located on any portion of flexible carrier 161, and may be configured to establish electrical communication (i.e., a direct or indirect electrical connection) between any two or more electrical components of implant unit 110. In the exemplary embodiment shown in FIG. 10, implant unit 110 includes two meandering electrical traces 1060 located on first extension 162a of elongate arm 162. Each meandering electrical trace 1060 may be configured to provide an electrical connection between implant circuitry 180 and an implant electrode. For example, one meandering electrical trace 1060 may be configured to provide an electrically conductive path between implant circuitry 180 and implant electrode 158a, and the other meandering electrical trace 1060 may be configured to provide an electrically conductive path between implant circuitry 180 and implant electrode 158b.

Although the depicted embodiment includes two meandering electrical traces 1060, implant 110 may include a greater or lesser number of electrical traces 1060. For example, FIG. 10 illustrates an alternative embodiment of implant 110 having a plurality of electrodes located, for example, at the ends of first extension 162a and second extension 162b. In this embodiment, multiple meandering electrical traces may be provided. The multiple meandering electrical traces may be located on both first extension 162a and second extension 162b. A meandering electrical trace may be provided between each electrode and implant circuitry 180.

Figure 21:
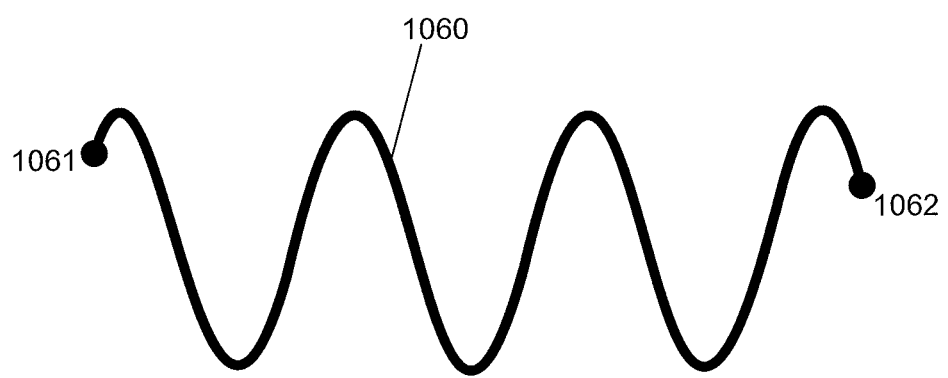
FIG. 21 illustrates meandering traces consistent with the present disclosure.

Referring to FIG. 21, each meandering electrical trace 1060 may include a first contact point 1061 and a second contact point 1062. First contact point 1061 may be associated with an implant electrode, as discussed above. Second contact point 1062 may be associated with implant circuitry 180, similarly discussed above.

Meandering electrical traces may be of sufficient length so as to maintain electrical conductivity with implant circuit 180 and implant electrodes 158, 158b via first contact point 1061 and second contact point 1062 during flexing of flexible carrier 161. More particularly, meandering electrical trace 1060 may have a length that is longer than the shortest distance between first contact point 1061 and second contact point 1062. For example, in some embodiments, the meandering electrical trace may have a length that is at least 50%, 100%, 200%, 500% or more of a distance between two contacts that the electrical trace connects.

In some embodiments, meandering electrical traces 1060 may include path shapes including successive curves or wave-like shapes. In this configuration, slack in the trace may reduce stress on the trace during flexing of carrier 161. The configuration of each meandering electrical trace 1060, including the length and the number of successive waves, bends, etc., may be based on, for example, the configuration (e.g., shape and size) of the carrier, the location of implant electrodes 158a, 158b on the carrier, and the location of implant electrodes 158a, 158b relative to implant circuitry 180.

Meandering electrical trace 1060 may be formed with any suitable path shape. For example, in the exemplary embodiment of FIG. 21, meandering electrical trace 1060 may include a path shape resembling a sine wave. It is contemplated that the traces can also include other shapes such as a square wave-like shape, rectangular wave-like shape, triangular wave-like shape, complex wave-like shape, ramped wave-like shape, and/or a sawtooth wave-like shape, etc. Multiple meandering electrical traces 1060 may have the same or different waveforms. Additionally, undulations in the path shape of meandering trace 1060 may be regular (e.g., all features including substantially the same size and shape) or may be irregular (e.g., one or more of the features having a size and/or shape that differs from at least one other feature).

The amplitude and distance between each wave-like shape of a meandering electrical trace 1060 may vary. For example, some or all of the wave-like shapes may have the same amplitude and/or periodic, regular spacing. In other embodiments, some or all of the wave-like shapes may have different amplitudes and/or spacings relative to one another. The amplitude and/or wavelength of the wave-like shapes may be dependent on, for example, the distance between the two electrical components connected by meandering electrical trace 1060, and the flexibility and material encapsulating the portion of the carrier on which it is located. Increasing the amplitude and/or decreasing the wavelength of the waveforms may have the effect of increasing the flexibility of meandering electrical trace 1060, and consequently, reducing the stress on the trace during repeated flexing.

In some embodiments, meandering trace 1060 may be formed within a trench on flexible carrier 161 and may be held within the trench, at least partially, by mechanical interaction with walls of the trench. This configuration may allow the meandering trace to slip within the trench during flexing of the flexible carrier. Further, the added length of the meandering trace offered by the undulations included in the trace may allow meandering trace 1060 to behave similar to a spring during flexing of flexible carrier 161. In this manner, meandering trace 1060 may be resistant to cracking, breakage, or fatigue caused by flexing of flexible carrier 161.

Referring back to FIG. 10, conductive electrical elements of implant unit 110, such as meandering traces 1060 and electrodes 158a, 158b may be provided through a progressive metallization layering method. In some embodiments, flexible carrier 161 may include a material, such as liquid crystal polymer, that bonds relatively weakly to conductive metals desirable for use as conductive electrical elements, such as titanium and/or gold. A progressive metallization layering method may utilize a temporary bonding layer, including a metal, such as nickel, that may bond more strongly to flexible carrier 161. The temporary bonding layer may be layered with the metals desirable for use as conductive electrical elements and used to provide an initial bond with the material of flexible carrier 161. The temporary bonding layer may then be removed through dissolution, erosion, or similar technique, through flexible carrier 161, leaving the desirable metals in place in flexible carrier 161.

In one embodiment, a progressive metallization layering method may be utilized to provide gold and titanium conductive elements on a liquid crystal polymer carrier 161. The conductive elements may be constructed from progressive layers of nickel, gold, and titanium. Next, liquid crystal polymer may be molded around the conductive elements, bonding strongly with the nickel layer and forming a recess containing the layered conductive element. Finally, the nickel may be removed through the liquid crystal polymer through dissolution, erosion, or similar technique. The removal of nickel leaves the gold/titanium layered conductive element in place, held tightly in the liquid crystal polymer recess created during the molding process.

Returning to FIGS. 2 and 3, external unit 120 may be configured to communicate with implant unit 110. For example, in some embodiments, a primary signal may be generated on primary antenna 150, using, e.g., processor 144, signal source 142, and amplifier 146. More specifically, in one embodiment, power source 140 may be configured to provide power to one or both of the processor 144 and the signal source 142. The processor 144 may be configured to cause signal source 142 to generate a signal (e.g., an RF energy signal). Signal source 142 may be configured to output the generated signal to amplifier 146, which may amplify the signal generated by signal source 142. The amount of amplification and, therefore, the amplitude of the signal may be controlled, for example, by processor 144. The amount of gain or amplification that processor 144 causes amplifier 146 to apply to the signal may depend on a variety of factors, including, but not limited to, the shape, size, and/or configuration of primary antenna 150, the size of the patient, the location of implant unit 110 in the patient, the shape, size, and/or configuration of secondary antenna 152, a degree of coupling between primary antenna 150 and secondary antenna 152 (discussed further below), a desired magnitude of electric field to be generated by implant electrodes 158a, 158b, etc. Amplifier 146 may output the amplified signal to primary antenna 150.

External unit 120 may communicate a primary signal on primary antenna 150 to the secondary antenna 152 of implant unit 110. This communication may result from coupling between primary antenna 150 and secondary antenna 152. Such coupling of the primary antenna 150 and the secondary antenna 152 may include any interaction between the primary antenna 150 and the secondary antenna 152 that causes a signal on the secondary antenna 152 in response to a signal applied to the primary antenna 150. In some embodiments, coupling between the primary and secondary antennas 150, 152 may include capacitive coupling, inductive coupling, radiofrequency coupling, etc. and any combinations thereof.

Coupling between primary antenna 150 and secondary antenna 152 may depend on the proximity of the primary antenna 150 relative to the secondary antenna 152. That is, in some embodiments, an efficiency or degree of coupling between primary antenna 150 and secondary antenna 152 may depend on the proximity of the primary antenna 150 to the secondary antenna 152. The proximity of the primary and secondary antennas 150, 152 may be expressed in terms of a coaxial offset (e.g., a distance between the primary and secondary antennas when central axes of the primary and secondary antennas are co-aligned), a lateral offset (e.g., a distance between a central axis of the primary antenna and a central axis of the secondary antenna), and/or an angular offset (e.g., an angular difference between the central axes of the primary and secondary antennas). In some embodiments, a theoretical maximum efficiency of coupling may exist between primary antenna 150 and secondary antenna 152 when both the coaxial offset, the lateral offset, and the angular offset are zero. Increasing any of the coaxial offset, the lateral offset, and the angular offset may have the effect of reducing the efficiency or degree of coupling between primary antenna 150 and secondary antenna 152.

As a result of coupling between primary antenna 150 and secondary antenna 152, a secondary signal may arise on secondary antenna 152 when the primary signal is present on the primary antenna 150. Such coupling may include inductive/magnetic coupling, RF coupling/transmission, capacitive coupling, or any other mechanism where a secondary signal may be generated on secondary antenna 152 in response to a primary signal generated on primary antenna 150. Coupling may refer to any interaction between the primary and secondary antennas. In addition to the coupling between primary antenna 150 and secondary antenna 152, circuit components associated with implant unit 110 may also affect the secondary signal on secondary antenna 152. Thus, the secondary signal on secondary antenna 152 may refer to any and all signals and signal components present on secondary antenna 152 regardless of the source.

While the presence of a primary signal on primary antenna 150 may cause or induce a secondary signal on secondary antenna 152, the coupling between the two antennas may also lead to a coupled signal or signal components on the primary antenna 150 as a result of the secondary signal present on secondary antenna 152. A signal on primary antenna 150 induced by a secondary signal on secondary antenna 152 may be referred to as a primary coupled signal component. The primary signal may refer to any and all signals or signal components present on primary antenna 150, regardless of source, and the primary coupled signal component may refer to any signal or signal component arising on the primary antenna 150 as a result of coupling with signals present on secondary antenna 152. Thus, in some embodiments, the primary coupled signal component may contribute to the primary signal on primary antenna 150.

Implant unit 110 may be configured to respond to external unit 120. For example, in some embodiments, a primary signal generated on primary coil 150 may cause a secondary signal on secondary antenna 152, which in turn, may cause one or more responses by implant unit 110. In some embodiments, the response of implant unit 110 may include the generation of an electric field between implant electrodes 158a and 158b.

FIG. 6 illustrates circuitry 170 that may be included in external unit 120 and circuitry 180 that may be included in implant unit 110. Additional, different, or fewer circuit components may be included in either or both of circuitry 170 and circuitry 180. As shown in FIG. 6, secondary antenna 152 may be arranged in electrical communication with implant electrodes 158a, 158b. In some embodiments, circuitry connecting secondary antenna 152 with implant electrodes 158a and 158b may cause a voltage potential across implant electrodes 158a and 158b in the presence of a secondary signal on secondary antenna 152. This voltage potential may be referred to as a field inducing signal, as this voltage potential may generate an electric field between implant electrodes 158a and 158b. More broadly, the field inducing signal may include any signal (e.g., voltage potential) applied to electrodes associated with the implant unit that may result in an electric field being generated between the electrodes. Energy transfer between primary antenna 150 and secondary antenna 152 via the primary signal may be improved when a resonant frequency of primary antenna 150 and its associated circuitry 170 matches that of secondary antenna 152 and its associated circuitry 180. As used herein a resonant frequency match between two antennas may be characterized by the proximity of two resonant frequencies to one another. For example, a resonant frequency match may be considered to occur when two resonant frequencies are within 30%, 20%, 10%, 5%, 3%, 1%, 0.5%, 0.1%, or less of each other. Accordingly, a resonant frequency mismatch may be considered to occur when two resonant frequencies do not match. The proximity of the two resonant frequencies required to be considered a match may depend on the circumstances of energy transfer between the two antennas. A resonant frequency match between two antennas may also be characterized by the efficiency of energy transfer between the antennas. The efficiency of energy transfer between two antennas may depend on several factors, one of which may be the degree to which the resonant frequencies of the antennas match. Thus, if all other factors are held constant, changing the resonant frequency of one antenna with respect to the other will alter the efficiency of energy transfer. A resonant frequency match between two antennas may be considered to occur when the efficiency of energy transfer is within 50% or greater of a maximum energy transfer when all other factors remain constant. In some embodiments, a resonant frequency match may require energy transfer efficiencies of 60%, 70%, 80%, 90%, 95% or greater.

Several embodiments are provided in order to appropriately match resonant frequencies between a primary signal and a secondary antenna 152. Because the secondary antenna 152 is intended for implantation with implant unit 110, it may be difficult to adjust the resonant frequency of the antenna during use. Furthermore, due to the possibility of moisture incursion into primary capsule 1201 encapsulating implant unit 110, implant circuitry 180, and secondary antenna 152, a resonant frequency of the implant unit 110 may drift after implantation. Other factors present during implantation may also influence the frequency drift of implant unit 110 after implantation. This drifting of the resonant frequency may last for several days to several months after implantation before stabilizing. For example, the resonant frequency of an implant unit 110 may drift from 8.1 kHz to 7.9 kHz. Through experimentation or simulation, it may be possible to predict by how much the resonant frequency may drift. Thus, using the example above, if a long term resonant frequency value of 7.9 kHz is desired, an implant unit 110 may be manufactured with a resonant frequency value of 8.1 kHz prior to implantation.

Resonant frequency values of manufactured implant units 110 may be adjusted during the manufacturing process through the use of at least one trimming capacitor. In one embodiment, carrier 161 may be manufactured with all or some of the components of the final implant unit, including, for example, secondary antenna 152, implant circuitry 180, modulation electrodes 158a, 158b. The resonant frequency of this assembly may then be measured or otherwise determined. Due to variations in manufacturing processes and materials, the resonant frequency of each manufactured unit may differ. Thus, in order to meet a specific resonance frequency, each implant unit may be adjusted through the addition of one or more trimming capacitors to the implant circuitry 180 prior to encapsulation. In one embodiment, a capacitor may be laser trimmed to an exact capacitance value before insertion into implant circuitry 180. In another embodiment, a stock capacitor of known value may be inserted into implant circuitry 180. In still another embodiment, a plurality of capacitors may be inserted into implanted circuitry 180 to appropriately adjust the resonant frequency of implant unit 110. Such a plurality of capacitors may include a series of capacitors having progressively smaller capacitance values, and a resonant frequency of the assembly may be measured after the insertion of each capacitor prior to choosing and inserting the next. In this fashion, implantable circuit 180 may include at least one capacitor configured to create a predetermined mismatch between a resonant frequency of implantable circuit 180 and external circuit 170.

Knowing the expected resonant frequency drift, the resonant frequency of the implant unit may be set, for example, by adjusting a capacitance associated with the implantable circuit. In one embodiment, a capacitor associated with the implantable circuit may be adjusted (e.g., laser trimmed) to an particular capacitance value before insertion into implant circuitry. In another embodiment, a capacitor of known value may be inserted into implant circuitry. In still another embodiment, a plurality of capacitors may be inserted into the implanted circuitry to set the capacitance of the implantable circuit and to adjust the resonant frequency of the implant unit. Such a plurality of capacitors may include a series of capacitors each having at least one capacitance value that may be the same or different. The resonant frequency may be calculated based on a particular capacitance value. Alternatively, the resonant frequency value may be iteratively determined after capacitance adjustments. For example, after an adjustment in capacitance, a resulting resonant frequency may be measured. If the resonant frequency has a desired value, then no further adjustments may be necessary. Otherwise, the process of adjusting and measuring may continue iteratively until a desired or target resonant frequency is obtained.

In some embodiments, as discussed above, the capacitance associated with the implantable circuit may be determined such that after the implant unit is placed in the body and after an expected level of resonant frequency drift, the internal resonant frequency of the implantable circuit and the external resonant frequency of the external circuit may be in resonant frequency match. The expected level of drift may be determined through calculations. Alternatively or additionally, the expected level of drift may be determined through testing.

Some embodiments may include methods for manufacturing an implant unit. For example, an implantable circuit may be arranged on a carrier, and an antenna may be arranged on the carrier. The antenna may include an antenna configured to wirelessly receive energy from an external unit and to transfer at least a portion of the received to the implantable circuit. The method may also include determining an expected level of resonant frequency drift for the implant unit and adjusting a capacitance associated with the implantable circuit such that the implant unit, including the secondary antenna and the implantable circuitry, includes a target resonant frequency. A difference between the target resonant frequency and the resonant frequency of the external unit (e.g., including the primary antenna and associated circuitry) may be close to, substantially equal to, or equal to the amount of expected resonant frequency drift experienced by the implant unit after implantation into the body.

In addition to resonant frequency drift in implant unit 110, a resonant frequency of primary antenna 152 may vary temporally due, for example, to changing environmental conditions. For example, the application of the antenna 152 to the skin of a subject may cause bending of the primary antenna 152 to conform to the skin of a subject. Such bending may cause a shift in the spatial relationship among coils within primary antenna 152, which may lead to a change in resonant frequency. Other factors associated, e.g., with the condition of the subject's skin (e.g., moisture, sweat, oil, hair, etc.) may also change over time and may contribute to a change in resonant frequency of the primary antenna 152. The temporal variance in resonant frequency of primary antenna may be between 0-5%, up to 10%, or up to 20% or more. Thus, a current resonant frequency of the primary antenna 152 (e.g., a resonant frequency exhibited by the primary antenna or a circuit including the primary antenna at a particular point in time or over a time duration) may be adjusted to counter effects of changing environmental conditions as well as to match frequencies with a resonant frequency of an implantable circuit 180.

Processor 144 of the external unit may be configured to determine a resonant frequency mismatch between an external circuit 170 associated with primary antenna 152 and an implantable circuit 180 associated with secondary antenna 150 and adjust a resonant frequency of the external circuit 170 associated with primary antenna 152 in order to reduce or eliminate the resonant frequency mismatch. During transmission of a primary signal from a primary antenna to a secondary antenna, processor 144 may be configured to determine a resonant frequency mismatch based on a primary coupled signal component present on the primary antenna due coupling between primary antenna 152 and secondary antenna 150. Monitoring a primary coupled signal component by the processor 144 may provide an indication of transmission efficiency, which may in turn be an indication of resonant frequency mismatch. The primary coupled signal component and the interaction between primary antenna 152 and secondary antenna 150 are explained in greater detail below.

Upon determining a resonant frequency mismatch between an external circuit 170 associated with primary antenna 152 and an implantable circuit 180 associated with secondary antenna 150, processor 144 may adjust the resonant frequency of the external circuit 170 to reduce the mismatch. A resonance matching unit 190 may be in electrical communication with the external circuit 170 to facilitate the alteration of the resonant frequency of the external circuit 170. The circuit formed between the external circuit 170 and the resonance matching unit 190 may include an adjustable resonance circuit 191. Such alteration may be performed, for example, through the selective inclusion or exclusion of at least one capacitor into or out of the adjustable resonance circuit 191 formed between the external circuit 170 and the resonance matching unit 190. Adding (or subtracting) capacitors in resonance matching unit 190 may cause a change in the resonant frequency of the adjustable resonance circuit 191. Resonance matching unit 190 may be provided with one or more trim capacitors configured, through processor 144 controlled switches, for selective inclusion and exclusion. The switches may include, for example, transistors or relays. Thus, processor 144 may include or exclude a capacitor adjustable resonance circuit 191 by opening or closing a switch associated with the respective capacitor. Providing a single capacitor, therefore, permits processor 144 to switch the resonant frequency of the adjustable resonance circuit 191 between two different values. In an exemplary embodiment, a bank of six capacitors may be provided, permitting processor 144 to switch the resonant frequency of the adjustable resonance circuit 191 between 64 (i.e., $2^6$) different values. In alternative embodiments, more or fewer capacitors may be provided for adjusting the resonant frequency of the adjustable resonance circuit 191 to reduce the mismatch.

In an exemplary embodiment, processor 144 may be configured to switch capacitors from a capacitor bank into and out of the adjustable resonance circuit 191 during transmission of a primary signal to determine a capacitor combination that changes (e.g., increases) transmission efficiency and resonant frequency match. In some embodiments, processor 144 may be configured to select an optimal combination of capacitors to provide a best resonant frequency match. In some embodiments, processor 144 may be configured to select an optimal combination of capacitors, based on a detected magnitude of the power transmitted to the implant unit. In alternative embodiments, processor 144 may be configured to select a combination of capacitors that provides a resonant frequency match surpassing a predetermined threshold, regardless of whether such combination produces an optimal resonant frequency match.

Resonant frequency matching between a primary antenna 150 and a secondary antenna 152 may increase the efficiency of energy transfer between the antennas. In additional embodiments, external unit 120 may be provided with features that may facilitate development of a match between a frequency of a primary signal and a resonant frequency of the external circuit 170 associated with primary antenna 150. Development of such a match may further increase the efficiency of external unit 120. Some conventional amplifiers may be configured to generate a signal at a single frequency. Using such an amplifier may create a mismatch between the signal generated by the amplifier and the resonant frequency of the adjustable resonance circuit 191 when the adjustable resonance circuit 191 is adjusted to match frequencies with an implant unit 110. Thus, in some embodiments, self-resonant circuits may be provided for use with a resonance matching unit 190, as further described below with respect to FIGS. 7 and 8.

Figure 16:
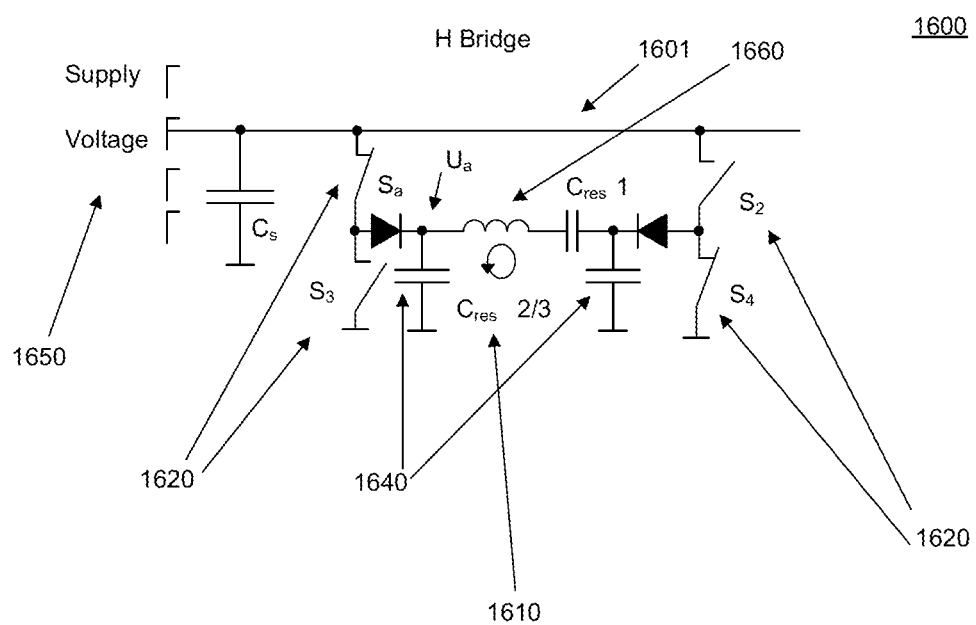
FIG. 16 depicts a self-resonant transmitter employing a modified class D amplifier.

FIG. 16 depicts an embodiment illustrating a self-resonant transmitter circuit employing a modified class D amplifier for use with resonant frequency matching methods. Modified class D amplifier 1600 may be used in place of, or in addition to, any or all of the elements of external unit 120 depicted in FIG. 3. For example, modified class D amplifier 1600 may replace signal source 142 and amplifier 146. In this embodiment, processor 144 may be configured to adjust the operation of a class D amplifier to provide a frequency match between a generated signal and a resonant frequency of an adjustable resonance circuit 191. Because the resonant frequency adjustable resonance circuit 191 may be adjusted to match that of implanted circuit 180 associated with secondary antenna 152 during operation, it may be beneficial to adjust the frequency of the generated signal as well to improve efficiency within the adjustable resonance circuit 191 external unit 120. Modified class D amplifier 1600 may be used to provide such an adjustment as follows. Modified class D amplifier 1600 includes an H bridge 1601 including switches (such as MOSFETs) 1620. Between the switches, an adjustable resonance transmitter circuit 1610 may be provided. Power to the modified class D amplifier may be provided by supply 1650, which may include a battery, for example. Adjustable resonance transmitter circuit 1610 may include adjustable resonance circuit 191. Thus, adjustable resonance transmitter circuit 1610 may include at least a primary antenna 150 and a resonance matching unit 190. FIG. 16 illustrates an exemplary self-resonant transmitter circuit 1610, depicting multiple capacitances 1640 and inductances 1660. In some embodiments, resonance matching unit 190 may take the place of some or all of capacitances 1640. In some embodiments, adjustable resonance transmitter circuit 1610 may include a primary antenna 150, and thus inductance 1660 may include the inductance of antenna 150. Capacitances 1640 may include multiple capacitors, combinations of which may be chosen from among trim capacitors as described above, in order to selectively provide an appropriate value of capacitance 1640. The value of capacitance 1640 may be selected for resonant frequency matching to adjustable resonance circuit 191. Inductances 1660 may be provided at least partially by primary antenna 150. Processor 144 may also adjust a driving frequency of the H bridge switches 1620 in order to generate a signal of a frequency that matches the resonant frequency of self-resonant circuit 1610. By selectively opening and closing switches 1620 appropriately, the DC voltage signal of supply 1650 may be converted into a square wave of a selected frequency. This frequency may be selected to match the resonant frequency of adjustable resonance circuit 1610 in order to change (e.g., increase) the efficiency of the circuit.

Figure 17:
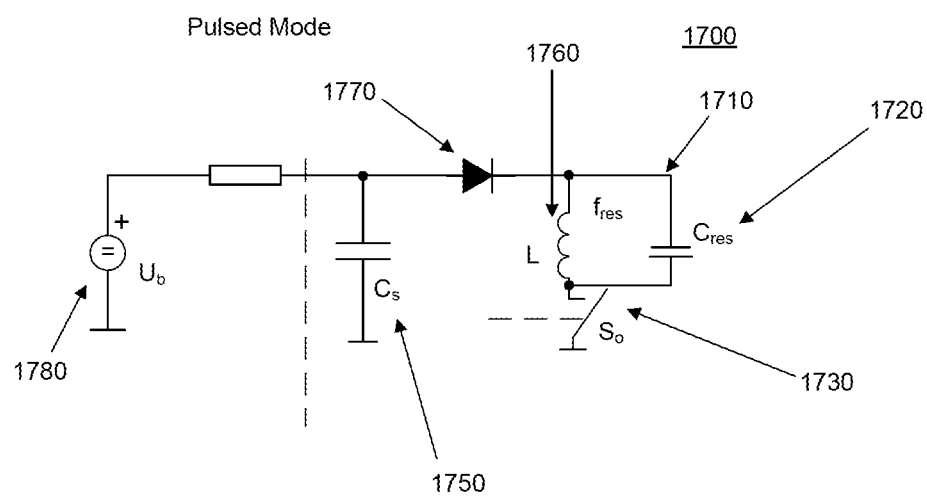
FIG. 17 depicts a pulsed mode self-resonant transmitter.

FIG. 17 depicts an additional embodiment illustrating a pulsed mode self-resonant transmitter 1700 for use with resonant frequency matching methods. Pulsed mode self-resonant transmitter 1700 may be used in place of, or in addition to, any or all of the elements of external unit 120 depicted in FIG. 3. For example, pulsed mode self-resonant transmitter 1700 may replace signal source 142 and amplifier 146. In this embodiment, processor 144 may be configured to control the circuit through a power release unit, depicted in the present embodiment as switch 1730. A power release unit may include a transistor, relay, or similar switching device. Pulsed mode self-resonant transmitter 1700 may include a primary power source 1780, for example, a battery or alternative source of power. Transmitter 1700 may include a power storage unit, such as storage capacitor 1750. Other suitable power storage units may also be utilized, such as an inductor and/or battery, as well as combinations of these storage elements. Transmitter 1700 may also include a self-resonant transmitter circuit 1710, including resonance capacitance 1720 and a resonance inductance 1760. Resonance inductance 1760 may be provided at least partially by primary antenna 150.

Transmitter 1700 may operate in the following manner, among others. Processor 144 may be configured to control the power release unit, illustrated in FIG. 8 as switch 1730. Processor 144 may be configured to control a mode of operation of the power release unit such that in a first mode of operation the power storage unit receives power from the power source, and in a second mode of operation, the power storage unit releases power to the antenna to cause an oscillation in the primary antenna at a resonance frequency.

For example, in a first mode of operation, the power storage unit, for example, storage capacitor 1750, may be configured to store energy from power source 1780. When switch 1730 is maintained in an open position, or a first state, current from power source 1780 may flow into storage capacitor 1750 which thereby stores energy by accumulating electrical charge.

The power release unit may be configured to cause the release a pulse of energy from the power storage unit to primary antenna 150 after the power storage unit has accumulated certain amount electrical charge. In a second mode of operation, when switch 1730 is closed, or moved to a second state, charged storage in capacitor 1750 drives current into the self-resonant circuit 1710 during a current loading period, where energy is stored in inductance 1760. Due to the operation of diode 1770, current flow into circuit 1710 will be cut off after a period of energy accumulation. The current transferred to circuit 1710 will then oscillate freely within circuit 1710 at the resonant frequency of circuit 1710 and thus generate a signal for transmission to the implant through primary antenna 150 (which is included in the circuit and creates at least a portion of inductance 1760). During this free oscillation period, the amplitude of the oscillations may diminish at a rate determined by the components of circuit 1710. When the oscillations have diminished to a desired level, for example, to between 5% and 10%, between 10% and 50%, or between 50% and 90% of an initial amplitude, switch 1730 may be closed again to permit storage capacitor 1750 to enter a current loading period again. During the free oscillation period, oscillation amplitude may be measured, for example, by processor 144 to determine the appropriate operation of switch 1730. In some embodiments, a current loading period may be between 0.5 and 10 μs, or between 2 and 5 μs. In some embodiments, a free oscillation period may be between 10 and 30 μs. Switch 1730 may be opened and closed several times in order to maintain a desired level of current flow in circuit 1710 for a desired period of time by assembling a series of current loading period and free oscillation periods. The desired period of time may correspond to a sub-pulse of a stimulation control signal, discussed in greater detail below. The operation of switch 1730 may be adjusted by processor 144 to increase the efficacy of modulation signals generated in implant unit 110. Such adjustments may be based, for example, on feedback received from implant unit 110, as discussed herein.

Storage capacitor 1750 may be selected to store enough energy for a complete stimulation sub-pulse, which may be, for example, between 50 and 250 μs, or between 1 μs and 2 ms. After delivery of a stimulation sub-pulse, switch 1730 may be closed again in order to permit storage capacitor 1750 to accumulate energy from power source 1780. Such accumulation may occur, for example, over a time period of between 5 and 50 milliseconds. Energy accumulated over this accumulation period may be, for example, between 1 microjoule and 10 millijoules.

Storage capacitor 1750 may be selected so as to have characteristics permitting the current in circuit 1710 to rise to a desired level at a desired rate. In some embodiments, the capacitor 1750 may be selected such that the current in circuit 1710 may change rapidly to permit a corresponding rapid increase in transmission power. For example, capacitor 1750 may be selected so as to permit the current in circuit 1710 to rise to a desired value, (e.g. between 100 mAmps and 1 Amp) during the current loading period. In some embodiments, capacitor 1750 may be selected such that a maximum value of current in circuit 1710 is higher than may be possible using power source 1780 alone. For example, capacitor 1750 may be selected so as to drive a current in circuit 1710 that is 5, 10, 20, or 100 times greater than may be permitted through the use of power source 1780 alone. For example, by utilizing the pulsed mode resonant transmitter, a battery having a voltage between 3 and 6 volts used as power source 1780 may yield a voltage in circuit 1710 of between 300 and 600 volts. Suitable capacitors may be chosen in the range of 1 microfarad to 100 microfarads.

Circuit 1710 may be configured so as to permit a power storage unit to release a desired portion of its stored energy in a desired time period—i.e. the current loading period as described above. For example, circuit 1710 may be configured to permit a power storage unit, such as storage capacitor 1750 to release between 1% and 10% of its accumulated charge in a time period between 1 and 10 microseconds.

Because the signal for transmission is generated by the self-resonance of circuit 1710, it has a frequency dictated by the resonant frequency of circuit 1710. Such an arrangement may offer more efficient transmission than configurations that drive a transmission circuit with a signal that does not match the resonant frequency of the transmission circuit. Generating a transmission signal in the manner described may minimize the risk of reductions in energy transfer efficiency caused by changes in resonance of the transmission circuit. As discussed above, such temporal resonance changes in the transmission circuit may range between 0-5%, up to 10%, up to 20% or more.

Components of transmitter 1700 may be chosen such that the current loading period is approximately two microseconds, and a period of free oscillation in circuit 1710 is between 10 and 20 microseconds. Other components may be selected, however, to provide any desired current loading period or free oscillation period. As described elsewhere in this disclosure, stimulation pulses of varying lengths may be desired. Stimulation pulses of longer than a single period of free oscillation may be constructed by multiple cycles of loading and releasing energy from storage capacitor 1750 into circuit 1710. Storage capacitor 1750 may itself be chosen to store enough charge to drive a large number of oscillation cycles (e.g. between 10 and 100) in order to construct entire stimulation pulses without requiring recharging from power source 1780.

In some embodiments, transmitter 1700 may be used in conjunction with resonance matching unit 190. As discussed above, due to changes in environmental conditions, a resonant frequency of circuit 1710 may vary. Processor 144 may be configured to cause delivery of an impulse of energy to circuit 1710, for example, via operation of a power release unit such as switch 1730. This impulse of energy may excite circuit 1710 and cause oscillations in circuit 1710 at the current resonant frequency of the external circuit such that power is delivered from primary antenna 150 to implant unit 110 at the current resonant frequency of the circuit 1710. Resonance matching unit 190 may be in electrical communication (e.g., direct or indirect electrical connection) with circuit 1710, and may be configured, under control of processor 144, to alter the current resonant frequency of the circuit formed by circuit 1710 and matching unit 190. Such alterations of the current resonant frequency may be performed, for example, to optimize transmission efficiency with implant unit 121.

Pulsed mode self-resonant transmitter 1700 may provide several advantages. As described above, because the transmission signal is generated by the self-resonance of circuit 1710, it likely will match the resonant frequency of circuit 1710, obviating a need to match the frequency of the generated signal with the circuit resonance frequency. Further, because energy is stored in capacitor 1750 prior to discharge into circuit 1710, a greater flexibility in choice of power source 1780 may be provided. Effective neural modulation by an implant unit may depend on current levels that rise rapidly.

Naturally functioning neurons function by transmitting action potentials along their length. Structurally, neurons include multiple ion channels along their length that serve to maintain a voltage potential gradient across a plasma membrane between the interior and exterior of the neuron. Ion channels operate by maintaining an appropriate balance between positively charged sodium ions on one side of the plasma membrane and negatively charged potassium ions on the other side of the plasma membrane. A sufficiently high voltage potential difference created near an ion channel may exceed a membrane threshold potential of the ion channel. The ion channel may then be induced to activate, pumping the sodium and potassium ions across the plasma membrane to switch places in the vicinity of the activated ion channel. This, in turn, further alters the potential difference in the vicinity of the ion channel, which may serve to activate a neighboring ion channel. The cascading activation of adjacent ion channels may serve to propagate an action potential along the length of the neuron. Further, the activation of an ion channel in an individual neuron may induce the activation of ion channels in neighboring neurons that, bundled together, form nerve tissue. The activation of a single ion channel in a single neuron, however, may not be sufficient to induce the cascading activation of neighboring ion channels necessary to permit the propagation of an action potential. Thus, the more ion channels in a locality that may be recruited by an initial potential difference, caused through natural means such as the action of nerve endings or through artificial means, such as the application of electric fields, the more likely the propagation of an action potential may be. The process of artificially inducing the propagation of action potentials along the length of a nerve may be referred to as stimulation, or up modulation.

Neurons may also be prevented from functioning naturally through constant or substantially constant application of a voltage potential difference. After activation, each ion channel experiences a refractory period, during which it "resets" the sodium and potassium concentrations across the plasma membrane back to an initial state. Resetting the sodium and potassium concentrations causes the membrane threshold potential to return to an initial state. Until the ion channel restores an appropriate concentration of sodium and potassium across the plasma membrane, the membrane threshold potential will remain elevated, thus requiring a higher voltage potential to cause activation of the ion channel. If the membrane threshold potential is maintained at a high enough level, action potentials propagated by neighboring ion channels may not create a large enough voltage potential difference to surpass the membrane threshold potential and activate the ion channel. Thus, by maintaining a sufficient voltage potential difference in the vicinity of a particular ion channel, that ion channel may serve to block further signal transmission.

The membrane threshold potential may also be raised without eliciting an initial activation of the ion channel. If an ion channel (or a plurality of ion channels) are subjected to an elevated voltage potential difference that is not high enough to surpass the membrane threshold potential, it may serve to raise the membrane threshold potential over time, thus having a similar effect to an ion channel that has not been permitted to properly restore ion concentrations. Thus, an ion channel may be recruited as a block without actually causing an initial action potential to propagate. This method may be valuable, for example, in pain management, where the propagation of pain signals is undesired. As described above with respect to stimulation, the larger the number of ion channels in a locality that may be recruited to serve as blocks, the more likely the chance that an action potential propagating along the length of the nerve will be blocked by the recruited ion channels, rather than traveling through neighboring, unblocked channels.

Slowly rising current levels in a modulation signal may affect a nerve in a similar fashion. That is, a current level (and thus voltage potential difference) that increases slowly may serve to raise the membrane threshold potential during the application of the modulation signal, thus causing the nerve to require a higher ultimate current level to achieve modulation, which may result in diminished or absent modulation. Applying a modulation signal such that the current level (or power level) of the signal increases rapidly or greater than a threshold rate may not give the nerve time to react, and thus may ultimately produce more effective modulation at lower current levels. In contrast, using a slow current ramp or a rate lower than a threshold rate may ultimately require higher levels of current to achieve effective neuromodulation. Thus, in order to operate in certain modes, the power transferred to implant unit 110 may be required to increase at a rate that surpasses a power increase threshold rate. To achieve this with a battery alone may require a high-voltage and/or high-current battery. Such a battery may be expensive and/or difficult to design. This need may be obviated by transmitter 1700, which permits the delivery of a rapidly changing current levels and high peak current levels through the use of a power source incapable of delivering the threshold rate of power increase, such as a relatively low voltage/low current battery.

In some embodiments, a threshold rate of power increase in the implant may include an increase in current flow through the implant from substantially zero current to a current level sufficient for effective modulation (e.g., a current between 200 µAmps and 3 mAmps) in less than 20 microseconds, less than 10 microseconds, or less than 5 microseconds. Thus, for example, a threshold rate of power increase may include a current increase between 0.01-0.6 milliamps per microsecond. In some embodiments, a threshold rate of power increase may include a current increase between 0.05-0.2 milliamps per microsecond.

Transmitter 1700 may also offer enhanced efficiency. Transmitter 1700 also may use fewer switches (e.g. transistors) than does a conventional amplifying circuit. Each switch may be a source of energy loss, contributing to an overall less efficient circuit. The presence of a single switch 1730 in transmitter 1700 may increase the efficiency of the circuit as a whole.

The field inducing signal may be generated as a result of conditioning of the secondary signal by circuitry 180. As shown in FIG. 6, circuitry 170 of external unit 120 may be configured to generate an AC primary signal on primary antenna 150 that may cause an AC secondary signal on secondary antenna 152. In certain embodiments, however, it may be advantageous (e.g., in order to generate a unidirectional electric field for modulation of a nerve) to provide a DC field inducing signal at implant electrodes 158a and 158b. To convert the AC secondary signal on secondary antenna 152 to a DC field inducing signal, circuitry 180 in implant unit 110 may include an AC-DC converter. The AC to DC converter may include any suitable converter known to those skilled in the art. For example, in some embodiments the AC-DC converter may include rectification circuit components including, for example, diode 156 and appropriate capacitors and resistors. In alternative embodiments, implant unit 110 may include an AC-AC converter, or no converter, in order to provide an AC field inducing signal at implant electrodes 158a and 158b.

As noted above, the field inducing signal may be configured to generate an electric field between implant electrodes 158a and 158b. In some instances, the magnitude and/or duration of the generated electric field resulting from the field inducing signal may be sufficient to modulate one or more nerves in the vicinity of electrodes 158a and 158b. In such cases, the field inducing signal may be referred to as a modulation signal. In other instances, the magnitude and/or duration of the field inducing signal may generate an electric field that does not result in nerve modulation. In such cases, the field inducing signal may be referred to as a sub-modulation signal.

Various types of field inducing signals may constitute modulation signals. For example, in some embodiments, a modulation signal may include a moderate amplitude and moderate duration, while in other embodiments, a modulation signal may include a higher amplitude and a shorter duration. Various amplitudes and/or durations of field-inducing signals across electrodes 158a, 158b may result in modulation signals, and whether a field-inducing signal rises to the level of a modulation signal can depend on many factors (e.g., distance from a particular nerve to be stimulated; whether the nerve is branched; orientation of the induced electric field with respect to the nerve; type of tissue present between the electrodes and the nerve; etc.).

Whether a field inducing signal constitutes a modulation signal (resulting in an electric field that may cause nerve modulation) or a sub-modulation signal (resulting in an electric field not intended to cause nerve modulation) may ultimately be controlled by processor 144 of external unit 120. For example, in certain situations, processor 144 may determine that nerve modulation is appropriate. Under these conditions, processor 144 may cause signal source 144 and amplifier 146 to generate a modulation control signal on primary antenna 150 (i.e., a signal having a magnitude and/or duration selected such that a resulting secondary signal on secondary antenna 152 will provide a modulation signal at implant electrodes 158a and 158b).

Processor 144 may be configured to limit an amount of energy transferred from external unit 120 to implant unit 110. For example, in some embodiments, implant unit 110 may be associated with a threshold energy limit that may take into account multiple factors associated with the patient and/or the implant. For example, in some cases, certain nerves of a patient should receive no more than a predetermined maximum amount of energy to minimize the risk of damaging the nerves and/or surrounding tissue. Additionally, circuitry 180 of implant unit 110 may include components having a maximum operating voltage or power level that may contribute to a practical threshold energy limit of implant unit 110. Processor 144 may be configured to account for such limitations when setting the magnitude and/or duration of a primary signal to be applied to primary antenna 150.

In addition to determining an upper limit of power that may be delivered to implant unit 110, processor 144 may also determine a lower power threshold based, at least in part, on an efficacy of the delivered power. The lower power threshold may be computed based on a minimum amount of power that enables nerve modulation (e.g., signals having power levels above the lower power threshold may constitute modulation signals while signals having power levels below the lower power threshold may constitute sub-modulation signals).

A lower power threshold may also be measured or provided in alternative ways. For example, appropriate circuitry or sensors in the implant unit 110 may measure a lower power threshold. A lower power threshold may be computed or sensed by an additional external device, and subsequently programmed into processor 144, or programmed into implant unit 110. Alternatively, implant unit 110 may be constructed with circuitry 180 specifically chosen to generate signals at the electrodes of at least the lower power threshold. In still another embodiment, an antenna of external unit 120 may be adjusted to accommodate or produce a signal corresponding to a specific lower power threshold. The lower power threshold may vary from patient to patient, and may take into account multiple factors, such as, for example, modulation characteristics of a particular patient's nerve fibers, a distance between implant unit 110 and external unit 120 after implantation, and the size and configuration of implant unit components (e.g., antenna and implant electrodes), etc.

Processor 144 may also be configured to cause application of sub-modulation control signals to primary antenna 150. Such sub-modulation control signals may include an amplitude and/or duration that result in a sub-modulation signal at electrodes 158a, 158b. While such sub-modulation control signals may not result in nerve modulation, such sub-modulation control signals may enable feedback-based control of the nerve modulation system. That is, in some embodiments, processor 144 may be configured to cause application of a sub-modulation control signal to primary antenna 150. This signal may induce a secondary signal on secondary antenna 152, which, in turn, induces a primary coupled signal component on primary antenna 150.

To analyze the primary coupled signal component induced on primary antenna 150, external unit 120 may include a feedback circuit 148 (e.g., a signal analyzer or detector, etc.), which may be placed in direct or indirect communication with primary antenna 150 and processor 144. Sub-modulation control signals may be applied to primary antenna 150 at any desired periodicity. In some embodiments, the sub-modulation control signals may be applied to primary antenna 150 at a rate of one every five seconds (or longer). In other embodiments, the sub-modulation control signals may be applied more frequently (e.g., once every two seconds, once per second, once per millisecond, once per nanosecond, or multiple times per second). Further, it should be noted that feedback may also be received upon application of modulation control signals to primary antenna 150 (i.e., those that result in nerve modulation), as such modulation control signals may also result in generation of a primary coupled signal component on primary antenna 150.

The primary coupled signal component may be fed to processor 144 by feedback circuit 148 and may be used as a basis for determining a degree of coupling between primary antenna 150 and secondary antenna 152. The degree of coupling may enable determination of the efficacy of the energy transfer between two antennas. Processor 144 may also use the determined degree of coupling in regulating delivery of power to implant unit 110.

Processor 144 may be configured with any suitable logic for determining how to regulate power transfer to implant unit 110 based on the determined degree of coupling. For example, where the primary coupled signal component indicates that a degree of coupling has changed from a baseline coupling level, processor 144 may determine that secondary antenna 152 has moved with respect to primary antenna 150 (either in coaxial offset, lateral offset, or angular offset, or any combination). Such movement, for example, may be associated with a movement of the implant unit 110, and the tissue that it is associated with based on its implant location. Thus, in such situations, processor 144 may determine that modulation of a nerve in the patient's body is appropriate. More particularly, in response to an indication of a change in coupling, processor 144, in some embodiments, may cause application of a modulation control signal to primary antenna 150 in order to generate a modulation signal at implant electrodes 158a, 158b, e.g., to cause modulation of a nerve of the patient.

In an embodiment for the treatment of OSA, movement of an implant unit 110 may be associated with movement of the tongue, which may indicate the onset of a sleep apnea event or a sleep apnea precursor. The onset of a sleep apnea event of sleep apnea precursor may require the stimulation of the genioglossus muscle of the patient to relieve or avert the event. Such stimulation may result in contraction of the muscle and movement of the patient's tongue away from the patient's airway.

In embodiments for the treatment and management of head pain, including migraines, processor 144 may be configured to generate a modulation control signal based on a signal from a user, for example, or a detected level of neural activity in a sensory neuron (e.g. the greater occipital nerve or trigeminal nerve) associated with head pain. A modulation control signal generated by the processor and applied to the primary antenna 150 may generate a modulation signal at implant electrodes 158a, 158b, e.g., to cause inhibition or blocking of a sensory nerve of the patient. Such inhibition or blocking may decrease or eliminate the sensation of pain for the patient.

In embodiments for the treatment of hypertension, processor 144 may be configured to generate a modulation control signal based on, for example, pre-programmed instructions and/or signals from an implant indicative of blood pressure. A modulation control signal generated by the processor and applied to the primary antenna 150 may generate a modulation signal at implant electrodes 158a, 158b, e.g., to cause either inhibition or stimulation of nerve of a patient, depending on the requirements. For example, a neuromodulator placed in a carotid artery or jugular artery (i.e. in the vicinity of a carotid baroreceptor), may receive a modulation control signal tailored to induce a stimulation signal at the electrodes, thereby causing the glossopharyngeal nerve associated with the carotid baroreceptors to fire at an increased rate in order to signal the brain to lower blood pressure. Similar modulation of the glossopharyngeal nerve may be achieved with a neuromodulator implanted in a subcutaneous location in a patient's neck or behind a patient's ear. A neuromodulator place in a renal artery may receive a modulation control signal tailored to cause an inhibiting or blocking signal at the electrodes, thereby inhibiting a signal to raise blood pressure carried from the renal nerves to the kidneys.

Modulation control signals may include stimulation control signals, and sub-modulation control signals may include sub-stimulation control signals. Stimulation control signals may have any amplitude, pulse duration, or frequency combination that results in a stimulation signal at electrodes 158a, 158b. In some embodiments (e.g., at a frequency of between about 6.5-13.6 MHz), stimulation control signals may include a pulse duration of greater than about 50 microseconds and/or an amplitude of approximately 0.5 amps, or between 0.1 amps and 1 amp, or between 0.05 amps and 3 amps. Sub-stimulation control signals may have a pulse duration less than about 500, or less than about 200 nanoseconds and/or an amplitude less than about 1 amp, 0.5 amps, 0.1 amps, 0.05 amps, or 0.01 amps. Of course, these values are meant to provide a general reference only, as various combinations of values higher than or lower than the exemplary guidelines provided may or may not result in nerve stimulation.

In some embodiments, stimulation control signals may include a pulse train, wherein each pulse includes a plurality of sub-pulses. An alternating current signal (e.g., at a frequency of between about 6.5-13.6 MHz) may be used to generate the pulse train, as follows. A sub-pulse may have a duration of between 50-250 microseconds, or a duration of between 1 microsecond and 2 milliseconds, during which an alternating current signal is turned on. For example, a 200 microsecond sub-pulse of a 10 MHz alternating current signal will include approximately 2000 periods. Each pulse may, in turn, have a duration of between 100 and 500 milliseconds, during which sub-pulses occur at a frequency of between 25 and 100 Hz. For example, a 200 millisecond pulse of 50 Hz sub-pulses will include approximately 10 sub-pulses. Finally, in a pulse train, each pulse may be separated from the next by a duration of between 0.2 and 2 seconds. For example, in a pulse train of 200 millisecond pulses, each separated by 1.3 seconds from the next, a new pulse will occur every 1.5 seconds. A pulse train of this embodiment may be utilized, for example, to provide ongoing stimulation during a treatment session. In the context of OSA, a treatment session may be a period of time during which a subject is asleep and in need of treatment to prevent OSA. Such a treatment session may last anywhere from about three to ten hours. In the context of other conditions to which neural modulators of the present disclosure are applied, a treatment session may be of varying length according to the duration of the treated condition.

As discussed above, a pulse train may be generated by a pulsed mode self-resonant transmitter as described herein. For example, each sub-pulse may be generated by assembling multiple current loading periods and free oscillation periods. A period between sub-pulses may include an energy accumulation period, after which another sub-pulse comprising multiple current loading periods and free oscillation periods may be generated. In this manner, a pulse train having any or all of the parameters as described above may be generated utilizing a pulsed mode self-resonant transmitter.

Processor 144 may be configured to determine a degree of coupling between primary antenna 150 and secondary antenna 152 by monitoring one or more aspects of the primary coupled signal component received through feedback circuit 148. In some embodiments, processor 144 may determine a degree of coupling between primary antenna 150 and secondary antenna 152 by monitoring a voltage level associated with the primary coupled signal component, a current level, or any other attribute that may depend on the degree of coupling between primary antenna 150 and secondary antenna 152. For example, in response to periodic sub-modulation signals applied to primary antenna 150, processor 144 may determine a baseline voltage level or current level associated with the primary coupled signal component. This baseline voltage level, for example, may be associated with a range of movement of the patient's tongue when a sleep apnea event or its precursor is not occurring, e.g. during normal breathing. As the patient's tongue moves toward a position associated with a sleep apnea event or its precursor, the coaxial, lateral, or angular offset between primary antenna 150 and secondary antenna 152 may change. As a result, the degree of coupling between primary antenna 150 and secondary antenna 152 may change, and the voltage level or current level of the primary coupled signal component on primary antenna 150 may also change. Processor 144 may be configured to recognize a sleep apnea event or its precursor when a voltage level, current level, or other electrical characteristic associated with the primary coupled signal component changes by a predetermined amount or reaches a predetermined absolute value.

Figure 7:
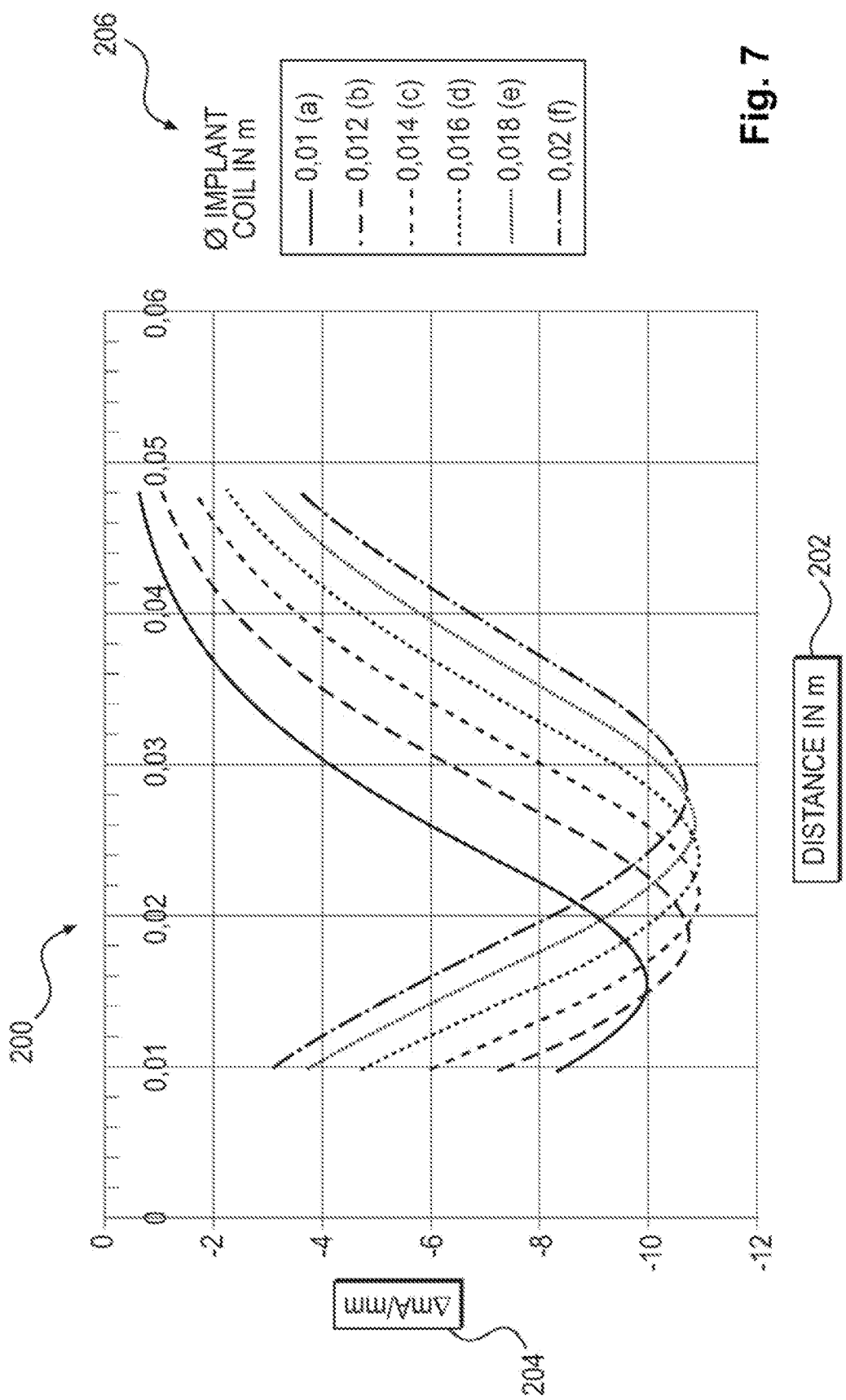
FIG. 7 illustrates a graph of quantities that may be used in determining energy delivery as a function coupling, according to exemplary disclosed embodiments.

FIG. 7 provides a graph that illustrates this principle in more detail. For a two-coil system where one coil receives a radio frequency (RF) drive signal, graph 200 plots a rate of change in induced current in the receiving coil as a function of coaxial distance between the coils. For various coil diameters and initial displacements, graph 200 illustrates the sensitivity of the induced current to further displacement between the coils, moving them either closer together or further apart. It also indicates that, overall, the induced current in the secondary coil will decrease as the secondary coil is moved away from the primary, drive coil, i.e. the rate of change of induced current, in mA/mm, is consistently negative. The sensitivity of the induced current to further displacement between the coils varies with distance. For example, at a separation distance of 10 mm, the rate of change in current as a function of additional displacement in a 14 mm coil is approximately −6 mA/mm. If the displacement of the coils is approximately 22 mm, the rate of change in the induced current in response to additional displacement is approximately −11 mA/mm, which corresponds to a local maximum in the rate of change of the induced current. Increasing the separation distance beyond 22 mm continues to result in a decline in the induced current in the secondary coil, but the rate of change decreases. For example, at a separation distance of about 30 mm, the 14 mm coil experiences a rate of change in the induced current in response to additional displacement of about −8 mA/mm. With this type of information, processor 144 may be able to determine a particular degree of coupling between primary antenna 150 and secondary antenna 152, at any given time, by observing the magnitude and/or rate of change in the magnitude of the current associated with the primary coupled signal component on primary antenna 150.

Processor 144 may be configured to determine a degree of coupling between primary antenna 150 and secondary antenna 152 by monitoring other aspects of the primary coupled signal component. For example, in some embodiments, the non-linear behavior of circuitry 180 in implant unit 110 may be monitored to determine a degree of coupling. For example, the presence, absence, magnitude, reduction and/or onset of harmonic components in the primary coupled signal component on primary antenna 150 may reflect the behavior of circuitry 180 in response to various control signals (either sub-modulation or modulation control signals) and, therefore, may be used to determine a degree of coupling between primary antenna 150 and secondary antenna 152.

As shown in FIG. 6, circuitry 180 in implant unit 110 may constitute a non-linear circuit due, for example, to the presence of non-linear circuit components, such as diode 156. Such non-linear circuit components may induce non-linear voltage responses under certain operation conditions. Non-linear operation conditions may be induced when the voltage potential across diode 156 exceeds the activation threshold for diode 156. Thus, when implant circuitry 180 is excited at a particular frequency, this circuit may oscillate at multiple frequencies. Spectrum analysis of the secondary signal on secondary antenna 152, therefore, may reveal one or more oscillations, called harmonics, that appear at certain multiples of the excitation frequency. Through coupling of primary antenna 150 and secondary antenna 152, any harmonics produced by implant circuitry 180 and appearing on secondary antenna 152 may also appear in the primary coupled signal component present on primary antenna 150.

In certain embodiments, circuitry 180 may include additional circuit components that alter the characteristics of the harmonics generated in circuitry 180 above a certain transition point. Monitoring how these non-linear harmonics behave above and below the transition point may enable a determination of a degree of coupling between primary antenna 150 and secondary antenna 152. For example, as shown in FIG. 6, circuitry 180 may include a harmonics modifier circuit 154, which may include any electrical components that non-linearly alter the harmonics generated in circuitry 180. In some embodiments, harmonics modifier circuit 154 may include a pair of Zener diodes. Below a certain voltage level, these Zener diodes remain forward biased such that no current will flow through either diode. Above the breakdown voltage of the Zener diodes, however, these devices become conductive in the reversed biased direction and will allow current to flow through harmonics modifier circuit 154. Once the Zener diodes become conductive, they begin to affect the oscillatory behavior of circuitry 180, and, as a result, certain harmonic oscillation frequencies may be affected (e.g., reduced in magnitude).

Figure 8:
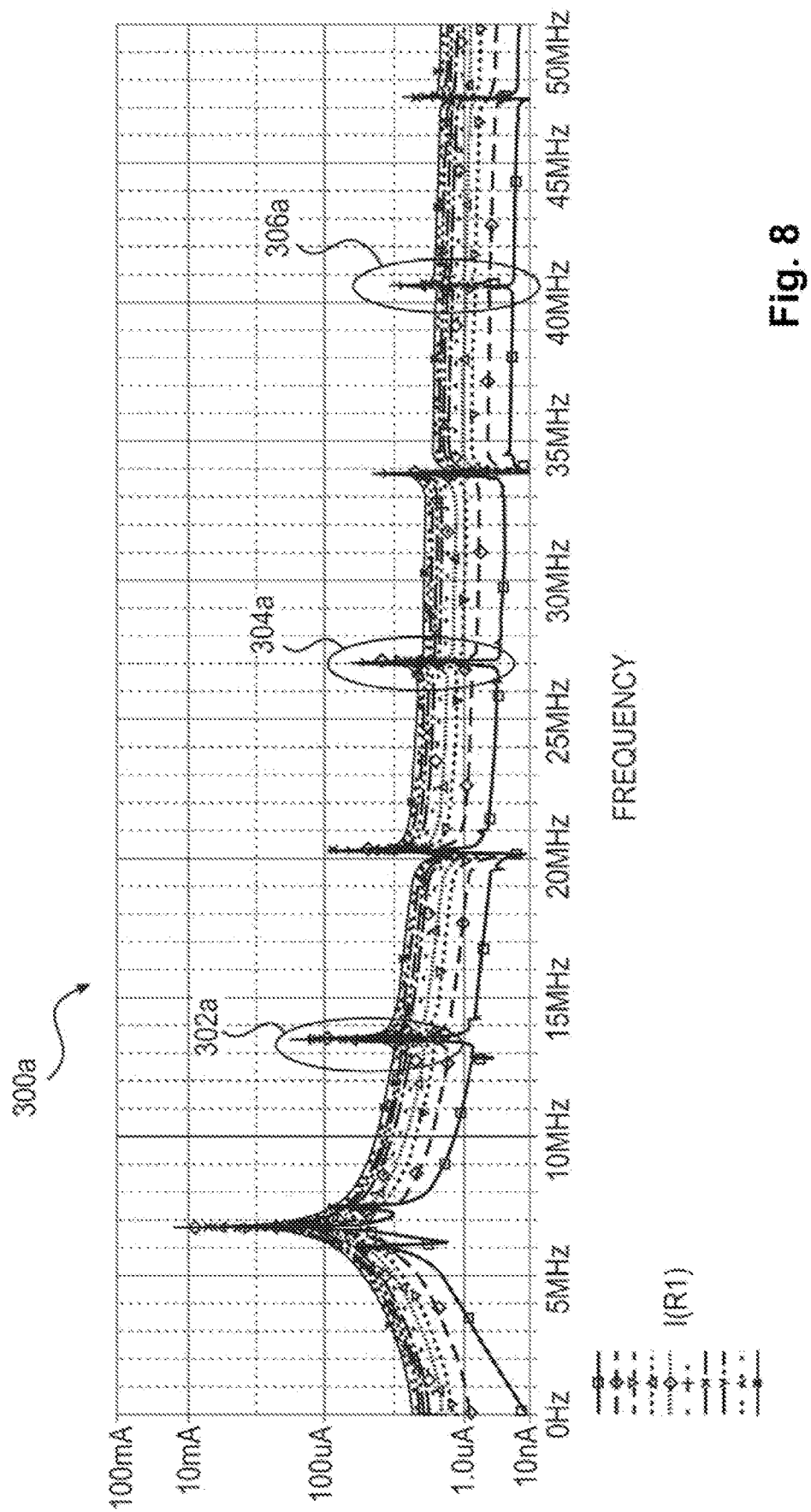
FIG. 8 depicts a graph illustrating non-linear harmonics.
Figure 9:
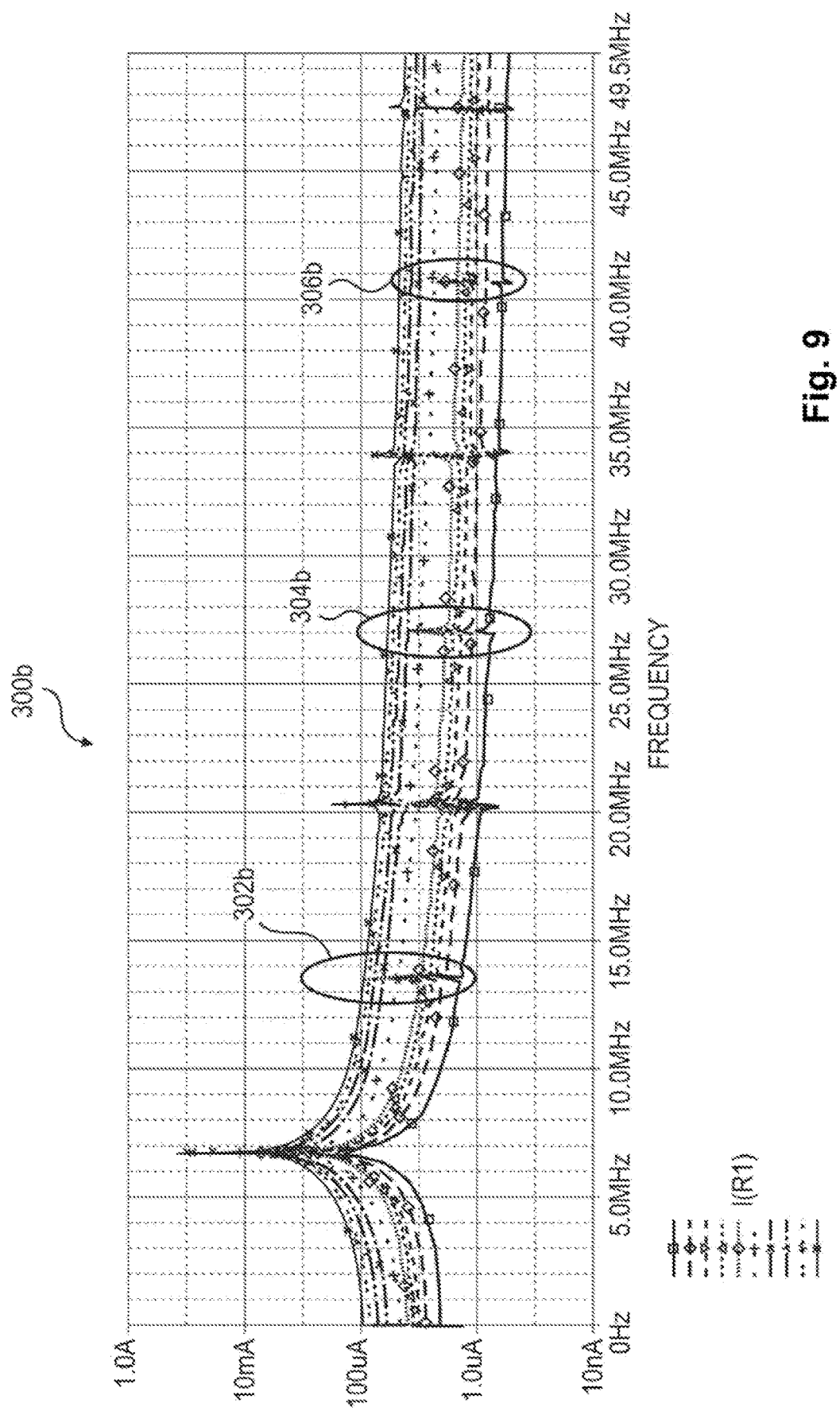
FIG. 9 depicts a graph of quantities that may be used in determining energy delivery as a function coupling, according to exemplary disclosed embodiments.

FIGS. 8 and 9 illustrate this effect. For example, FIG. 8 illustrates a graph 300*a* that shows the oscillatory behavior of circuitry 180 at several amplitudes ranging from about 10 nanoamps to about 20 microamps. As shown, the primary excitation frequency occurs at about 6.7 MHz and harmonics appear both at even and odd multiples of the primary excitation frequency. For example, even multiples appear at twice the excitation frequency (peak 302a), four times the excitation frequency (peak 304a) and six times the excitation frequency (peak 306a). As the amplitude of the excitation signal rises between 10 nanoamps and 40 microamps, the amplitude of peaks 302a, 304a, and 306a all increase.

FIG. 9 illustrates the effect on the even harmonic response of circuitry 180 caused by harmonics modifier circuit 154. FIG. 9 illustrates a graph 300b that shows the oscillatory behavior of circuitry 180 at several amplitudes ranging from about 30 microamps to about 100 microamps. As in FIG. 8, FIG. 9 shows a primary excitation frequency at about 6.7 MHz and second, fourth, and sixth order harmonics (peaks 302b, 304b, and 306b, respectively) appearing at even multiples of the excitation frequency. As the amplitude of the excitation signal rises, however, between about 30 microamps to about 100 microamps, the amplitudes of peaks 302b, 304b, and 306b do not continuously increase. Rather, the amplitude of the second order harmonics decreases rapidly above a certain transition level (e.g., about 80 microamps in FIG. 8). This transition level corresponds to the level at which the Zener diodes become conductive in the reverse biased direction and begin to affect the oscillatory behavior of circuitry 180.

Monitoring the level at which this transition occurs may enable a determination of a degree of coupling between primary antenna 150 and secondary antenna 152. For example, in some embodiments, a patient may attach external unit 120 over an area of the skin under which implant unit 110 resides. Processor 144 can proceed to cause a series of sub-modulation control signals to be applied to primary antenna 150, which in turn cause secondary signals on secondary antenna 152. These sub-modulation control signals may progress over a sweep or scan of various signal amplitude levels. By monitoring the resulting primary coupled signal component on primary antenna 150 (generated through coupling with the secondary signal on secondary antenna 152), processor 144 can determine the amplitude of primary signal (whether a sub-modulation control signal or other signal) that results in a secondary signal of sufficient magnitude to activate harmonics modifier circuit 154. That is, processor 144 can monitor the amplitude of the second, fourth, or sixth order harmonics and determine the amplitude of the primary signal at which the amplitude of any of the even harmonics drops. FIGS. 8 and 9 illustrate the principles of detecting coupling through the measurement of non-linear harmonics. These Figures illustrate data based around a 6.7 MHz excitation frequency. These principles, however, are not limited to the 6.7 MHz excitation frequency illustrated, and may be used with a primary signal of any suitable frequency.

In some embodiments, the determined amplitude of the primary signal corresponding to the transition level of the Zener diodes (which may be referred to as a primary signal transition amplitude) may establish a baseline range when the patient attaches external unit 120 to the skin. Presumably, while the patient is awake, the tongue is not blocking the patient's airway and moves with the patients breathing in a natural range, where coupling between primary antenna 150 and secondary antenna 152 may be within a baseline range. A baseline coupling range may encompass a maximum coupling between primary antenna 150 and secondary antenna 152. A baseline coupling range may also encompass a range that does not include a maximum coupling level between primary antenna 150 and secondary antenna 152. Thus, the initially determined primary signal transition amplitude may be fairly representative of a non-sleep apnea condition and may be used by processor 144 as a baseline in determining a degree of coupling between primary antenna 150 and secondary antenna 152. Optionally, processor 144 may also be configured to monitor the primary signal transition amplitude over a series of scans and select the minimum value as a baseline, as the minimum value may correspond to a condition of maximum coupling between primary antenna 150 and secondary antenna 152 during normal breathing conditions.

As the patient wears external unit 120, processor 144 may periodically scan over a range of primary signal amplitudes to determine a current value of the primary signal transition amplitude. In some embodiments, the range of amplitudes that processor 144 selects for the scan may be based on (e.g., near) the level of the baseline primary signal transition amplitude. If a periodic scan results in determination of a primary signal transition amplitude different from the baseline primary signal transition amplitude, processor 144 may determine that there has been a change from the baseline initial conditions. For example, in some embodiments, an increase in the primary signal transition amplitude over the baseline value may indicate that there has been a reduction in the degree of coupling between primary antenna 150 and secondary antenna 152 (e.g., because the implant has moved or an internal state of the implant has changed).

In addition to determining whether a change in the degree of coupling has occurred, processor 144 may also be configured to determine a specific degree of coupling based on an observed primary signal transition amplitude. For example, in some embodiments, processor 144 may have access to a lookup table or a memory storing data that correlates various primary signal transition amplitudes with distances (or any other quantity indicative of a degree of coupling) between primary antenna 150 and secondary antenna 152. In other embodiments, processor 144 may be configured to calculate a degree of coupling based on performance characteristics of known circuit components.

By periodically determining a degree of coupling value, processor 144 may be configured to determine, in situ, appropriate parameter values for the modulation control signal that will ultimately result in nerve modulation. For example, by determining the degree of coupling between primary antenna 150 and secondary antenna 152, processor 144 may be configured to select characteristics of the modulation control signal (e.g., amplitude, pulse duration, frequency, etc.) that may provide a modulation signal at electrodes 158a, 158b in proportion to or otherwise related to the determined degree of coupling. In some embodiments, processor 144 may access a lookup table or other data stored in a memory correlating modulation control signal parameter values with degree of coupling. In this way, processor 144 may adjust the applied modulation control signal in response to an observed degree of coupling.

Additionally or alternatively, processor 144 may be configured to determine the degree of coupling between primary antenna 150 and secondary antenna 152 during modulation. The tongue, or other structure on or near which the implant is located, and thus implant unit 110, may move as a result of modulation. Thus, the degree of coupling may change during modulation. Processor 144 may be configured to determine the degree of coupling as it changes during modulation, in order to dynamically adjust characteristics of the modulation control signal according to the changing degree of coupling. This adjustment may permit processor 144 to cause implant unit 110 to provide an appropriate modulation signal at electrodes 158a, 158b throughout a modulation event. For example, processor 144 may alter the primary signal in accordance with the changing degree of coupling in order to maintain a constant modulation signal, or to cause the modulation signal to be reduced in a controlled manner according to patient needs.

More particularly, the response of processor 144 may be correlated to the determined degree of coupling. In situations where processor 144 determines that the degree of coupling between primary antenna 150 and secondary antenna has fallen only slightly below a predetermined coupling threshold (e.g., during snoring or during a small vibration of the tongue or other sleep apnea event precursor), processor 144 may determine that only a small response is necessary. Thus, processor 144 may select modulation control signal parameters that will result in a relatively small response (e.g., a short stimulation of a nerve, small muscle contraction, etc.). Where, however, processor 144 determines that the degree of coupling has fallen substantially below the predetermined coupling threshold (e.g., where the tongue has moved enough to cause a sleep apnea event), processor 144 may determine that a larger response is required. As a result, processor 144 may select modulation control signal parameters that will result in a larger response. In some embodiments, only enough power may be transmitted to implant unit 110 to cause the desired level of response. In other words, processor 144 may be configured to cause a metered response based on the determined degree of coupling between primary antenna 150 and secondary antenna 152. As the determined degree of coupling decreases, processor 144 may cause transfer of power in increasing amounts. Such an approach may preserve battery life in the external unit 120, may protect circuitry 170 and circuitry 180, may increase effectiveness in addressing the type of detected condition (e.g., sleep apnea, snoring, tongue movement, etc.), and may be more comfortable for the patient.

In some embodiments, processor 144 may employ an iterative process in order to select modulation control signal parameters that result in a desired response level. For example, upon determining that a modulation control signal should be generated, processor 144 may cause generation of an initial modulation control signal based on a set of predetermined parameter values. If feedback from feedback circuit 148 indicates that a nerve has been modulated (e.g., if an increase in a degree of coupling is observed), then processor 144 may return to a monitoring mode by issuing sub-modulation control signals. If, on the other hand, the feedback suggests that the intended nerve modulation did not occur as a result of the intended modulation control signal or that modulation of the nerve occurred but only partially provided the desired result (e.g., movement of the tongue only partially away from the airway), processor 144 may change one or more parameter values associated with the modulation control signal (e.g., the amplitude, pulse duration, etc.).

Where no nerve modulation occurred, processor 144 may increase one or more parameters of the modulation control signal periodically until the feedback indicates that nerve modulation has occurred. Where nerve modulation occurred, but did not produce the desired result, processor 144 may re-evaluate the degree of coupling between primary antenna 150 and secondary antenna 152 and select new parameters for the modulation control signal targeted toward achieving a desired result. For example, where stimulation of a nerve causes the tongue to move only partially away from the patient's airway, additional stimulation may be desired. Because the tongue has moved away from the airway, however, implant unit 110 may be closer to external unit 120 and, therefore, the degree of coupling may have increased. As a result, to move the tongue a remaining distance to a desired location may require transfer to implant unit 110 of a smaller amount of power than what was supplied prior to the last stimulation-induced movement of the tongue. Thus, based on a newly determined degree of coupling, processor 144 can select new parameters for the stimulation control signal aimed at moving the tongue the remaining distance to the desired location.

In one mode of operation, processor 144 may be configured to sweep over a range of parameter values until nerve modulation is achieved. For example, in circumstances where an applied sub-modulation control signal results in feedback indicating that nerve modulation is appropriate, processor 144 may use the last applied sub-modulation control signal as a starting point for generation of the modulation control signal. The amplitude and/or pulse duration (or other parameters) associated with the signal applied to primary antenna 150 may be iteratively increased by predetermined amounts and at a predetermined rate until the feedback indicates that nerve modulation has occurred.

Processor 144 may be configured to determine or derive various physiologic data based on the determined degree of coupling between primary antenna 150 and secondary antenna 152. For example, in some embodiments the degree of coupling may indicate a distance between external unit 120 and implant unit 110, which processor 144 may use to determine a position of external unit 120 or a relative position of a patient's tongue. Monitoring the degree of coupling can also provide such physiologic data as whether a patient's tongue is moving or vibrating (e.g., whether the patient is snoring), by how much the tongue is moving or vibrating, the direction of motion of the tongue, the rate of motion of the tongue, etc.

In response to any of these determined physiologic data, processor 144 may regulate delivery of power to implant unit 110 based on the determined physiologic data. For example, processor 144 may select parameters for a particular modulation control signal or series of modulation control signals for addressing a specific condition relating to the determined physiologic data. If the physiologic data indicates that the tongue is vibrating, for example, processor 144 may determine that a sleep apnea event is likely to occur and may issue a response by delivering power to implant unit 110 in an amount selected to address the particular situation. If the tongue is in a position blocking the patient's airway (or partially blocking a patient's airway), but the physiologic data indicates that the tongue is moving away from the airway, processor 144 may opt to not deliver power and wait to determine if the tongue clears on its own. Alternatively, processor 144 may deliver a small amount of power to implant unit 110 (e.g., especially where a determined rate of movement indicates that the tongue is moving slowly away from the patient's airway) to encourage the tongue to continue moving away from the patient's airway or to speed its progression away from the airway. The scenarios described are exemplary only. Processor 144 may be configured with software and/or logic enabling it to address a variety of different physiologic scenarios with particularity. In each case, processor 144 may be configured to use the physiologic data to determine an amount of power to be delivered to implant unit 110 in order to modulate nerves associated with the tongue with the appropriate amount of energy.

The disclosed embodiments may be used in conjunction with a method for regulating delivery of power to an implant unit. The method may include determining a degree of coupling between primary antenna 150 associated with external unit 120 and secondary antenna 152 associated with implant unit 110, implanted in the body of a patient. Determining the degree of coupling may be accomplished by processor 144 located external to implant unit 110 and that may be associated with external unit 120. Processor 144 may be configured to regulate delivery of power from the external unit to the implant unit based on the determined degree of coupling.

As previously discussed, the degree of coupling determination may enable the processor to further determine a location of the implant unit. The motion of the implant unit may correspond to motion of the body part where the implant unit may be attached. This may be considered physiologic data received by the processor. The processor may, accordingly, be configured to regulate delivery of power from the power source to the implant unit based on the physiologic data. In alternative embodiments, the degree of coupling determination may enable the processor to determine information pertaining to a condition of the implant unit. Such a condition may include location as well as information pertaining to an internal state of the implant unit. The processor may, according to the condition of the implant unit, be configured to regulate delivery of power from the power source to the implant unit based on the condition data.

In some embodiments, implant unit 110 may include a processor located on the implant. A processor located on implant unit 110 may perform all or some of the processes described with respect to the at least one processor associated with an external unit. For example, a processor associated with implant unit 110 may be configured to receive a control signal prompting the implant controller to turn on and cause a modulation signal to be applied to the implant electrodes for modulating a nerve. Such a processor may also be configured to monitor various sensors associated with the implant unit and to transmit this information back to and external unit. Power for the processor unit may be supplied by an onboard power source or received via transmissions from an external unit.

In other embodiments, implant unit 110 may be self-sufficient, including its own power source and a processor configured to operate the implant unit 110 with no external interaction. For example, with a suitable power source, the processor of implant unit 110 could be configured to monitor conditions in the body of a subject (via one or more sensors or other means), determining when those conditions warrant modulation of a nerve, and generate a signal to the electrodes to modulate a nerve. The power source could be regenerative based on movement or biological function; or the power sources could be periodically rechargeable from an external location, such as, for example, through induction.

Figure 14:
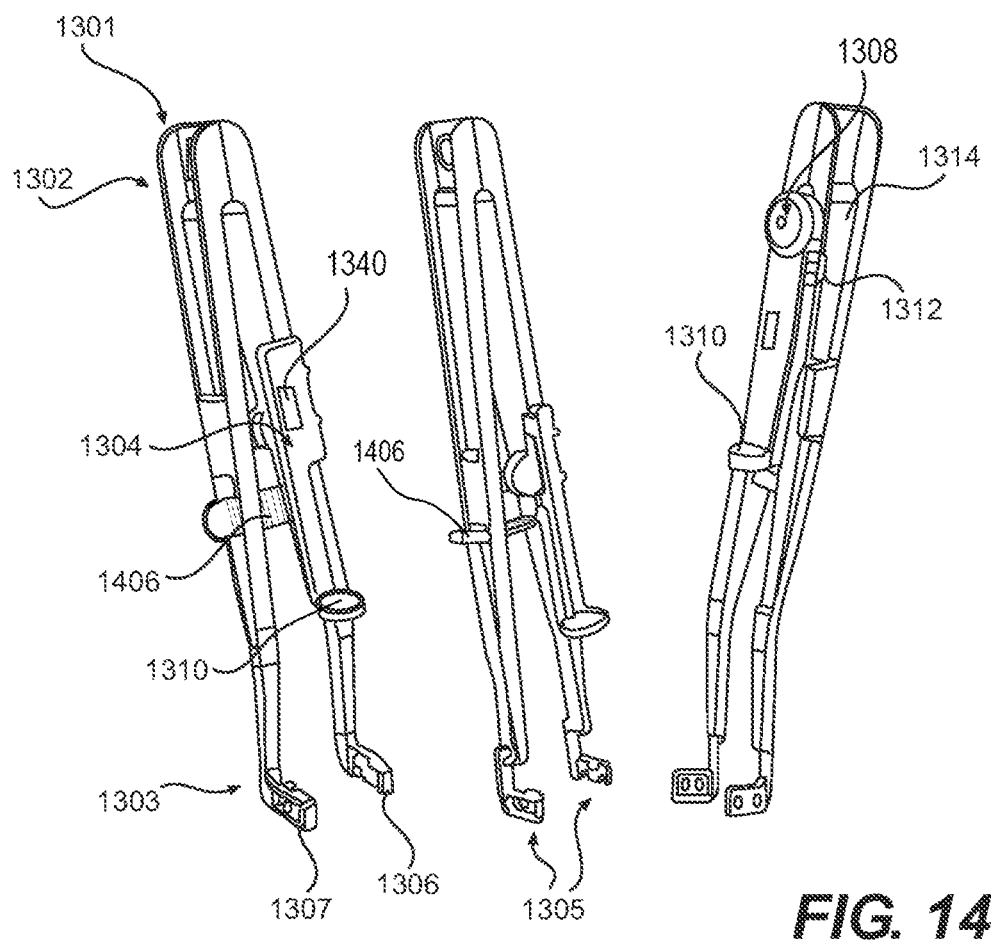
FIG. 14 illustrates various aspects of a delivery tool.
Figure 15:
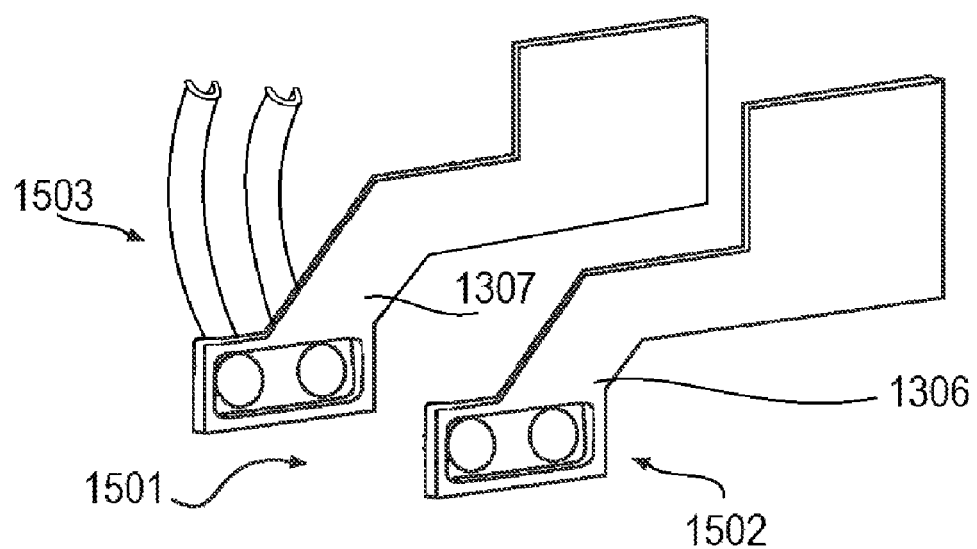
FIG. 15 depicts features of a delivery tool implant holder portion.

Some embodiments of the present disclosure may include methods, devices, and tools for the implantation of implant unit 110. FIGS. 13-15 illustrate an exemplary embodiment of a delivery tool for use in the implantation of implant unit 110 and various features thereof. The features illustrated in FIGS. 13-15 may be combined in any suitable fashion in various embodiments consistent with this disclosure. A delivery tool 1301 may be used during an implantation procedure to properly position implant unit 110, to test implant unit 110, and/or to assist a surgeon in securing implant unit 110 to an appropriate internal body structure.

FIGS. 13a-13c illustrate various aspects of delivery tool 1301. In some embodiments, delivery tool 1301 may include an implant retainer configured to selectively hold implant unit 110 and maintain implant unit 110 in a fixation location relative to target tissue in a subject's body during an implantation procedure. Delivery tool 1301 may include a body 1302, an implant holder 1303 adapted to releasably hold an implant unit, an implant activator 1304, and a power source 1308 associated with the implant activator 1304. Body 1302 may include a handle formed so as to receive a thumb and at least one forefinger of a user. As shown in FIG. 13a, body 1302 may include a first face 1315 and a second face 1316. Holder 1303 may include any structure adapted to hold and release an implant unit. In some embodiments, holder 1303 may be adapted to hold implant unit 110. Holder 1303 may include various components to releasably hold implant unit 110, such as a vacuum element (not shown), or latching element (not shown), etc.

Holder 1303 may also include a pair of jaws 1305 disposed in an opposing relationship as shown in FIG. 13c. For example, jaws 1305 may include a first jaw 1306 pivotally attached to a second jaw 1307. The spacing of the opposing jaws 1305 may be adjustable, for example through a tweezer-type movement of the delivery tool 1301. The tweezer-type movement of the delivery tool 1301 may be controlled by a ratchet 1406, as shown in FIG. 14, configured to maintain spacing between jaws 1305 when employed. Thus, a user may position implant unit 110 inside jaws 1305, press the jaws 1305 together until implant unit 110 is firmly held in a flexed position, and employ ratchet 1406 to maintain the spacing of jaws 1305. A user, such as a surgeon, may then release pressure on the delivery tool 1301 while the position of the implant unit 110 is maintained with ratchet 1406. Maintaining a position of the implant unit may be useful prior to an implantation procedure, as a surgeon prepares for the implantation. It may also be useful during an implantation procedure, as a surgeon may hold implant unit 110 in place with respect to an implantation location as implantation steps are performed. Ratchet 1406 may be released, for example when implant unit 110 is within a desired position within the patient, causing jaws 1305 to open. Implant unit 110 may then be released from delivery tool 1301 and implanted within the patient. As shown in FIG. 14, ratchet 1406 may include various configuration as is known in the art.

The flexed position of the implant unit 110, between jaws 1305, may be chosen such that the implant unit 110 may substantially conform to a contour of tissue in a patient's body when implanted. For example, holder 1303 may hold implant unit 110 in a bent, curved, compressed, or stretched configuration. As shown in FIG. 13c, holder 1303 may hold implant unit 110 such that first extension 162a of implant unit 110 is maintained substantially against second jaw 1307 and second extension 162b of implant unit 110 is maintained substantially against first jaw 1306.

Holder 1303 may also include at least one suture guide member 1501, configured to receive surgical sutures. As shown in FIG. 15, a suture guide member 1501 may include a first suture guide portion 1502 and a second suture guide portion 1503 adapted for the insertion and/or guiding of a surgical needle during an implantation process. First suture guide portion 1502 may be disposed on a first side of holder 1303 and second suture guide portion 1503 may be disposed on a second side of holder 1303, wherein the second side is opposite the first side. Therefore, first and second suture guide portions 1502, 1503 may be associated with holder 1303.

First suture guide portion 1502 may include one or more apertures in jaws 1305, and second suture guide portion 1503 may include a curved channel. In one embodiment, first suture guide portion 1502 may include an aperture in first jaw 1306. The channel of second suture guide portion 1503 may include an arcuate shape extending from second jaw 1307. The channel may have a radius of curvature corresponding to a surgical needle. For example, suture guide member 1501 may be shaped so as to receive any type of surgical suture needle, such as ¼ circle, ⅜ circle, ⅝ circle, ½ circle or ½ curved. Suture guide member 1501 may be configured to correspond to suture holes 160 and/or surgical mesh 1050 of implant unit 110, and may thus facilitate an implantation procedure.

During an implantation procedure, implant unit 110 may be positioned to conform to a tissue structure of a subject, and a surgeon may use suture guide member 1501 to appropriately locate and guide a suture needle in order to suture implant unit 110 in place. Suture guide member 1501 may be configured to set a predetermined angle between suture guide member 1501 and a patient's tissue, and therefore may assist the surgeon by permitting the insertion of a suture needle at the predetermined angle. For example, suture guide member 1501 may set an angle of about 90 degrees between suture guide member 1501 and the patient's tissue. In other embodiments, suture guide member 1501 may set an angle of about 60, about 45, or about 30 degrees.

Returning now to FIGS. 13*a-c*, as described above, delivery tool 1301 may include an implant activator 1304. Implant activator 1304 may be configured to be employed and activated during an implantation procedure. Implant activator 1304 may include an activator antenna 1310, at least one processor 1340 in electrical communication with activator antenna 1310, and a power source 1308. Implant activator 1304 may be configured to interact wirelessly with implant unit 110 to cause modulation of at least one nerve in the body of a patient prior to final fixation of implant unit 110 to tissue. In some embodiments, implant activator 1304 may be configured to interact with implant unit 110 through signals transmitted by activator antenna 1310.

Implant activator 1304 may be slideably disposed on delivery tool 1301 such that implant activator 1304 may slide within a track 1314 formed between first and second faces 1315, 1316. Therefore, implant activator 1304 may slide toward and away from an implant 110, disposed between jaws 1305, within track 1314. For example, implant activator 1304 may slide from a first position (FIG. 13*a*) to a second position (FIG. 13*b*) a predetermined distance along body 1302. It is further contemplated that one or more securing means 1317 may secure and retain implant activator 1340 within track 1314 when sliding up and down along body 1302. Additionally or alternatively, a protrusion 1312 on implant activator 1304 may slide within the groove formed by track 1314. Securing means 1317 and/or protrusion 1312 may selectively lock implant activator 1304 at a predetermined location along body 1302.

A slideable engagement portion 1321 may activate implant activator 1304 causing implant activator 1304 to slide from the first position toward the second position or from the second position toward the first position. For example, slideable engagement portion 1321 may include a trigger or button configured to be engaged by a user. In one embodiment, a user may depress slideable engagement portion 1321 to activate implant activator 1304. Alternatively, implant activator 1304 may be moved from the first position to the second position, and from the second position to the first position, through a pivotal movement facilitated by a pivotal attachment (not shown). It is further contemplated that a user may slide implant activator 1304 into the desired position to move implant activator 1304 along track 1314. A shown in FIG. 14, implant activator 1304 may include various shapes and depressions configured to conform to a user's fingers or palm. Such may enable easy sliding of implant activator 1304. Other means of shifting implant activator 1304 may also be employed without departing from the disclosed embodiments.

Processor 1340 may be configured to determine and regulate a degree of coupling between activator antenna 1310 and secondary antenna 152. As shown in FIG. 13*a*, processor 1340 may be located within or on a surface of body 1302 of delivery tool 1301. In alternative embodiments, processor 1340 may be configured for wired or wireless communication from a location external to delivery tool 1301. Processor 1340 may include, for example, one or more integrated circuits, microchips, microcontrollers, and microprocessors, which may be all or part of a central processing unit (CPU), a digital signal processor (DSP), a field programmable gate array (FPGA), or any other circuit known to those skilled in the art that may be suitable for executing instructions or performing logic operations.

Power source 1308 may be removably or permanently coupled to body 1302 of delivery tool 1301. For example, as shown in FIG. 13*a*, power source may be disposed on an outer or inner surface of implant activator 1304. Power source 1308 may in electrical and wireless communication with processor 1340 and activator implant 1310. For example, power source 1308 may be configured to activate various components including activator antenna 1310 and processor 1340 by transferring power to these components. Power source 1308 may include any source of power capable of activating activator antenna 1310 or processor 1340, for example a battery.

Activator antenna 1310 may be in communication with processor 1340 and power source 1308, and configured to interact with and activate secondary antenna 152 on implant 110. Therefore, activator antenna 1310 may be configured to selectively transfer power from power source 1308 to implant unit 110 during an implantation procedure to cause modulation of at least one nerve in the body of a subject prior to final fixation of implant unit 110. Activator antenna 1310 may include any conductive structure configured to create an electromagnetic field. Activator antenna 1310 may be of any suitable size, shape, and/or configuration. The size, shape, and/or configuration may be determined by the size of the patient, the placement location of implant unit 110, the size and/or shape of implant unit 110, the amount of energy required to activate implant unit 110, the type of receiving electronics present on implant unit 110, etc.

Activator antenna 1310 may include any suitable antenna known to those skilled in the art that may be configured to send and/or receive signals. Suitable antennas may include, but are not limited to, a long-wire antenna, a patch antenna, a helical antenna, etc. In one embodiment, for example, activator antenna 1310 may include a coil antenna. Such a coil antenna may be made from any suitable conductive material and may be configured to include any suitable arrangement of conductive coils (e.g., diameter, number of coils, layout of coils, etc.). A coil antenna suitable for use as activator antenna 1310 may have a diameter of between about 0.1 cm and 10 cm, and may be circular or oval shaped, among other suitable shapes. In some embodiments, activator antenna 1310 may have a diameter between 0.5 cm and 2 cm, and may be oval shaped. A coil antenna suitable for use as activator antenna 1310 may have any number of windings, e.g. 4, 8, 12, or more. A coil antenna suitable for use as activator antenna 1310 may have a wire diameter between about 0.01 mm and 2 mm. These antenna parameters are exemplary only, and may be adjusted above or below the ranges given to achieve suitable results. It is further contemplated that activator antenna 1310 may include the same antenna as secondary antenna 152.

During an exemplary implantation procedure, a surgeon may use delivery tool 1301 to position implant unit 110 in a prospective implantation location and may engage jaws 1305 to bend implant unit 110 such that it substantially conforms to the tissue at the prospective implantation location. For example, implant unit 110 may be positioned in an arc shape in holder 1303 such that first suture guide portion 1502 is disposed on a first open end of the arc and second suture guide portion is disposed on a second open end of the arc (FIG. 13c). Therefore, a first end of the arc may be positioned along first jaw 1306 and the second end of the arc may be positioned along second jaw 1307 of holder 1303. With this arrangement, the first suture guide portion is positioned on the pair of jaws in a location providing access to a first suture hole on the implant unit proximate to a first end of the arc, and the second suture guide portion is positioned on the pair of jaws in a location providing access to a second suture hole on the implant unit proximate to a second end of the arc. The first suture guide portion is configured to direct the suture needle toward the second suture guide portion during the implantation procedure. It is further contemplated that delivery tool 1301 may position implant unit 110 in various other configurations and positions. As noted above, the first and second suture guide portions 1502, 1503 may be configured such that the second suture guide portion 1503 may guide a surgical needle after exiting first suture guide portion 1502. Therefore, a user (e.g. surgeon) may pass the surgical needle through first suture guide portion 1502, through implant unit 110, and then through second suture guide portion 1503. The surgical needle may pass through surgical mesh 1050 after exiting first suture guide portion 1502. The curved channel of second suture guide portion 1503 may provide a pathway for the surgical needle, thus allowing a surgeon to follow the pathway when suturing implant 110 with the surgical needle. In some embodiments, surgical needle may include surgical suture to suture implant within a patient. Additionally, it is further contemplated that an automatic suturing unit (not shown) may guide the suture from first suture guide portion 1502 and through the curved channel of second suture guide portion 1503.

A locking mechanism, such as ratchet mechanism 1406 may lock and maintain jaws 1306, 1307 in a fixed position during the implantation of implant unit 110. For example, ratchet mechanism 1406 may secure jaws 1306, 1307 into a suitable position for implant unit 110 to form the arc shape while allowing hands free operation by a user. The locking mechanism may also affix delivery tool 1301 in a fixed position relative to tissue in the body of a subject. For example, the operator may slide jaws 1307, 1307 over a genioglossus muscle in the subject and lock the locking mechanism once a desired location is reached. The implant may then be activated in that location to test for a desired level of nerve modulation and/or muscle contraction. If the location is not suitable, or does not satisfy expectations, the locking mechanism may be disengaged, and the insert tool 1301 may be moved to another location for testing. Therefore, ratchet mechanism may additionally lock and maintain first and second suture guide portions 1502, 1503 into a desired position during the implantation of implant unit 110. Once a suitable location is found, the implant unit may be sutured in place. In some embodiments, one or more automatic sutures may be triggered in order to secure the implant unit in place.

During an implantation procedure, a user may release ratchet mechanism 1406 and reposition implant unit 110 within holder 1303. For example, the user may reposition implant unit 110 to a configuration that more closely conforms to the patient's tissue at the site of implantation. Additionally, a user may release ratchet mechanism 1406 to move implant unit 110 from a first implantation location to a second implantation location.

The implantation location may be a position suitable for nerve modulation. Once at the desired implantation location, a surgeon may then depress slideable engagement portion 1321 and slide implant activator 1304 from the first position as shown in FIG. 13a to the second position as shown in FIG. 13b. Moving the implant activator 1304 from the first position to the second position may have the effect of bringing activator antenna 1310 into proximity with secondary antenna 152 of implant unit 110. When energized in the second position, for example by power source 1308, activator antenna 1310 may transfer power to implant unit 110. In one embodiment, activator antenna 1310 may transfer power to implant unit 110 through, for example, radiofrequency transmission.

An actuator 1320 may be configured to enable power transmission between activator antenna 1310 and secondary antenna 152 to test the functionality of implant unit 110. As shown in FIG. 13b, actuator 1320 may include a trigger or button disposed on body 1302 of delivery tool 1301. In other embodiments, actuator 1320, may refer to any device that activates the power sent to the implant activator. For example, actuator 1320 may include a switch, with an on/off position, disposed on body 1302 of delivery tool 1301. Actuator 1320 may be positioned such that a user (e.g. surgeon) may engage the switch and move it to an "on" position to deliver power to implant activator 1304. In some embodiments, implant activator 1304 may only activate secondary antenna 1310 when actuator 1320 is in the "on" position. Actuator 1320 may act as a safety barrier to prevent any accidental activation of implant activator 1304. In some embodiments, actuator 1320 may be located outside delivery tool 1301 and may include, for example, a cable to be connected with the implant activator.

After shifting the implant activator from the first position to the second position, a user may enable power transmission between activator antenna 1310 and secondary antenna 152 of implant unit 110 to test the functionality of implant unit 110. This may occur prior to final fixation of implant unit 110 to the patient's tissue. Once activated by implant activator 1304, implant unit 110 may be tested via feedback received by implant activator 1304, for example feedback received by processor 1340. It is contemplated that activator antenna 1310 may receive a feedback signal from secondary antenna 152, and processor 1340 may process the feedback signal. Based on the received feedback signal, processor 1340 may determine if a prospective implant location of implant 110 is sufficient to cause modulation of the subject. For example, processor 1340 may determine that implant unit 110 is not in a sufficient location (e.g. too far) from a desired nerve to properly cause modulation of the nerve.

Additionally or alternatively, implant unit 110 may be tested through one or more patient signals, for example observation of patient response. A surgeon may determine that a prospective implant location is suitable based on whether signals applied to activation modulation electrodes 158*a*, 158*b*, of implant unit 110 effectively modulate the patient's nerves. For example, when placing an implant unit 110 for treatment of OSA, a surgeon may determine a prospective implantation location by observing a patient's tongue movement during power transmission. In some embodiments, a surgeon may determine that a first implant location is not suitable, and may move implant unit 110 to a second implant location. The surgeon may then determine that the second implant location is suitable for nerve modulation. After determining that a prospective implantation location constitutes a suitable modulation position, the surgeon may then secure the implant unit 110 in position with sutures, adhesives, clamps, or various other attachment means.

Implant activator 1304 may also be configured to verify the functionality of implant unit 110 prior to the beginning of an implantation procedure. For example, implant activator 1304 may be configured to verify that implant 110 is working properly and able to sufficiently modulate a patient once implanted within the patient. A surgeon may prepare delivery tool 1301 with implant unit 110 as described above (e.g. between jaws 1305), and shift implant activator 1304 from the first position to the second position along body 1302. Implant unit 110 may be shifted to the second position before it is implanted in the patient's body. In this method, the surgeon may then activate implant unit 110 to verify that implant unit 110 does not suffer from manufacturing defects. Implant activator 1304 may use, for example, coupling detection techniques described herein in order to verify the functionality of implant unit 110. A result of such verification may be outputted via an audio output, a visual output, and/or a tactile output, for example.

Other embodiments of the present disclosure will be apparent to those skilled in the art from consideration of the specification and practice of the present disclosure.

Additional aspects of the invention are described in the following numbered paragraphs, which are part of the description of exemplary embodiments of the invention. Each numbered paragraph stands on its own as a separate embodiment of the invention.

The invention claimed is:

1. A device for treating sleep disordered breathing from a location external to a body of a subject by wirelessly powering an implant unit in the body of the subject, wherein the implant unit includes a secondary antenna for wirelessly receiving energy, the device comprising:
   a primary antenna configured to be located external to the subject;
   a circuit electrically connected to the primary antenna and comprising a plurality of selectable capacitors, the circuit including a switch and a storage capacitor; and
   at least one processor configured to:
      determine a degree of coupling between the primary antenna and the secondary antenna by monitoring a signal component on the primary antenna arising as a result of coupling between the primary antenna and the secondary antenna;
      determine a mismatch between a first resonant frequency associated with the primary antenna and a second resonant frequency associated with the secondary antenna based on the determined degree of coupling;
      alter the first resonant frequency associated with the primary antenna to reduce the mismatch, wherein the alteration of the first resonant frequency is performed by selectively including or excluding at least one capacitor, from among the plurality of selectable capacitors, into or out of the circuit, to determine an optimal capacitor combination based on comparison of a frequency match between the first resonant frequency and the second resonant frequency to a threshold frequency match value; and
      alter a driving frequency of the circuit based on the altered first resonant frequency, the driving frequency being altered by alternating the switch between a first state in which enemy is stored in the storage capacitor and a second state in which the stored energy is released to the primary antenna.

2. The device of claim 1, wherein the plurality of selectable capacitors each have an adjustable capacitance to provide a plurality of capacitance values.

3. The device of claim 1, wherein the plurality of selectable capacitors include at least one trimming capacitor, and wherein the at least one processor is further configured to adjust a resonant frequency associated with the primary antenna by changing the capacitance of the at least one trimming capacitor.

4. The device of claim 1, wherein selectively including or excluding at least one capacitor causes a difference between a first resonant frequency associated with the primary antenna and a second resonant frequency associated with the secondary antenna to be no more than 30% of the first resonant frequency.

5. The device of claim 1, wherein selectively including or excluding at least one capacitor enables at least 50% energy transfer efficiency between the device and the implant unit.

6. The device of claim 1, wherein the at least one processor is further configured to selectively include or exclude the at least one capacitor into or out of the circuit by controlling one or more switches.

7. The device of claim 6, wherein the one or more switches include transistors or relays.

* * * * *

UNITED STATES PATENT AND TRADEMARK OFFICE
CERTIFICATE OF CORRECTION

PATENT NO. : 11,253,712 B2
APPLICATION NO. : 14/623190
DATED : February 22, 2022
INVENTOR(S) : Adi Mashiach Page 1 of 1

It is certified that error appears in the above-identified patent and that said Letters Patent is hereby corrected as shown below:

In the Claims

Claim 1, Column 58, Line 25 "in which enemy is stored" should read --in which energy is stored--.

Signed and Sealed this
Twenty-fourth Day of January, 2023

Katherine Kelly Vidal
*Director of the United States Patent and Trademark Office*